(12) United States Patent
Manash et al.

(10) Patent No.: US 10,646,340 B2
(45) Date of Patent: May 12, 2020

(54) STEERABLE DELIVERY SYSTEM FOR REPLACEMENT MITRAL VALVE

(71) Applicant: Edwards Lifesciences Corporation, Irvine, CA (US)

(72) Inventors: Boaz Manash, Givat Ada (IL); Oren Cohen, Kadima (IL); Noam Nir, Gesher Haziv (IL); Ilan Tamir, Irvine, CA (US); Eitan Atias, Tel-Aviv (IL); Ofir Witzman, Kfar Saba (IL); Michal Aliza Ruchelsman, Zichron Yaakov (IL)

(73) Assignee: Edwards Lifesciences Corporation, Irvine, CA (US)

( * ) Notice: Subject to any disclaimer, the term of this patent is extended or adjusted under 35 U.S.C. 154(b) by 286 days.

(21) Appl. No.: 15/680,030

(22) Filed: Aug. 17, 2017

(65) Prior Publication Data

US 2018/0049873 A1    Feb. 22, 2018

Related U.S. Application Data

(60) Provisional application No. 62/377,203, filed on Aug. 19, 2016.

(51) Int. Cl.
*A61F 2/24* (2006.01)
*A61B 17/00* (2006.01)
(Continued)

(52) U.S. Cl.
CPC .......... *A61F 2/2436* (2013.01); *A61F 2/2418* (2013.01); *A61F 2/2433* (2013.01);
(Continued)

(58) Field of Classification Search
CPC .......... A61B 2017/00327; A61B 2017/00323; A61B 2017/00318; A61B 2017/00336;
(Continued)

(56) References Cited

U.S. PATENT DOCUMENTS

| 3,657,744 A | 4/1972 | Ersek |
| 3,671,979 A | 6/1972 | Moulopoulos |

(Continued)

FOREIGN PATENT DOCUMENTS

| CA | 2304325 A1 | 10/2000 |
| CA | 2827556 A1 | 7/2012 |

(Continued)

OTHER PUBLICATIONS

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

(Continued)

*Primary Examiner* — Christopher L Templeton
(74) *Attorney, Agent, or Firm* — Knobbe Martens Olson & Bear LLP

(57) ABSTRACT

Devices, systems and methods are described herein to provide improved steerability for delivering a prosthesis to a body location, for example, for delivering a replacement mitral valve to a native mitral valve location. The delivery system can include a number of advantageous steering and delivery features, in particular for the transseptal delivery approach.

19 Claims, 43 Drawing Sheets

(51) Int. Cl.
  *A61B 1/005* (2006.01)
  *A61M 25/01* (2006.01)
  *A61M 25/00* (2006.01)
  *A61M 25/09* (2006.01)
  *A61F 2/95* (2013.01)

(52) U.S. Cl.
  CPC ....... *A61F 2/2439* (2013.01); *A61M 25/0029* (2013.01); *A61M 25/0068* (2013.01); *A61M 25/0138* (2013.01); *A61M 25/09* (2013.01); *A61B 1/0057* (2013.01); *A61B 17/00234* (2013.01); *A61B 2017/003* (2013.01); *A61B 2017/00309* (2013.01); *A61B 2017/00318* (2013.01); *A61B 2017/00323* (2013.01); *A61F 2002/9511* (2013.01); *A61F 2002/9517* (2013.01); *A61F 2220/0008* (2013.01); *A61M 25/0133* (2013.01); *A61M 25/0147* (2013.01); *A61M 2025/0039* (2013.01); *A61M 2025/015* (2013.01)

(58) Field of Classification Search
  CPC ......... A61B 2017/32113; A61B 2017/320071; A61B 17/3211; A61B 17/32053; A61B 1/0057; A61M 25/0133; A61M 25/0138; A61M 25/0147; A61M 25/0152
  See application file for complete search history.

(56) References Cited

U.S. PATENT DOCUMENTS

| | | | |
|---|---|---|---|
| 3,739,402 | A | 6/1973 | Cooley et al. |
| 4,056,854 | A | 11/1977 | Boretos et al. |
| 4,079,468 | A | 3/1978 | Liotta et al. |
| 4,204,283 | A | 5/1980 | Bellhouse et al. |
| 4,222,126 | A | 9/1980 | Boretos et al. |
| 4,265,694 | A | 5/1981 | Boretos et al. |
| 4,339,831 | A | 7/1982 | Johnson |
| 4,340,977 | A | 7/1982 | Brownlee et al. |
| 4,470,157 | A | 9/1984 | Love |
| 4,477,930 | A | 10/1984 | Totten et al. |
| 4,490,859 | A | 1/1985 | Black et al. |
| 4,553,545 | A | 11/1985 | Maass et al. |
| 4,777,951 | A | 10/1988 | Cribier et al. |
| 4,865,600 | A | 9/1989 | Carpentier et al. |
| 4,994,077 | A | 2/1991 | Dobben |
| 5,326,371 | A | 7/1994 | Love et al. |
| 5,329,923 | A * | 7/1994 | Lundquist .......... A61B 18/1492 600/373 |
| 5,332,402 | A | 7/1994 | Teitelbaum |
| 5,370,685 | A | 12/1994 | Stevens |
| 5,411,552 | A | 5/1995 | Andersen et al. |
| 5,415,667 | A | 5/1995 | Frater |
| 5,545,214 | A | 8/1996 | Stevens |
| 5,554,185 | A | 9/1996 | Block et al. |
| 5,697,382 | A | 12/1997 | Love et al. |
| 5,833,692 | A * | 11/1998 | Cesarini .......... A61B 17/32002 606/79 |
| 5,840,081 | A | 11/1998 | Andersen et al. |
| 5,855,601 | A | 1/1999 | Bessler et al. |
| 5,957,949 | A | 9/1999 | Leonhardt et al. |
| 6,048,329 | A * | 4/2000 | Thompson ......... A61B 18/1492 604/95.04 |
| 6,071,274 | A * | 6/2000 | Thompson ......... A61B 18/1492 604/528 |
| 6,086,612 | A | 7/2000 | Jansen |
| 6,113,631 | A | 9/2000 | Jansen |
| 6,168,614 | B1 | 1/2001 | Andersen et al. |
| 6,251,093 | B1 | 6/2001 | Valley et al. |
| 6,312,465 | B1 | 11/2001 | Griffin et al. |
| 6,332,880 | B1 * | 12/2001 | Yang ................ A61M 25/0043 604/528 |
| 6,358,277 | B1 | 3/2002 | Duran |
| 6,440,164 | B1 | 8/2002 | DiMatteo et al. |
| 6,458,153 | B1 | 10/2002 | Bailey et al. |
| 6,482,228 | B1 | 11/2002 | Norred |
| 6,527,800 | B1 | 3/2003 | McGuckin, Jr. et al. |
| 6,582,462 | B1 | 6/2003 | Andersen et al. |
| 6,610,088 | B1 | 8/2003 | Gabbay |
| 6,629,534 | B1 | 10/2003 | St. Goar et al. |
| 6,652,578 | B2 | 11/2003 | Bailey et al. |
| 6,676,698 | B2 | 1/2004 | McGuckin, Jr. et al. |
| 6,695,878 | B2 | 2/2004 | McGuckin, Jr. et al. |
| 6,712,836 | B1 | 3/2004 | Berg et al. |
| 6,730,118 | B2 | 5/2004 | Spenser et al. |
| 6,767,362 | B2 | 7/2004 | Schreck |
| 6,780,200 | B2 | 8/2004 | Jansen |
| 6,790,229 | B1 | 9/2004 | Berreklouw |
| 6,790,230 | B2 | 9/2004 | Beyersdorf et al. |
| 6,875,231 | B2 | 4/2005 | Anduiza et al. |
| 6,893,460 | B2 | 5/2005 | Spenser et al. |
| 6,908,481 | B2 | 6/2005 | Cribier |
| 7,018,406 | B2 | 3/2006 | Seguin et al. |
| 7,186,265 | B2 | 3/2007 | Sharkawy et al. |
| 7,198,646 | B2 | 4/2007 | Figulla et al. |
| 7,201,772 | B2 | 4/2007 | Schwammenthal et al. |
| 7,276,078 | B2 | 10/2007 | Spenser et al. |
| 7,329,278 | B2 | 2/2008 | Seguin et al. |
| 7,381,219 | B2 | 6/2008 | Salahieh et al. |
| 7,393,360 | B2 | 7/2008 | Spenser et al. |
| 7,429,269 | B2 | 9/2008 | Schwammenthal et al. |
| 7,442,204 | B2 | 10/2008 | Schwammenthal et al. |
| 7,445,631 | B2 | 11/2008 | Salahieh et al. |
| 7,462,191 | B2 | 12/2008 | Spenser et al. |
| 7,510,575 | B2 | 3/2009 | Spenser et al. |
| 7,524,330 | B2 | 4/2009 | Berreklouw |
| 7,585,321 | B2 | 9/2009 | Cribier |
| 7,618,446 | B2 | 11/2009 | Andersen et al. |
| 7,621,948 | B2 | 11/2009 | Herrmann et al. |
| 7,628,805 | B2 | 12/2009 | Spenser et al. |
| 7,748,389 | B2 | 7/2010 | Salahieh et al. |
| 7,753,949 | B2 | 7/2010 | Lamphere et al. |
| 7,803,185 | B2 | 9/2010 | Gabbay |
| 7,806,919 | B2 | 10/2010 | Bloom et al. |
| 7,815,673 | B2 | 10/2010 | Bloom et al. |
| 7,824,443 | B2 | 11/2010 | Salahieh et al. |
| 7,892,281 | B2 | 2/2011 | Seguin et al. |
| 7,914,569 | B2 | 3/2011 | Nguyen et al. |
| 7,947,075 | B2 | 5/2011 | Goetz et al. |
| 7,959,672 | B2 | 6/2011 | Salahieh et al. |
| 7,972,378 | B2 | 7/2011 | Tabor et al. |
| 7,981,151 | B2 | 7/2011 | Rowe |
| 7,993,392 | B2 | 8/2011 | Righini et al. |
| 8,016,877 | B2 | 9/2011 | Seguin et al. |
| 8,048,153 | B2 | 11/2011 | Salahieh et al. |
| 8,052,750 | B2 | 11/2011 | Tuval et al. |
| 8,070,800 | B2 | 12/2011 | Lock et al. |
| 8,070,802 | B2 | 12/2011 | Lamphere et al. |
| 8,075,615 | B2 | 12/2011 | Eberhardt et al. |
| 8,080,054 | B2 | 12/2011 | Rowe |
| 8,092,520 | B2 | 1/2012 | Quadri |
| 8,109,996 | B2 | 2/2012 | Stacchino et al. |
| 8,118,866 | B2 | 2/2012 | Herrmann et al. |
| 8,136,218 | B2 | 3/2012 | Millwee et al. |
| 8,137,398 | B2 | 3/2012 | Tuval et al. |
| 8,157,852 | B2 | 4/2012 | Bloom et al. |
| 8,167,934 | B2 | 5/2012 | Styrc et al. |
| 8,182,528 | B2 | 5/2012 | Salahieh et al. |
| 8,182,530 | B2 | 5/2012 | Huber |
| 8,216,301 | B2 | 7/2012 | Bonhoeffer et al. |
| 8,219,229 | B2 | 7/2012 | Cao et al. |
| 8,220,121 | B2 | 7/2012 | Hendriksen et al. |
| 8,221,493 | B2 | 7/2012 | Boyle et al. |
| 8,226,710 | B2 | 7/2012 | Nguyen et al. |
| 8,236,045 | B2 | 8/2012 | Benichou et al. |
| 8,246,675 | B2 | 8/2012 | Zegdi |
| 8,246,678 | B2 | 8/2012 | Salahieh et al. |
| 8,252,051 | B2 | 8/2012 | Chau et al. |
| 8,252,052 | B2 | 8/2012 | Salahieh et al. |
| 8,287,584 | B2 | 10/2012 | Salahieh et al. |
| 8,303,653 | B2 | 11/2012 | Bonhoeffer et al. |
| 8,313,525 | B2 | 11/2012 | Tuval et al. |
| 8,323,335 | B2 | 12/2012 | Rowe et al. |

(56) References Cited

U.S. PATENT DOCUMENTS

| | | |
|---|---|---|
| 8,353,953 B2 | 1/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,203 B2 | 2/2014 | Quadri et al. |
| 8,668,733 B2 | 3/2014 | Haug et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,289,291 B2 | 3/2016 | Gorman, III et al. |
| 9,289,296 B2 | 3/2016 | Braido et al. |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 2001/0007956 A1 | 7/2001 | Letac et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0100571 A1* | 5/2006 | Venturelli ......... A61M 25/0054 604/43 |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |

(56) References Cited

U.S. PATENT DOCUMENTS

| | | |
|---|---|---|
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0135763 A1* | 6/2007 | Musbach .......... A61M 25/0054 604/96.01 |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292199 A1 | 11/2009 | Bielewicz et al. |
| 2009/0292350 A1 | 11/2009 | Eberhardt et al. |
| 2009/0306768 A1 | 12/2009 | Quadri |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0261396 A1 | 10/2013 | Boulais et al. |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0112430 A1 | 4/2015 | Creaven et al. |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0238315 A1 | 8/2015 | Rabito et al. |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |

(56) References Cited

U.S. PATENT DOCUMENTS

| | | |
|---|---|---|
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158009 A1 | 6/2016 | Marchand et al. |
| 2016/0213473 A1 | 7/2016 | Hacohen et al. |
| 2016/0235529 A1 | 8/2016 | Ma et al. |

FOREIGN PATENT DOCUMENTS

| | | |
|---|---|---|
| DE | 102006052564 B3 | 12/2007 |
| EP | 1255510 A1 | 11/2002 |
| EP | 1259194 A1 | 11/2002 |
| EP | 1281375 A2 | 2/2003 |
| EP | 1472996 A1 | 11/2004 |
| EP | 1734903 A1 | 12/2006 |
| EP | 2124826 A1 | 12/2009 |
| EP | 2237746 A2 | 10/2010 |
| EP | 2285317 A1 | 2/2011 |
| EP | 2308425 A1 | 4/2011 |
| EP | 2319458 A1 | 5/2011 |
| EP | 2496182 A1 | 9/2012 |
| EP | 2566416 A1 | 3/2013 |
| EP | 2745805 A1 | 6/2014 |
| EP | 2749254 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2926766 B1 | 2/2016 |
| EP | 2985206 A1 | 2/2016 |
| GB | 126447 A | 5/1919 |
| GB | 1315844 A | 5/1973 |
| GB | 2398245 A | 8/2004 |
| JP | 2002540889 A | 12/2002 |
| JP | 2008541865 A | 11/2008 |
| WO | 1997049355 A1 | 12/1997 |
| WO | 0061034 A1 | 10/2000 |
| WO | 03092554 A1 | 11/2003 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009094500 A1 | 7/2009 |
| WO | 2009134701 A2 | 11/2009 |
| WO | 2010008549 A1 | 1/2010 |
| WO | 2010037141 A1 | 4/2010 |
| WO | 2010040009 A1 | 4/2010 |
| WO | 2010057262 A1 | 5/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Bavaria, Joseph E. M.D. et al.: "Transcatheter Mitral Valve Implantation: The Future Gold Standard for MR?," Applicant requests the Examiner to consider this reference to be prior art as of Dec. 2010.
Int'l. Search Report for PCT/US2017/047434, dated Nov. 30, 2017.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Bavaria, Joseph E. M.D.: "CardiAQ Valve Technologies: Transcatheter Mitral Valve Implantation," Sep. 21, 2009.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.
Boudjemline, Younes, et al., "Steps Toward the Percutaneous Replacement of Atrioventricular Valves," JACC, vol. 46, No. 2, Jul. 19, 2005:360-5.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31, Applicant believes this may have been available as early as Dec. 2006.
Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.
Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.
Spillner, J. et al., "New Sutureless 'Atrial—Mitral-Valve Prosthesis' For Minimally Invasive Mitral Valve Therapy," Textile Research Journal, 2010, in 7 pages, Applicant believes this may have been available as early as Aug. 9, 2010.
Karimi, Houshang, et al., "Percutaneous Valve Therapies," SIS 2007 Yearbook, Chapter 11, pp. 1-11.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009)

(56) References Cited

OTHER PUBLICATIONS 124-128, Applicant believes this may have been available as early as Apr. 25, 2009.

Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.

Sondergaard, Lars, et al., "Transcatheter Mitral Valve Implantation: CardiAQ™," Applicant believes this may have been presented at TCT 2013.

Sondergaard, Lars, et al., "Transcatheter Mitral Valve Implantation: CardiAQ™," Applicant believes this may have been presented at EuroPCR 2013.

Sondergaard, Lars, "CardiAQ TMVR FIH—Generation 2," Applicants believe this may have been presented in 2014 at the TVT symposium.

CardiAQ Valve Technologies, "Innovations in Heart Valve Therapy," In3 San Francisco, Jun. 18, 2008, PowerPoint presentation in 19 slides.

Ratz, J. Brent, "LSI EMT Spotlight," May 15, 2009.

Ratz, J. Brent, "In3 Company Overview," Jun. 24, 2009.

"Company Overview," at TVT on Jun. 25, 2009.

Ruiz, Carlos E., "Overview of Novel Transcatheter Valve Technologies," Applicant believes this may have been presented on May 27, 2010 at EuroPCR.

"Update," Applicant believes this may have been presented on Jun. 6, 2010 at TVT.

Mack, Michael, M.D., "Antegrade Transcatheter Mitral valve Implantation: A Short-term Experience in Swine Model," Applicant believes this may have been presented on May 2011 at TVT.

Mack, Michael, M.D., "Antegrade Transcatheter Mitral valve Implantation: On-Going Experience in Swine Model," Applicant believes this may have been presented on Nov. 2011 at TCT.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Quadri, Arshad M.D., "Transcatheter Mitral Valve Implantation (TMVI) (An Acute In Vivo Study)," Applicant believes this may have been presented on Sep. 22, 2010 at TCT.

Masson, Jean-Bernard, et al., "Percutaneous Treatment of Mitral Regurgitation," Circulation: Cardiovascular Interventions, 2:140-146, Applicant believes this may have been available as early as Apr. 14, 2009.

Horvath et al.: "Transapical Aortic Valve Replacement under Real-time Magnetic Resonance Imaging Guidance: Experimental Results with Balloon—Expandable and Self-Expanding Stents," http://www.ncbi.nlm.nih.gov/pmc/articles/PMC3038190/. Jun. 2011.

Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.

Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.

Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).

Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.

Feldman, Ted, MD. "Prospects for Percutaneous Valve Therapies," Circulation 2007;116:2866-2877. Applicant believes that this may be available as early as Dec. 11, 2007.

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.

Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

"CardiAQTM Valve Technologies reports Successful First-in-Human Trans-Apical implantation of its Second Generation Transcatheter Mitral Valve," CardiAQ Valve Technologies Press Release, May 20, 2014.

Dave Fornell, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Neovasc corporate presentation, Oct. 2009, available at http://www.neovasc.com/investors/documents/Neovasc-Corporate-Presentation-October-2009.pdf.

NJ350: Vote for Your Favorite New Jersey Innovations, Jun. 27, 2014, http://www.kilmerhouse.com/2014/06/nj350-vote-for-your-favorite-new-jersey-innovations/.

* cited by examiner

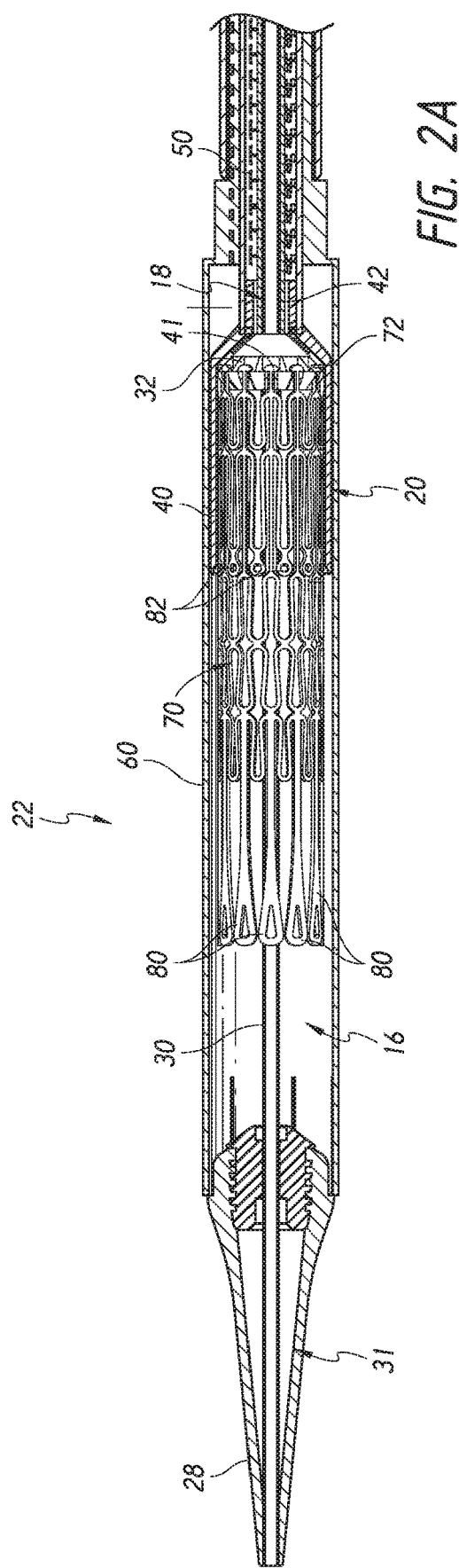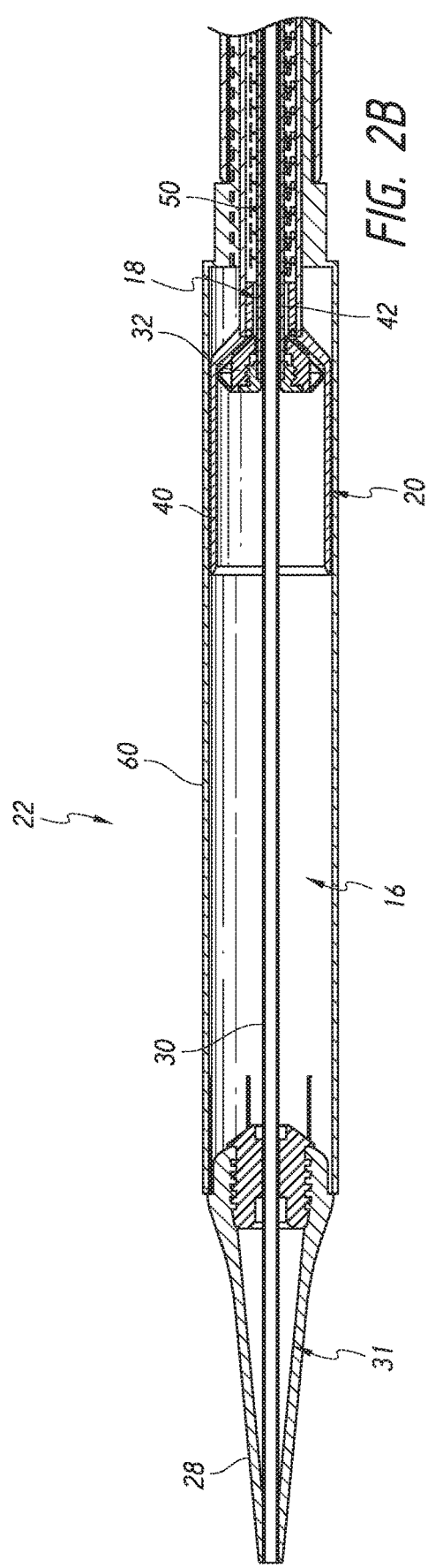

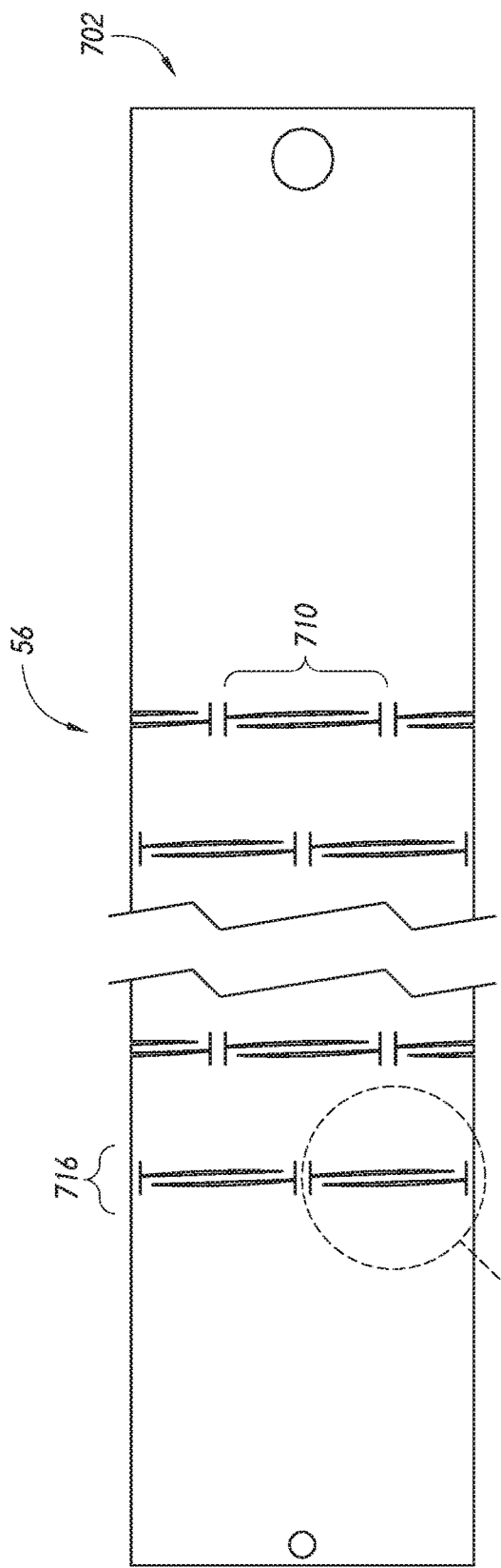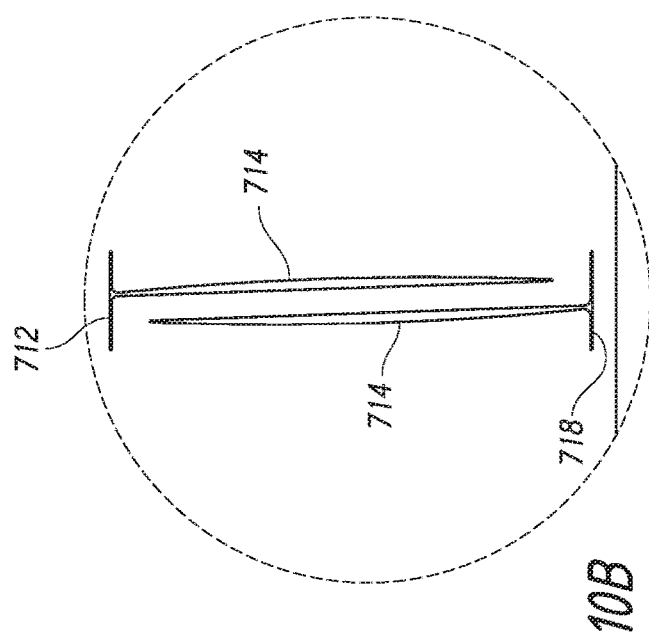

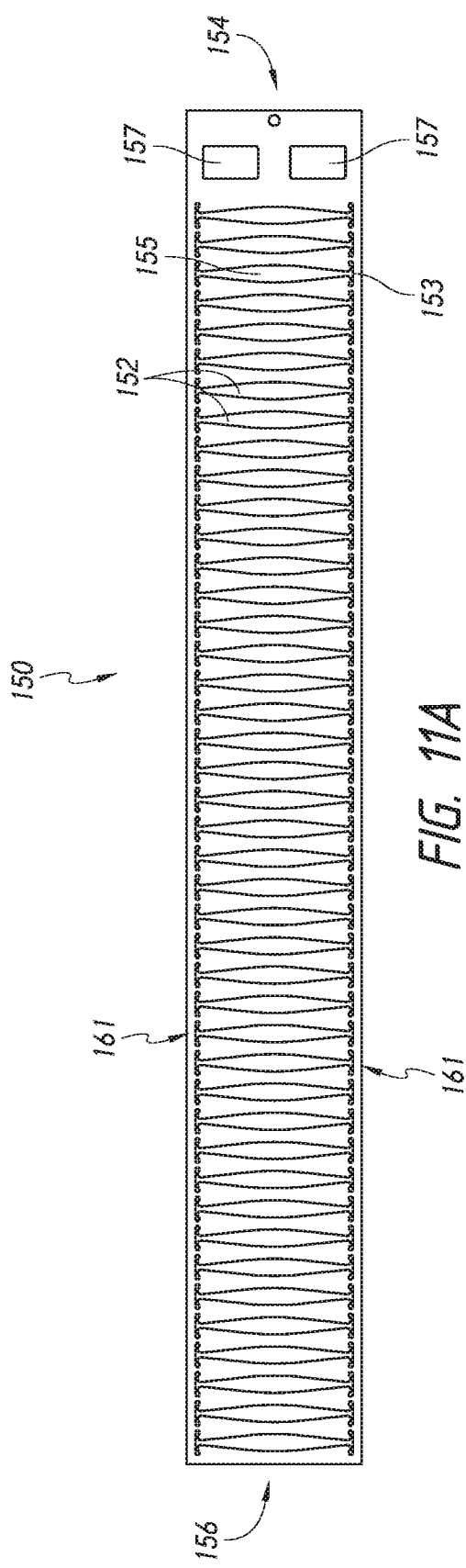
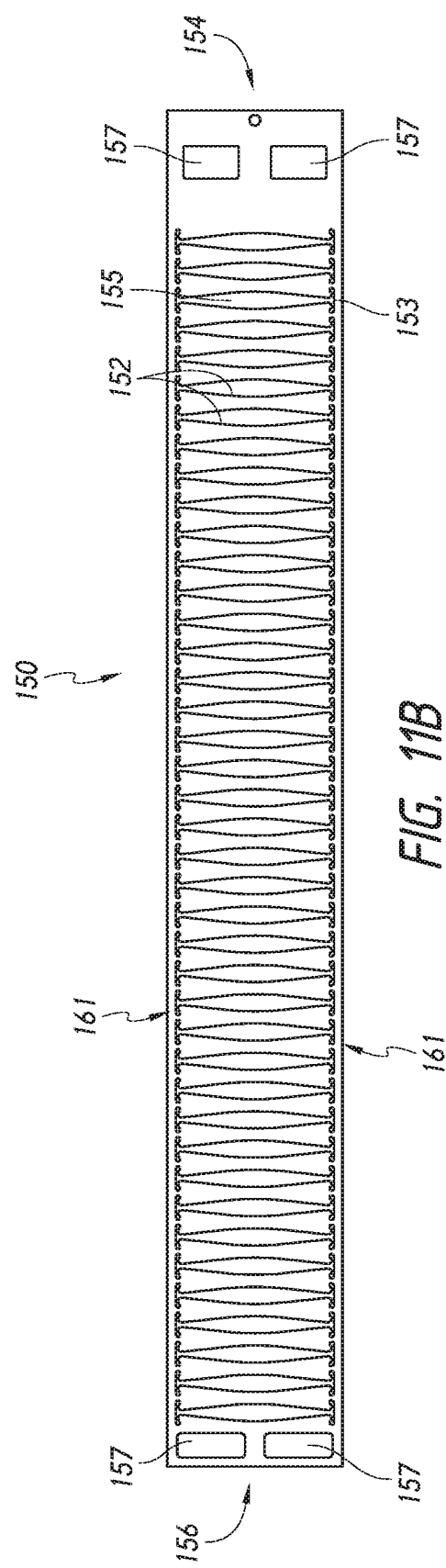

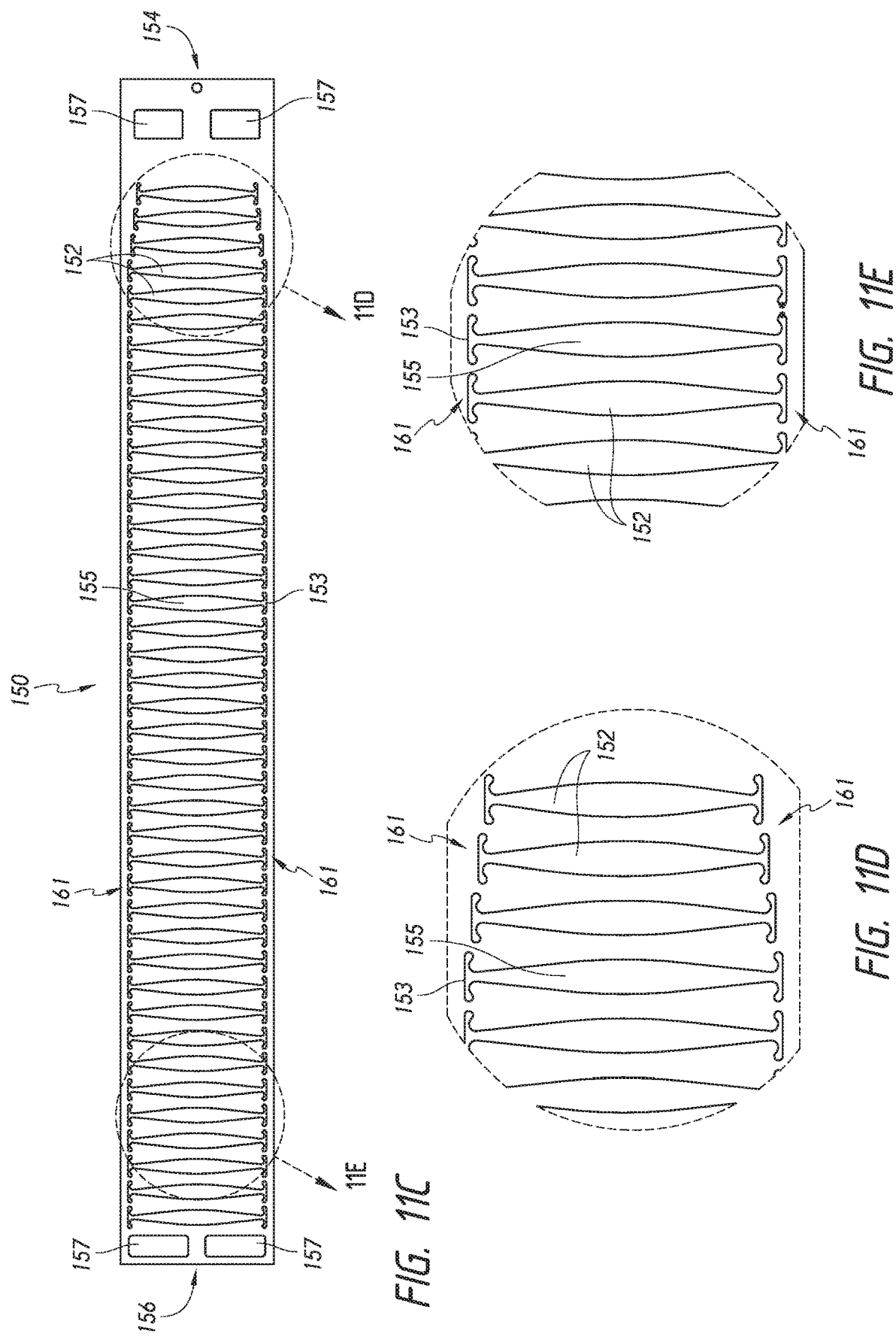

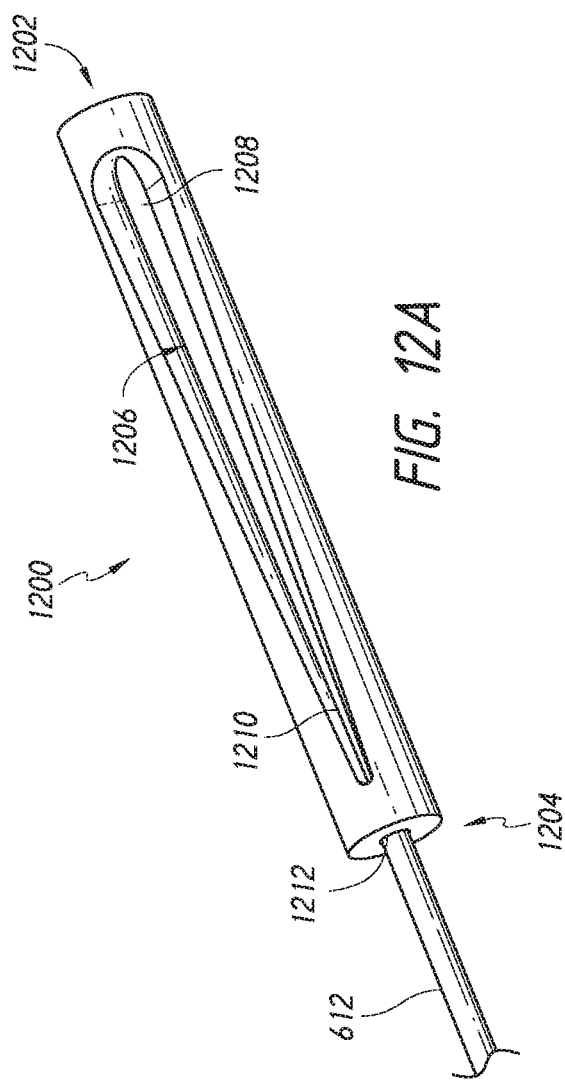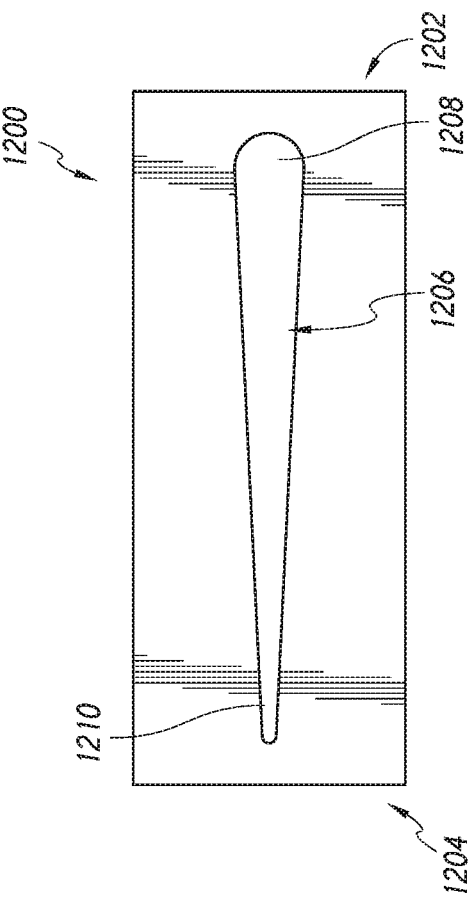

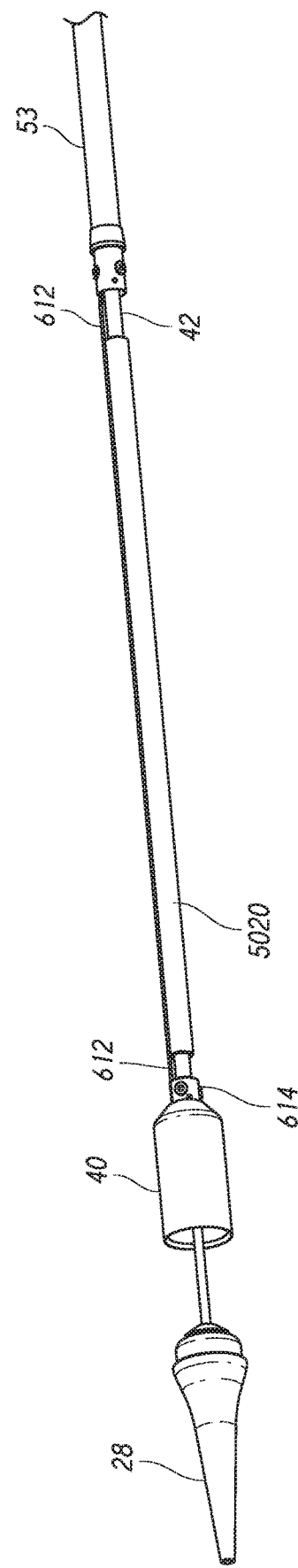

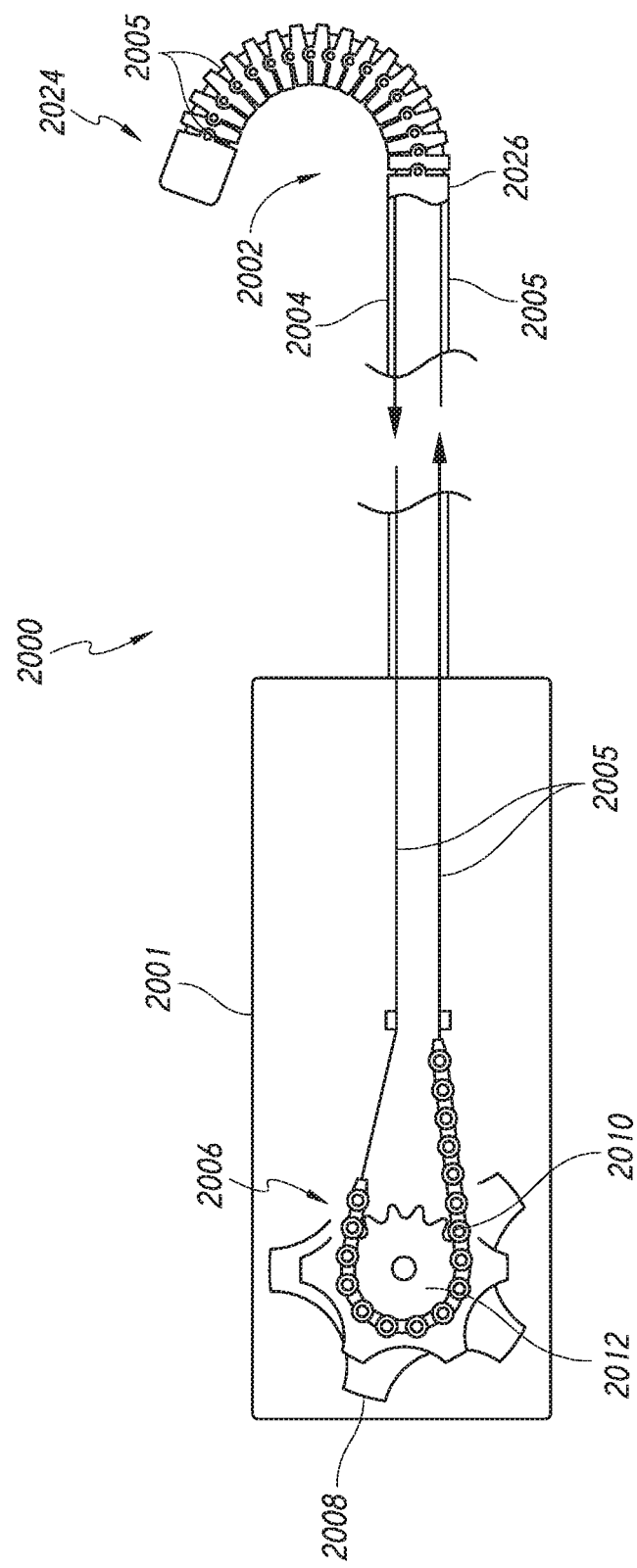

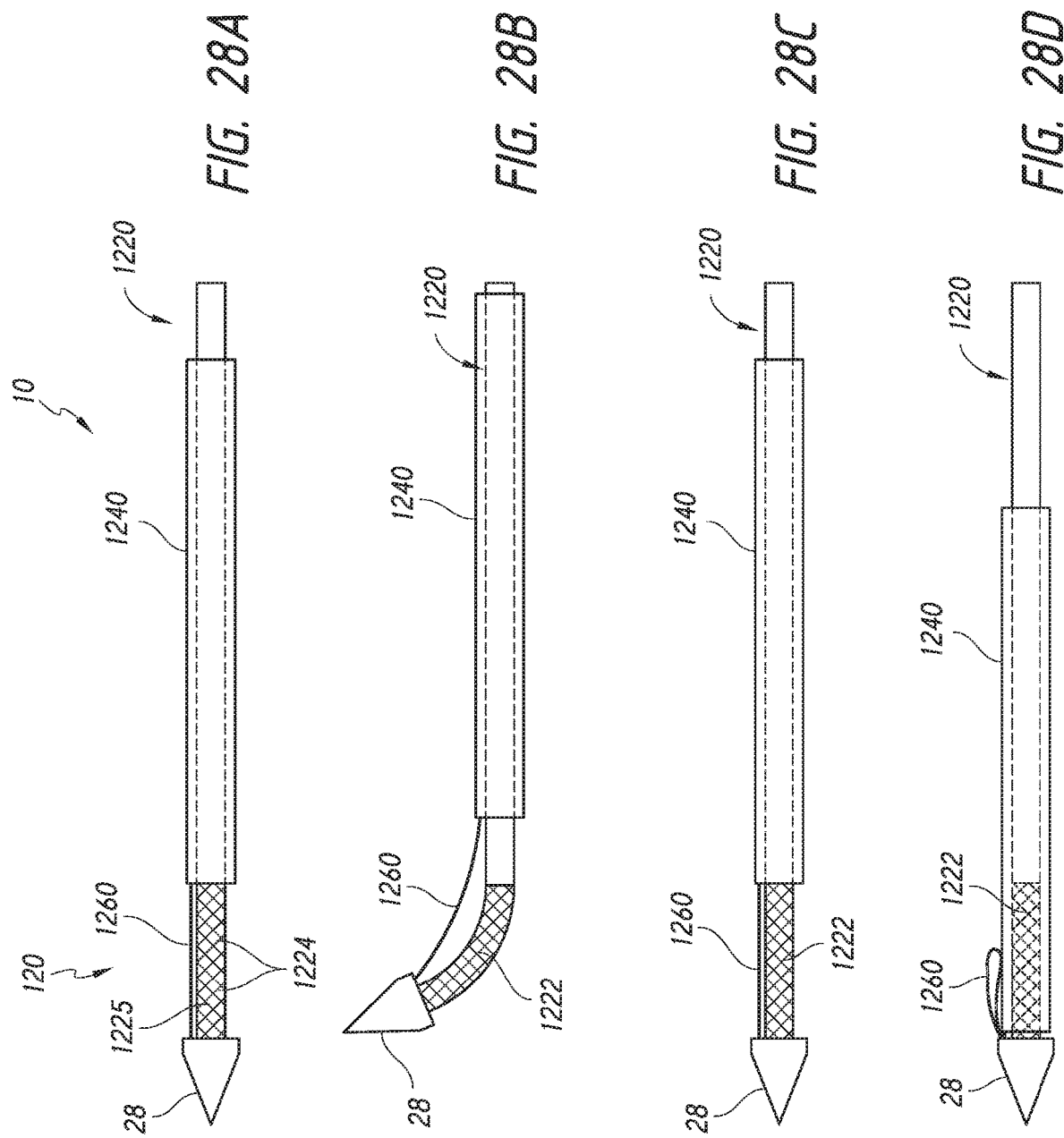

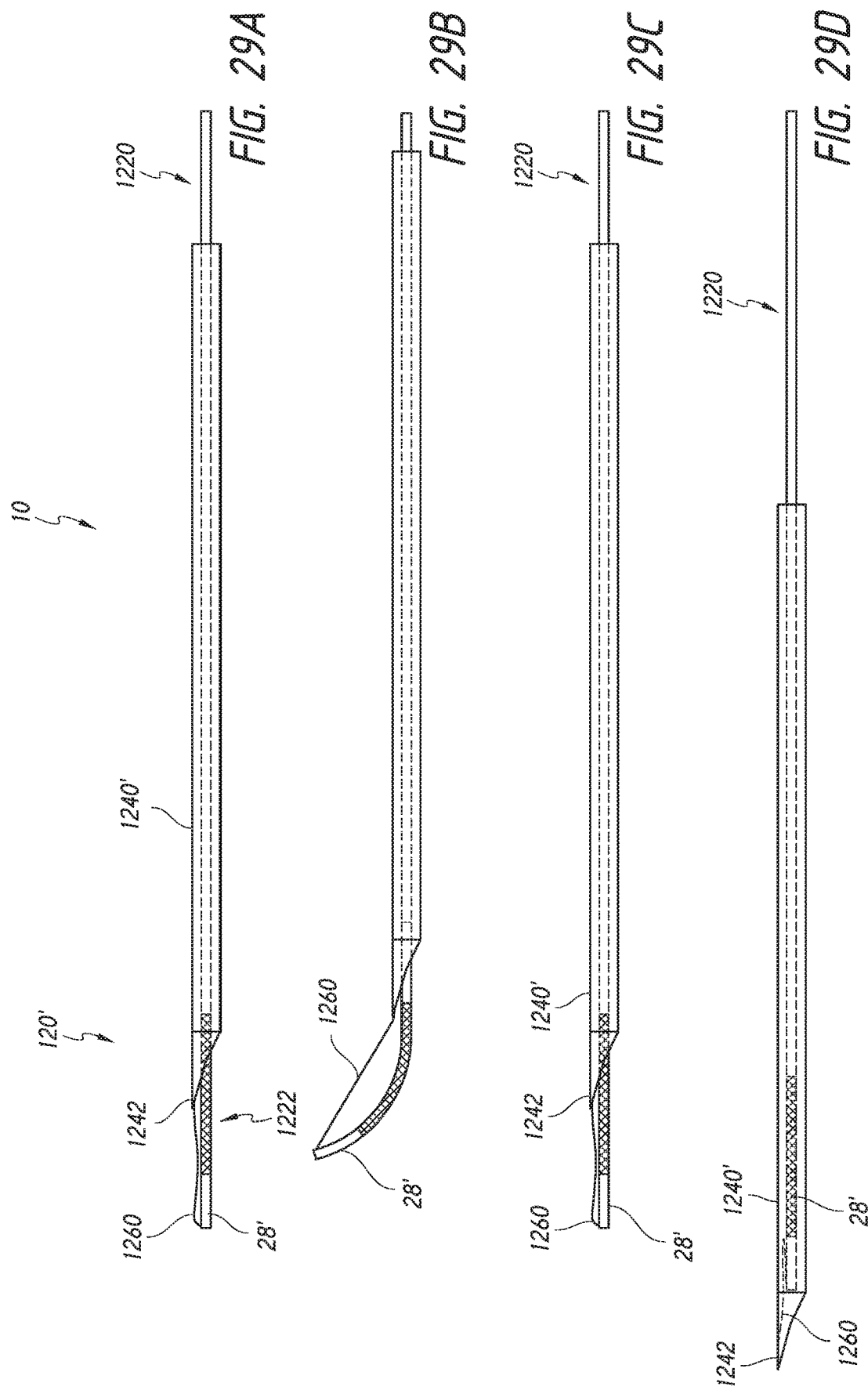

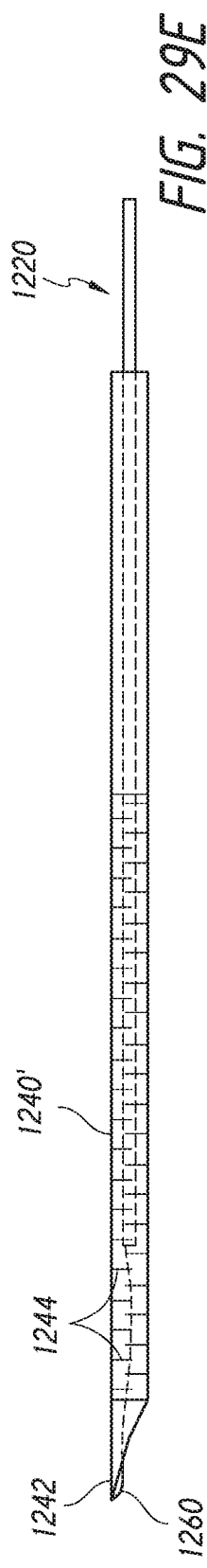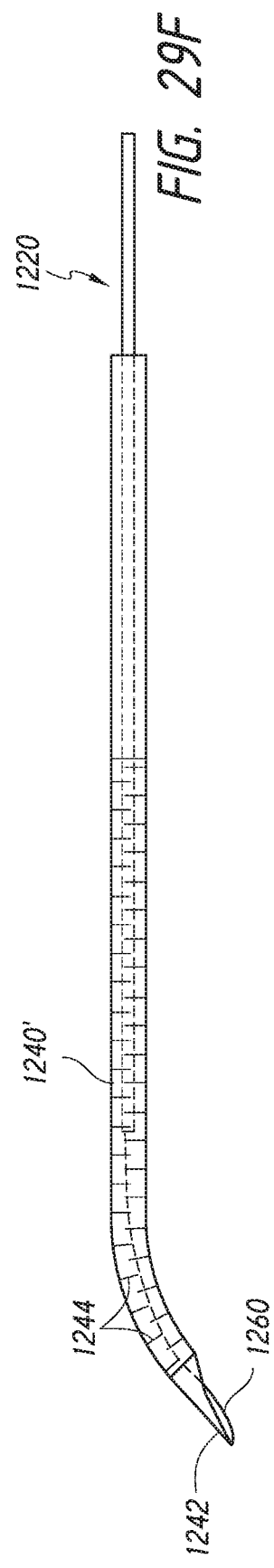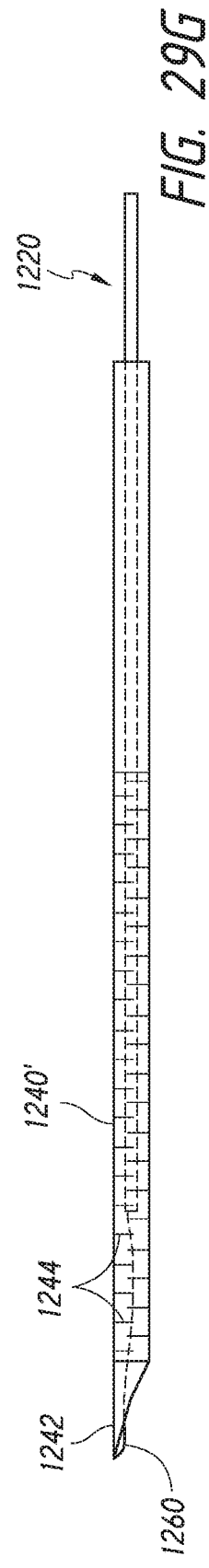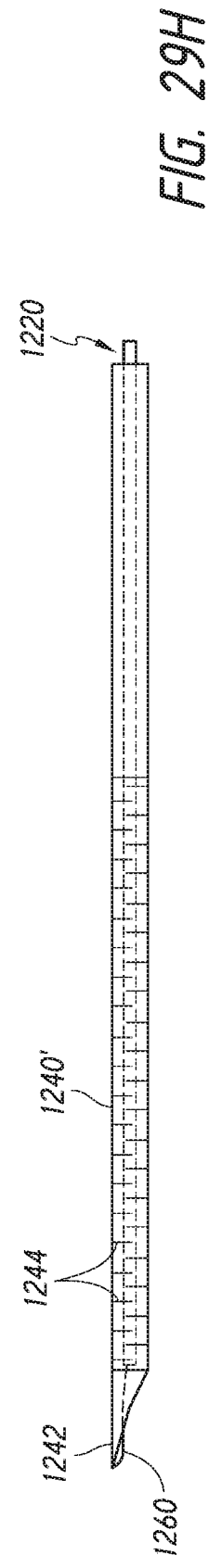

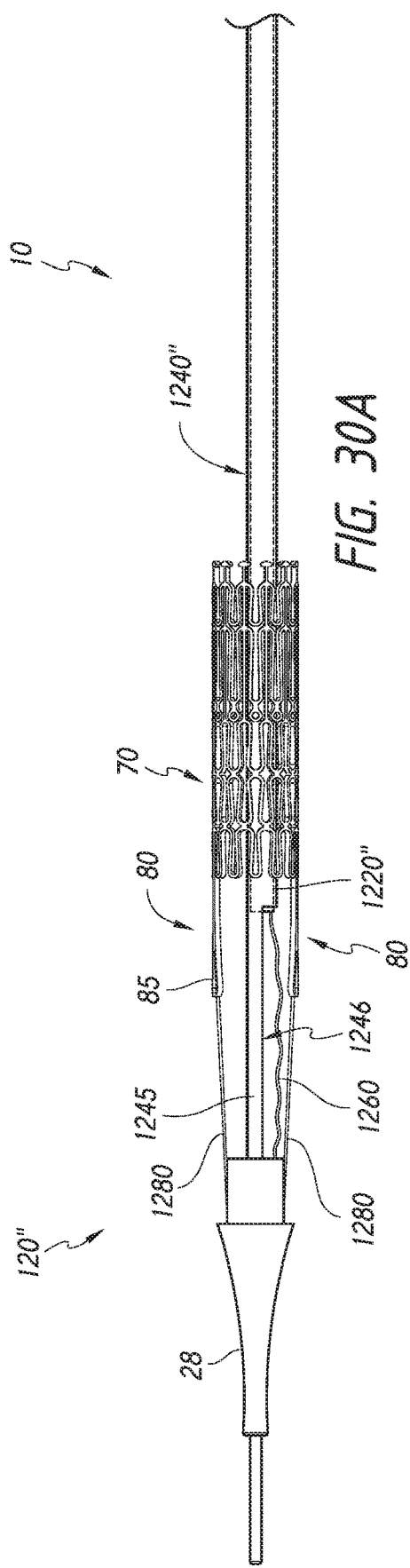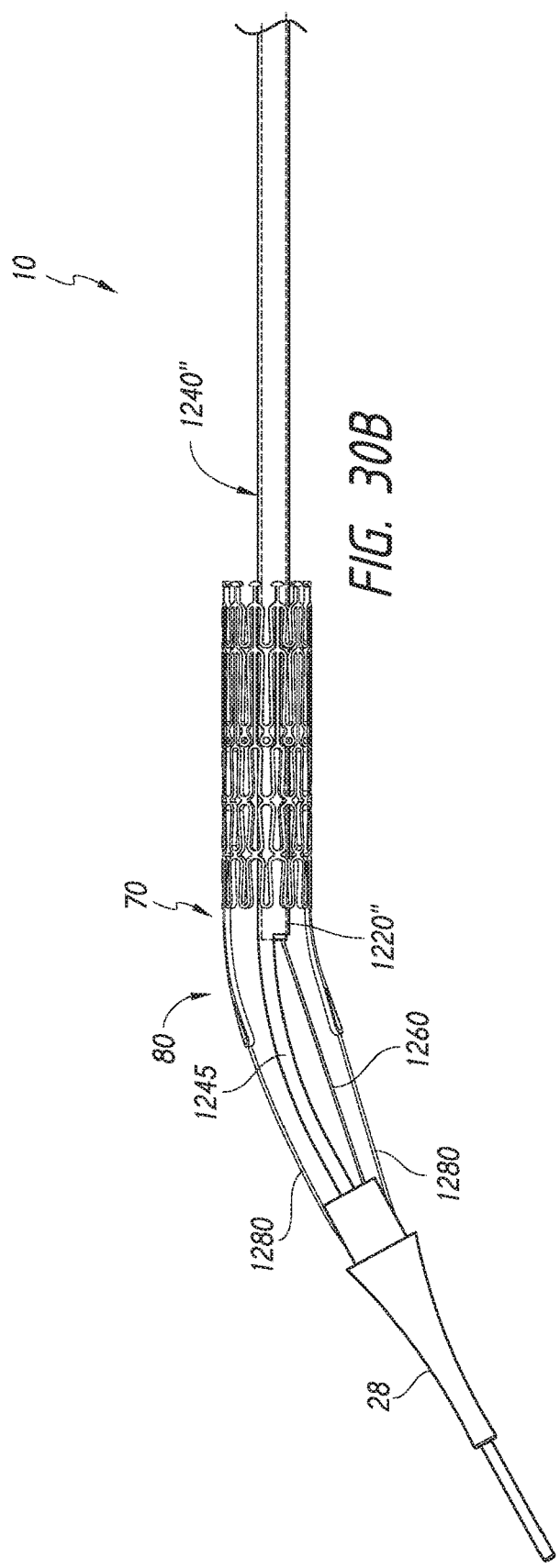

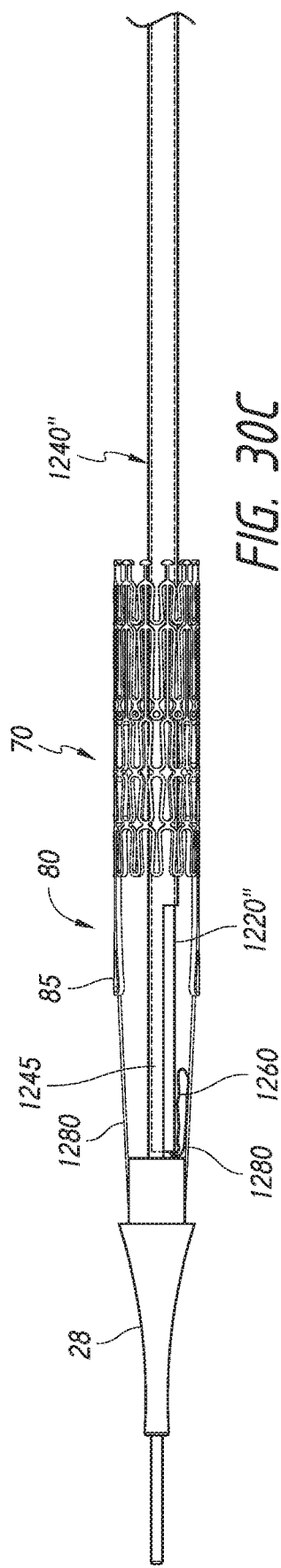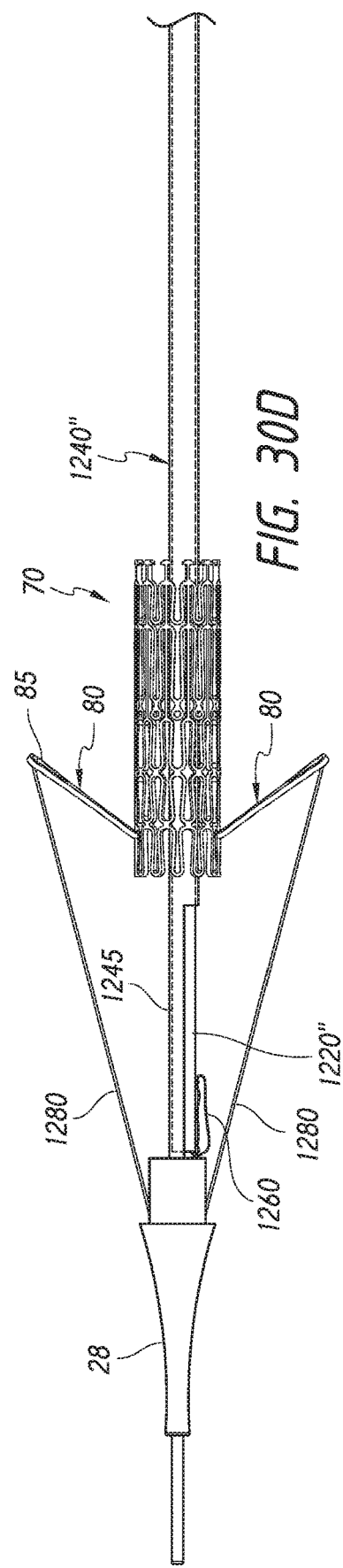

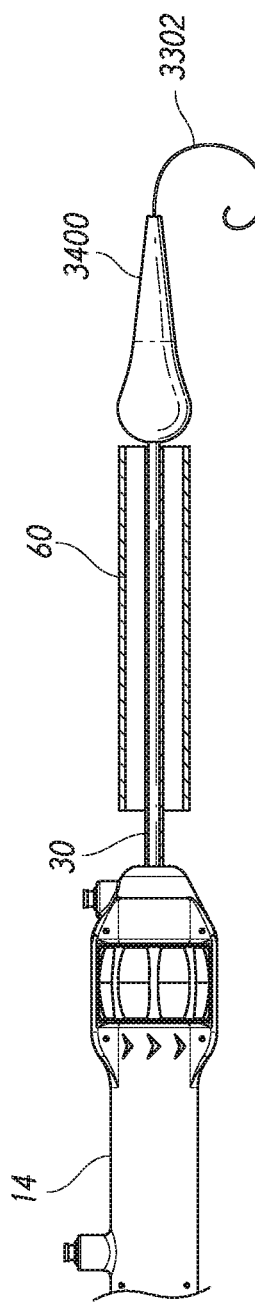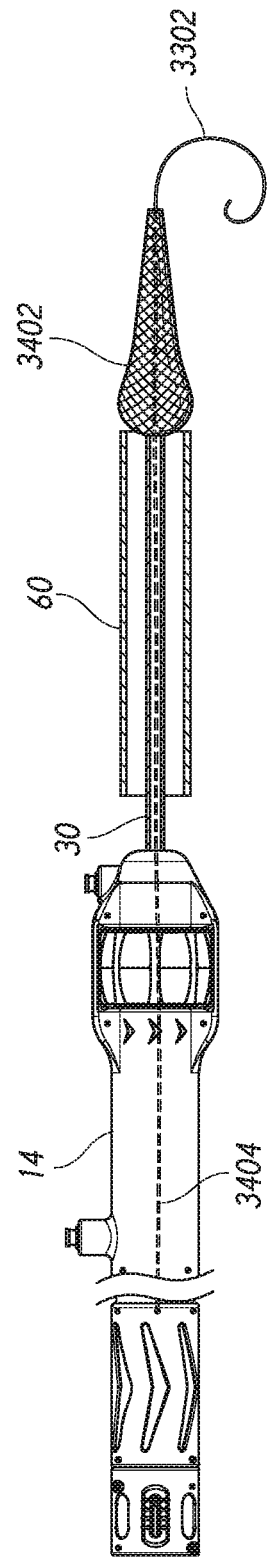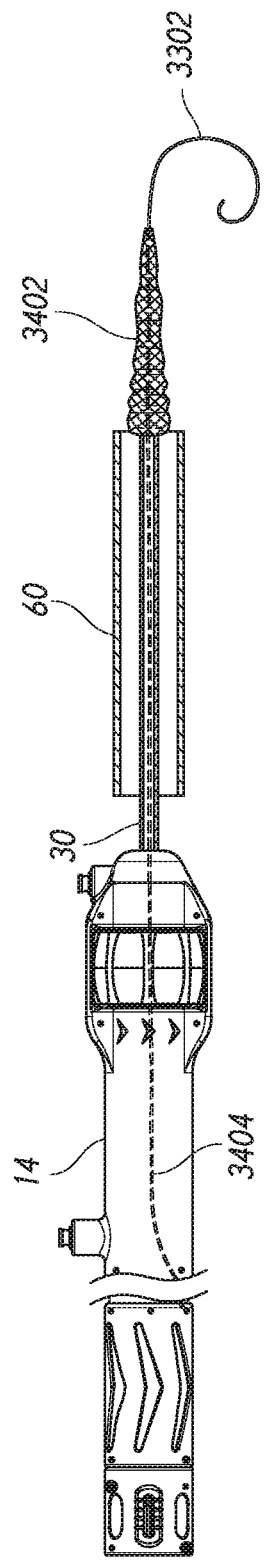

STEERABLE DELIVERY SYSTEM FOR REPLACEMENT MITRAL VALVE

INCORPORATION BY REFERENCE TO ANY PRIORITY APPLICATIONS

This Application claims the benefit of U.S. Provisional Application No. 62/377,203, filed Aug. 19, 2016, titled "STEERABLE DELIVERY SYSTEM FOR REPLACEMENT MITRAL VALVE AND METHODS OF USE," the entirety of which is incorporated herein by reference.

BACKGROUND

Field

Certain embodiments disclosed herein relate generally to prostheses for implantation within a lumen or body cavity and delivery systems for a prosthesis. In particular, the prostheses and delivery systems relate in some embodiments to replacement heart valves, such as replacement mitral heart valves.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the deployment of the prosthesis at the desired location can also be challenging.

SUMMARY

Embodiments of the present disclosure are directed to a prosthesis, such as but not limited to a replacement heart valve. Further embodiments are directed to methods of delivering a prosthesis into a body cavity and/or securing a prosthesis to intralumenal tissue. In some embodiments, a replacement heart valve and methods for delivering a replacement heart valve to a native heart valve, such as a mitral valve, are provided. Embodiments of different delivery systems and methods are also disclosed herein.

Disclosed herein are embodiments of a steerable medical device component. The steerable medical device component can comprise a bending section and a chain and sprocket system. The chain and sprocket system can be configured to cause bending of the bending section. In some embodiments, the steerable medical device component can optionally comprise a bending section comprising a plurality of rings. The plurality of rings can be axially connected to one another to form a lumen through the plurality of rings. Each of the plurality of rings can have an inner surface. Each of the plurality of rings can comprise at least one generally proximally extending pivot member. Each one of the plurality of rings can comprise at least one generally distally facing pivot member. The at least one generally proximally extending pivot member can be configured to pivotably connect to the at least one generally distally facing pivot member of an adjacent ring. Each of the plurality of rings can comprise an eyelet located on the inner surface. The component can have at least one pull wire having a distal end and a proximal end. The at least one pull wire can extend through the eyelet and the lumen of the plurality of rings. The distal end of the at least one pull wire can be connected to a distal section of the bending section. The chain and sprocket system can comprise a chain and a sprocket. An end of the chain can be connected to the proximal end of the at least one pull wire. A middle portion of the chain can wrap at least partially around the sprocket. An articulation knob can be connected to the sprocket for articulation of the bending section by pulling the at least one pull wire.

In some embodiments, the steerable medical device component can further comprise at least two pull wires. Each of the at least two pull wires can be located radially opposite one another through the lumen of the plurality of rings providing for two-dimensional bending of the bending section. In some embodiments, the steerable medical device component can further comprise at least four pull wires. Each of the pull wires located approximately 90° from an adjacent pull wire and provide for three-dimensional bending of the bending section. In some embodiments, the steerable medical device component can further comprise a second chain and sprocket system and a second articulation knob. In some embodiments, each of the plurality of rings can comprise two generally proximal extending pivot members and two generally distally facing pivot members.

Also disclosed herein are embodiments of a steerable medical device component. The component can comprise a first elongate shaft having a proximal end and a distal end. The first elongate shaft can comprise a bending section at the distal end. The component can comprise a second elongate shaft having a proximal end and a distal end. The second elongate shaft can be slideable over the first elongate shaft. The component can comprise a nose cone coupled to the distal end of the first elongate shaft. The component can comprise one or more pull wires connecting the proximal end of the nose cone and the distal end of the second elongate shaft. When the second elongate shaft is translated proximally, the one or more pull wires can pull the nose cone causing the bending section to bend. When the second elongate shaft is pushed distally to at least partially overlap with the bending section of the first elongate shaft, the bending section is configured to resist bending.

In some embodiments, the first and second elongate shafts can be coaxial. In some embodiments, the second elongate shaft can comprise a pointed tip at the distal end. In some embodiments, the bending section can comprise a plurality of perforations. In some embodiments, the bending section can comprise a cut-out slot.

Further disclosed herein are embodiments of a delivery system for delivering an expandable implant to a body location. The delivery system can comprise an outer sheath assembly having a proximal end and a distal end. The outer sheath assembly can be configured to cover a distal end of the expandable implant in a compressed position so that at least one anchor on the expandable implant extends distally. The system can comprise a nose cone attached to a distal end of a nose cone shaft. The nose cone can comprise a pulley. The delivery system can comprise a handle located at a proximal end of the nose cone shaft and outer sheath assembly. The handle can comprise an actuator. The delivery system can comprise at least one tether having a proximal end and a distal end. The proximal end can be configured to be operably connected to the actuator. The distal end can be configured to be operably connected to an anchor of the expandable implant. A portion of the at least one tether between the distal and proximal end can extend through the pulley in the nose cone. Tension on the at least one tether is configured to prevent the anchor from flipping proximally when the outer sheath assembly is removed. The actuator is configured to be actuated to release the tension in the at least one tether thereby allowing the anchor to controllably flip to a proximal direction.

In some embodiments, the tether can comprise a pull wire forming a double strand. The double strand can have a loose-strand end formed by two ends of the pull wire and a continuous end. In some embodiments, the loose-strand end can be configured to be coupled to the actuator and the continuous end is configured to be coupled to the anchor of the implant. In some embodiments, the pull wire can loop through an eyelet of the anchor at the continuous end. In some embodiments, the loose-strand end can be configured to be released from the actuator so that one of the two ends of the pull wire can be pulled to release the anchor from the tether. In some embodiments, the expandable implant can comprise a plurality of anchors and at least as many tethers as anchors. In some embodiments, the delivery system can comprise an expandable nose cone. In some embodiments, the delivery system can comprise a self-expanding wire balloon on a guide wire.

Also disclosed are embodiments of a method of delivering the expandable implant into a heart using the delivery systems disclosed herein. The method can include translating the delivery system at least partially across a fossa ovalis of the heart. The method can further include bending the delivery system away from the fossa ovalis. The method can use the fossa ovalis as a hinge. The method can so that a distal end of the delivery system is directed towards the left ventricle and the delivery system proximal to the fossa ovalis is moved upwards in the right atrium.

Disclosed herein is a transseptal delivery system for replacement mitral valve implantation. The delivery system can comprise a nose cone shaft having a proximal end and a distal end and a lumen extending therethrough. The delivery system can comprise a nose cone provided on the distal end of the nose cone shaft. The nose cone can be transformable. The nose cone can expand between a compressed an expanded configuration. The nose cone shaft can deliver fluid into the nose cone to expand the nose cone. The nose cone can be a polymer. The nose cone can be a mesh. The nose cone can include a pull wire attached to the handle. The nose cone can be compressed by pulling on the pull wire.

A delivery system can include guide wire. The delivery system can include a catheter. The catheter can be slidable over a wire balloon. The wire balloon can be self-expanding. The wire balloon can expand upon release from the catheter. The wire balloon can help the guide wire avoid chordae. The wire balloon can include apertures for blood to pass through. The wire balloon can be metal.

A method of delivering a replacement mitral valve using a delivery system. The delivery system can include a steering catheter. The steering catheter can be slidable over a shaft containing in implant. The steering catheter can cover the implant. The implant can extend partially through the fossa ovalis. The steering catheter can be withdrawn into the right atrium. The steering catheter can be bent away from the fossa ovalis. The steering catheter can be torqued counter clockwise. This torque raises the proximal end of the implant in the right atrium. This torque lowers the distal end of the implant in the left atrium. The implant can translated forward into the mitral valve space.

BRIEF DESCRIPTION OF THE DRAWINGS

FIG. 2A shows a cross-sectional view of the distal end of the delivery system of FIG. 1 loaded with the valve prosthesis of FIG. 3.

FIG. 2B shows a cross-sectional view of the distal end of the delivery system of FIG. 1 without the valve prosthesis of FIG. 3.

FIGS. 10A-10D illustrate flat patterns of the proximal portion of the outer sheath assembly.

FIGS. 11A-E illustrate flat patterns of the distal portion of the outer sheath assembly.

FIGS. 12A-B illustrate a proximal wire connector for retaining a pull wire in the handle.

FIG. 23 shows a perspective view of the distal end of the delivery system of FIG. 22.

FIG. 25 illustrates a cross-section of a delivery system having an articulating mechanism.

FIGS. 28A-D show schematic illustrations of a distal end of a delivery system with the outer sheath assembly and the mid shaft assembly removed and including an inner tube with a bendable portion.

FIGS. 29A-D show an embodiment of a distal end of a delivery system with the outer sheath assembly and the mid shaft assembly removed and including an inner tube with a bendable portion and an outer tube having a pointed tip.

FIGS. 29E-H show an embodiment of a distal end of a delivery system with the outer sheath assembly and the mid shaft assembly removed and including a rigid inner shaft and an outer tube having a pointed tip.

FIGS. 30A-D show schematic illustrations of a delivery system with the outer sheath assembly and the mid shaft assembly removed and including an outer tube with a bendable portion and loaded with a valve prosthesis.

FIG. 34 illustrates an embodiment of an inflatable nosecone.

FIGS. 35A-B illustrate an embodiment of a mesh nosecone in an expanded and deflated configuration.

DETAILED DESCRIPTION

The present specification and drawings provide aspects and features of the disclosure in the context of several embodiments of replacement heart valves, delivery systems and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery system, etc. should not be taken as limiting, and features of any one embodiment discussed herein can be combined with features of other embodiments as desired and when appropriate. While certain of the embodiments described herein are described in connection with a transfemoral delivery approach, it should be understood that these embodiments can be used for other delivery approaches such as, for example, transapical approaches. Moreover, it should be understood that certain of the features described in connection with some embodiments can be incorporated with other embodiments, including those which are described in connection with different delivery approaches.

Delivery System

Figure 1:
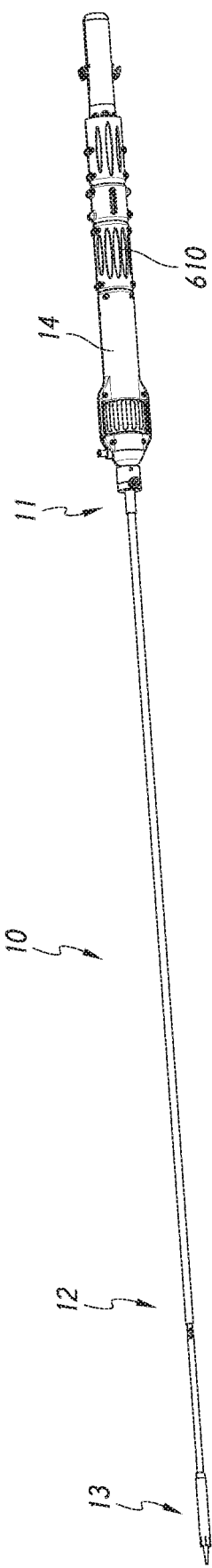
FIG. 1 shows an embodiment of a delivery system.

With reference to FIG. 1, an embodiment of a delivery device or system 10 is shown. The delivery system can be used deploy a prosthesis, such as a replacement heart valve, within the body. Replacement heart valves can be delivered to a patient's heart mitral valve annulus or other heart valve location in various ways, such as by open surgery, minimally-invasive surgery, and percutaneous or transcatheter delivery through the patient's vasculature. Example transfemoral approaches may be found in U.S. Pat. Pub. No. 2015/0238315, filed Feb. 20, 2015, the entirety of which is hereby incorporated by reference in its entirety. While the delivery system 10 is described in connection with a percutaneous delivery approach, and more specifically a transfemoral delivery approach, it should be understood that features of delivery system 10 can be applied to other delivery system, including delivery systems for a transapical delivery approach. Further examples of devices, systems and methods are described in U.S. Provisional Application Nos. 62/163,932, filed May 19, 2015, and 62/210,165, filed Aug. 26, 2015 and U.S. application Ser. No. 15/141,684, filed Apr. 26, 2016, the entirety of each of which is incorporated by reference. In particular, delivery system 10 as described herein can have components, features, and/or functionality similar to those described with respect to delivery systems, devices and methods described in at least paragraphs [0006]-[0037] and [0078]-[0170] of U.S. Provisional Application No. 62/163,932, filed May 19, 2015, including the description relating to FIGS. 1-40B, and all of these descriptions are expressly incorporated by reference herein. Moreover, delivery system 10 as described herein can have components, features, and/or functionality similar to those described with respect to the systems, devices and methods described with respect to paragraphs [0171]-[0197] of U.S. Provisional Application No. 62/163,932, filed May 19, 2015, including the description relating to FIGS. A1-A5, B1-B6, C1-C2 and 41A-42B, and U.S. Provisional Application No. 62/210,165, filed Aug. 26, 2015, and all of these descriptions are expressly incorporated by reference herein.

The delivery system 10 can be used to deploy a prosthesis, such as a replacement heart valve as described elsewhere in this specification, within the body. The delivery system 10 can receive and/or cover portions of the prosthesis such as a first end 301 and second end 303 of the prosthesis 70 illustrated in FIG. 3 below. For example, the delivery system 10 may be used to deliver an expandable implant or prosthesis 70, where the prosthesis 70 includes the first end 301 and the second end 303, and wherein the second 303 end is configured to be deployed or expanded before the first end 301.

The delivery system 10 can be relatively flexible. In some embodiments, the delivery system 10 is particularly suitable for delivering a replacement heart valve to a mitral valve location through a transseptal approach (e.g., between the right atrium and left atrium via a transseptal puncture).

As shown in FIG. 1, the delivery system 10 can include an elongate shaft assembly 12 comprising a proximal end 11 and a distal end 13, wherein a handle 14 is coupled to the proximal end of the assembly 12. The elongate shaft assembly 12 can be used to hold the prosthesis for advancement of the same through the vasculature to a treatment location. The delivery system 10 can further comprise a relatively rigid live-on sheath 51 surrounding the elongate shaft assembly 12 that can prevent unwanted motion of the elongate shaft assembly 12. The elongate shaft assembly 12 can include an implant retention area 16 (shown in FIGS. 2A-B with FIG. 2A showing the prosthesis 70 and FIG. 2B with the prosthesis 70 removed) at its distal end that can be used for this purpose. In some embodiments, the elongate shaft assembly 12 can hold an expandable prosthesis in a compressed state at implant retention area 16 for advancement of the prosthesis within the body. The elongate shaft assembly 12 may then be used to allow controlled expansion of the prosthesis at the treatment location. The implant retention area 16 is shown in FIGS. 2A-B at the distal end of the delivery system, but may also be at other locations. In some embodiments, the prosthesis 70 may be rotated in the implant retention area 16, such as through the rotation of the inner assembly 18 discussed herein.

As shown in cross-sectional view of FIGS. 2A-B, the elongate shaft assembly 12 can include one or more subassemblies such as an inner assembly 18, a mid shaft assembly 20, an outer sheath assembly 22, and nose cone assembly 31 as will be described in more detail below.

As shown, the outer sheath assembly 22 can form an radially outer covering, or sheath, to surround an implant retention area 16. Moving radially inward, the mid shaft assembly 20 can be composed of a mid shaft 50 with its distal end attached to outer retention member or outer retention ring 40. Moving further inwards, the inner assembly 18 can be composed of an inner retention shaft 42 and an inner retention member 32. Further, the most radially-inward assembly is the nose cone assembly 31 which includes the nose cone shaft 30 having its distal end connected to the nose cone 28.

The elongate shaft assembly 12, and more specifically the nose cone assembly 31, inner assembly 18, mid shaft assembly 20, and outer sheath assembly 22, can be configured to deliver a prosthesis 70 positioned within the implant retention area 16 (shown in FIG. 2A) to a treatment location. One or more of the subassemblies can then be moved to allow the prosthesis 70 to be released at the treatment location. For example, one or more of the subassemblies may be movable with respect to one or more of the other subassemblies. The handle 14 can include various control mechanisms that can be used to control the movement of the various subassemblies as will also be described in more detail below. In this way, the prosthesis 70 can be controllably loaded onto the delivery system 10 and then later deployed within the body.

Figure 3:
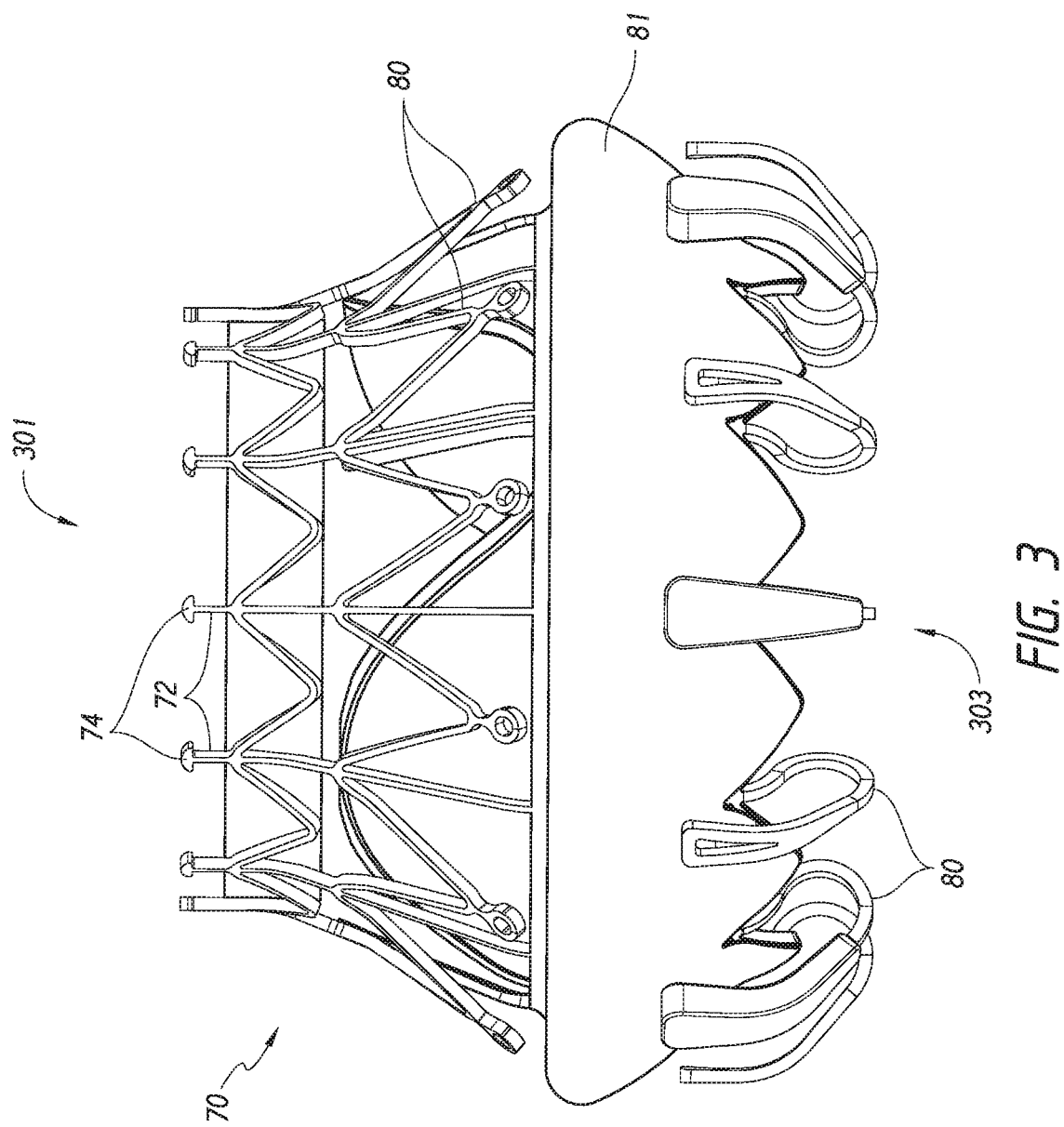
FIG. 3 shows a side view of an embodiment of a valve prosthesis that may be delivered using the delivery systems described herein.

FIG. 2A further shows an example of the prosthesis 70 that can be inserted into the delivery system 10, specifically into the implant retention area 16. For ease of understanding, in FIG. 2A, the prosthesis is shown with only the bare metal frame illustrated. The implant or prosthesis 70 can take any number of different forms. A particular example of frame for a prosthesis is shown in FIG. 3, though it will be understood that other designs can also be used. The prosthesis 70 can include one or more sets of anchors, such as distal (or ventricular) anchors 80 extending proximally when the prosthesis frame is in an expanded configuration and proximal (or atrial) anchors 82 extending distally when the prosthesis frame is in an expanded configuration. The prosthesis can further include struts 72 which may end in mushroom-shaped tabs 74 at the first end 301 as well as a flap 81 surrounding the frame near the second end 303. Further discussion on the annular flap 81 can be found in U.S. Pub. No. 2015/0328000, filed May 19, 2015, hereby incorporated by reference in its entirety.

Additional details and example designs for a prosthesis are described in U.S. Pat. Nos. 8,403,983, 8,414,644, 8,652,203 and U.S. Patent Publication Nos. 2011/0313515, 2012/0215303, 2014/0277390, 2014/0277422, 2014/0277427, the entirety of these patents and publications are hereby incorporated by reference and made a part of this specification. Further details and embodiments of a replacement heart valve or prosthesis and its method of implantation are described in U.S. patent application Ser. No. 14/716,507, filed May 19, 2015, and Ser. No. 15/141,684, filed Apr. 28, 2016 the entirety of each of which is hereby incorporated by reference and made a part of this specification.

As will be discussed below, the inner retention member 32, the outer retention ring 40 and the outer sheath assembly 22 can cooperate to hold the prosthesis 70 in a compacted configuration. The inner retention member 32 is shown engaging struts 72 at the proximal end of the prosthesis 70. For example, slots located between radially extending teeth on the inner retention member 32 can receive and engage the struts 72 which may end in mushroom-shaped tabs 74 on the proximal end of the prosthesis 70. The outer retention ring 40 can be positioned over the inner retention member 32 so that the first end 301 of the prosthesis 70 is trapped therebetween, securely attaching it to the delivery system 10.

As shown in FIG. 2A, the distal anchors 80 can be located in a delivered configuration where the distal anchors 80 point generally distally (as illustrated, axially away from the main body of the prosthesis frame and away from the handle of the delivery system). The distal anchors 80 can be restrained in this delivered configuration by the outer sheath assembly 22. Accordingly, when the outer sheath 22 is withdrawn proximally, the distal anchors 80 can flip positions to a deployed configuration (e.g., pointing generally proximally). FIG. 2A also shows the proximal anchors 82 extending distally in their delivered configuration within the outer sheath assembly 22 and within the outer retention ring 40. In other embodiments, the distal anchors 80 can be held to point generally proximally in the delivered configuration and compressed against the body of the prosthesis frame.

The delivery system 10 may be provided to users with a prosthesis 70 preinstalled. In other embodiments, the prosthesis 70 can be loaded onto the delivery system shortly before use, such as by a physician or nurse.

Figure 4:
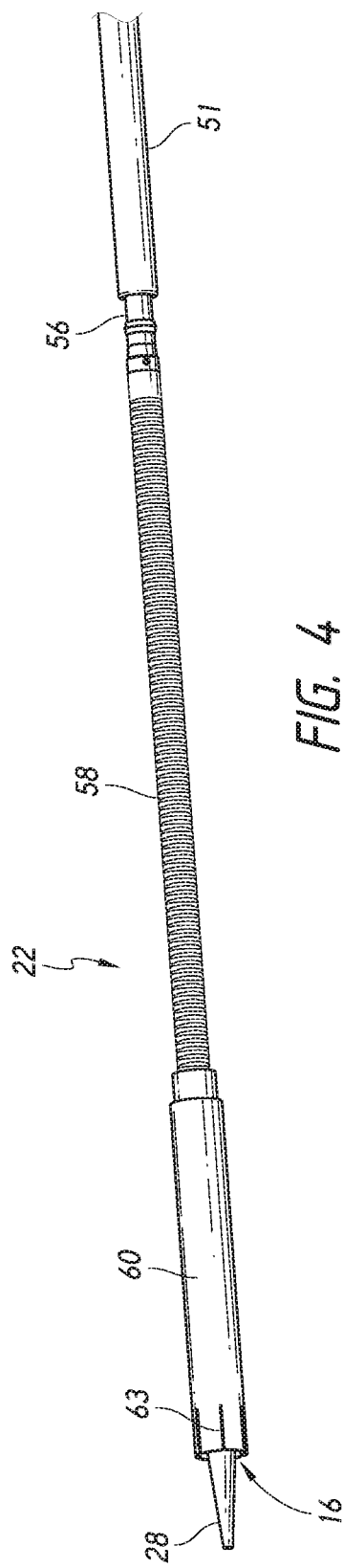
FIG. 4 shows a perspective view of the distal end of the delivery system of FIG. 1.
Figure 5:
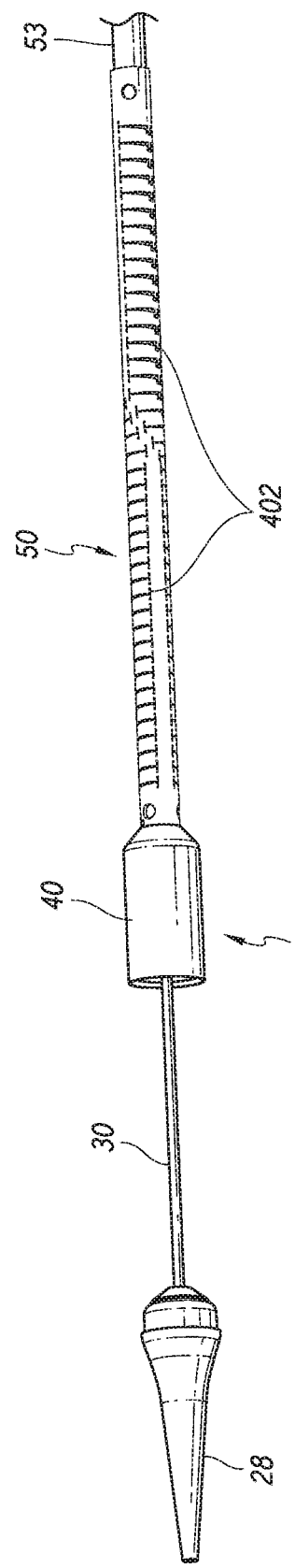
FIG. 5 show components of the delivery system of FIG. 4 with the outer sheath assembly moved proximally and out of view.
Figure 6:
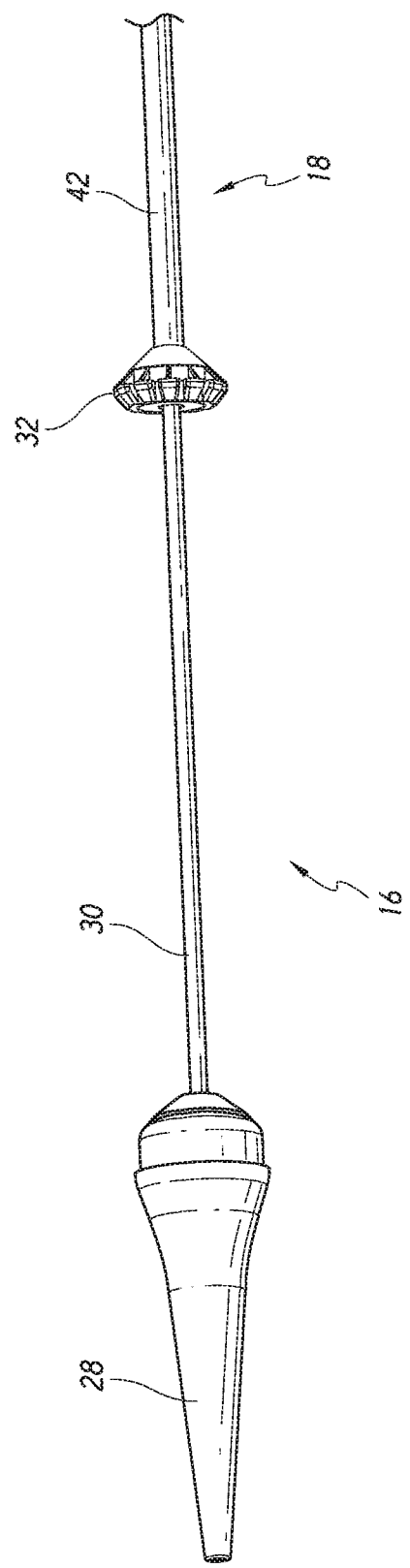
FIG. 6 show components of the delivery system of FIG. 5 with the mid shaft assembly moved proximally and out of view.

FIG. 4-6 illustrate further views of delivery system 10 with different assemblies translated proximally and described in detail.

The outer sheath assembly 22 will now be described, which is shown in FIG. 4. Specifically, FIG. 4 shows an outer sheath assembly 22 in its distal most position relative to nose cone 28. Further, as shown, a live-on sheath 51 can be used to cover the outer sheath assembly 22 and provide structural support during bending, though its use is optional. The outer sheath assembly 22 is disposed so as to be slidable over the inner assembly 18, the mid shaft assembly 20, and the nose cone assembly 31. Like the nose cone assembly 31, inner assembly 18 and the mid shaft assembly 20, the outer sheath assembly 22 can be a single piece tube or multiple pieces connected together to provide different characteristics along different sections of the tube. As has been mentioned, in some embodiments it can be desirable, and/or needful, for the delivery system 10 to have greater flexibility at the distal end of the device, where flexibility is not as necessary for the proximal end. The illustrated outer sheath assembly 22 has a first segment 56, a second segment 58, and a third segment 60, where the first segment 56 is proximal to the second segment 58, and the second segment 58 is proximal to the third segment 60. The third segment 60 of the outer sheath is shown in contact with the proximal end of the nose cone 28. In this position, a prosthesis 70 can be held within the outer shaft assembly 22 for advancement of the same through the vasculature to a treatment location. The first segment 56 may be a tube and is preferably formed plastic, but could also be a metal hypotube or other material. A further discussion of the first segment 56 is below with respect to FIGS. 10A-10D.

The second segment 58 can be a metal hypotube which in some embodiments may be cut or have slots. The tube 58 can be covered or encapsulated with a layer of ePTFE, PTFE, or other material so that the outer surface of the outer sheath assembly is generally smooth. The covered second segment 58 is shown in FIG. 4. The third segment 60 can be a tube formed of a plastic or metal material. In a preferred embodiment, the third segment is formed of ePTFE or PTFE. In some embodiments this sheathing material can be relatively thick to prevent tearing and to help maintain a self-expanding implant in a compacted configuration. In some embodiments the material of the third segment 60 is the same material as the coating on the cut hypotube 1058. The full construction of the second segment 58 and third segment 60 are discussed in detail below with respect to FIGS. 11A-E.

In some embodiments the third segment 60 can include one or more wings or tabs 63, shown in FIG. 4, extending distally from a distal end of the third segment 60. The tabs 63 can be configured to bend, curve, or fold radially outward from the third segment 60. The one or more tabs 63 can facilitate loading of a replacement valve within the third segment 60 when the replacement valve is initially loaded into the delivery system 10. In some embodiments, the one or more tabs 63 can be removed prior to use within a patient, such as shown in FIG. 10 of U.S. Provisional App. No. 62/210,165 filed Aug. 26, 2015. The one or more tabs 63 can be formed by cutting the third segment 60 via methods including, but not limited to, laser cutting.

FIG. 5 illustrates the system 10 with the outer sheath assembly 22 removed (e.g., by pulling the outer sheath assembly 22 proximally), thus partially exposing the mid shaft assembly 20 including a portion of or all of a prosthesis (not shown) in the implant retention area 16. Like the nose cone assembly 31, inner assembly 18, and outer sheath assembly 22, the mid shaft assembly 20 can be a single piece tube or multiple pieces connected together to provide different characteristics along different sections of the tube. As has been mentioned, in some embodiments it can be desirable, and/or needful, for the delivery system 10 to have greater flexibility at the distal end of the device, where flexibility is not as necessary for the proximal end. The illustrated mid shaft assembly 20 has a first segment 53, a second segment or mid shaft 50 distal to the first segment, and a third segment 40 distal the mid-shaft 50 being the outer retention ring 40. The first segment can extend distally away from the handle and be connected to the second segment or mid shaft 50 at the distal end of the first segment. As shown in FIG. 5, the distal end of the second segment 50 can attach to the outer retention ring 40 (e.g., third segment). Each of the segments can be a tube, for example a metal or polymer tube, such as described with respect to the outer sheath assembly 22. Further discussion of the mid shaft 50 construction can be found below with respect to FIGS. 7-8.

Through the use of the handle 14, the mid shaft assembly 20 can translate or slide over the inner assembly 18, which thereby causes the outer retention ring 40 to slide over the inner assembly 18 and encircle the inner retention member 32 described below. As shown in FIG. 2A, the outer retention ring 40 encircles a portion of the prosthesis 70, in particular the proximal portion, thus preventing the prosthesis 70 from expanding. The outer retention ring 40 can also circumferentially surround the inner retention member 32. Further, the mid shaft assembly 20 can be translated proximally with respect to the inner assembly 18 into the proximally-retracted outer sheath assembly 22, thus exposing a proximal portion of the prosthesis 70 held within the outer retention ring 40. A taper 61 may be provided at the proximal end of the outer retention ring 40 to allow it to more easily slide into the outer sheath assembly 22. In this way the outer retention ring 40 can be used to help secure a prosthesis to or release it from the delivery system 10. The outer retention ring 40 can have a cylindrical or elongate tubular shape.

Further, as shown in FIG. 2A, the outer retention ring 40 can cover a substantial length of the prosthesis 70. For example, the outer retention ring 40 can cover over ⅛, ¼, ⅓, or ½ of the prosthesis 70. In addition, the outer retention ring 40 can cover a substantial length of the atrial anchors 82. For example, the outer retention ring 40 can cover over 75%, over 80%, over 85%, or over 90% of the atrial anchors 82. The outer retention ring 40 can be about 15, 17, 17, 18, 19, or 20 mm in length or a range between those lengths. In some embodiments, the outer retention ring 40 can be between about 10 and about 30 mm in length.

FIG. 6 shows approximately the same view as FIG. 5, but with the mid shaft assembly 20, including the outer retention ring 40 and mid shaft 50, removed, thereby partially exposing the inner assembly 18 (including the inner retention member 32 attached to inner retention shaft 42) and nose cone assembly 31 (including the nose cone shaft 30 attached to the nose cone 28).

As mentioned the inner assembly 18 can be composed of the inner retention shaft 42 with the inner retention member 32 attached to the distal end of the inner retention shaft 42. Similar to the assemblies above, the inner retention shaft 42 can comprise a tube, such as a hypodermic tube or hypotube (not shown). The tube can be made from one of any number of different materials including nitinol, stainless steel, and medical grade plastics. The tube can be a single piece tube or multiple pieces connected together. Using a tube made of multiple pieces can allow the tube to provide different characteristics along different sections of the tube, such as rigidity and flexibility.

In some embodiments a first segment (now shown) of the inner assembly 18 can be made of a hypotube can extend along a majority of the length of the inner assembly 18. For example, metal hypotube extends from within the handle 16 at the proximal end towards the distal end up until a second segment (or inner retention shaft) 42 of the inner assembly 18 before the implant retention area 16. The hypotube can provide column strength (pushability) to the inner assembly. Further, the handle 16 can allow for rotation of the second segment 42, which can allow for rotation of the prosthesis 70. A second segment 42 of the inner assembly 18 can be made of a more flexible material. For example, the second segment 42 can comprise a wire such as a multi-stranded wire, wire rope, or wire coil. The wire can surround a more flexible tube, such as a plastic tube, or it may be formed as a tube without any additional inner materials or core. Thus, in some embodiments, the wire can be a hollow core wire rope. The wire can provide the inner assembly 18 with strength, but it can also provide more flexibility to allow for navigating the curvosities of the vasculature, such as within the heart.

The inner assembly 18 can also include a prosthesis retention mechanism such as an inner retention member 32 at a distal end of the second segment 42 that can be used to engage with the prosthesis, as discussed with respect to FIG. 2A. For example, the inner retention member 32 may be a ring and can include a plurality of slots configured to engage with struts 72 on the prosthesis 70. The inner retention member 32 can also be considered to be part of the implant retention area 16, and may be at the proximal end of the implant retention area 16. With struts or other parts of a prosthesis 70 engaged with the inner retention member 32, an outer retention member such as outer retention ring 40 can cover both the prosthesis and the inner retention member 32 to secure the prosthesis on the delivery system 10.

Further, as shown in FIG. 6, the nose cone assembly 31 may be an elongate member, and in some embodiments, may have a nose cone 28 on its distal end. The nose cone 28 can be made of polyurethane for atraumatic entry and to minimize injury to venous vasculature. The nose cone 28 can also be radiopaque to provide for visibility under fluoroscopy.

The nose cone shaft 30 may include a lumen sized and configured to slidably accommodate a guide wire so that the delivery system 10 can be advanced over the guide wire through the vasculature. However, embodiments of the system 10 discussed herein may not use a guide wire and thus the nose cone shaft 30 can be solid. The nose cone shaft 30 may be connected from the nose cone 28 to the handle, or may be formed of different segments such as the other assemblies. Further, the nose cone shaft 30 can be formed of different materials, such as plastic or metal, similar to those described in detail above.

This view also illustrates that the nose cone shaft 36 can be slidably disposed within the inner assembly 18, thus allowing the nose cone shaft 28 (and thus nose cone 28) and the inner retention member 32 to move separately from one another during deployment and use.

The inner retention member 32 and outer retention ring 40 and the delivery system 10 generally may be similar to those disclosed in U.S. Pat. Nos. 8,414,644 and 8,652,203, the entire contents of both of which are hereby incorporated by reference herein and made a part of this specification. This is inclusive of the entire disclosure, including other apparatuses and methods described therein, and is not in any way limited to the disclosure of the inner and outer retentions and/or the delivery system.

Steerable Mid Shaft Construction

Advantageously, embodiments of the system 10 can be configured to be flexible when located in a patient and can allow for steering of the system 10 in a particular direction as desired by a user. In particular, in a transfemoral approach to the mitral valve, embodiments of the system 10 can provide for controlled steerability to allow a user to better navigate and turn the distal end of the system 10 from the septum between the left and right atrial and into the native mitral valve annulus. In some embodiments, no guide wire is required to steer the system 10. Although particular shaft constructions are described below with respect to the mid shaft assembly 20, it will be appreciated that these constructions may be applied to other components as well.

As mentioned, FIG. 5 illustrates an embodiment of the second segment (e.g., mid shaft) 50 of the mid shaft assembly 20. As shown in FIG. 5, the mid shaft 50 can be formed from a tube that comprises a series of discrete slots 402 that can be located along the length of the mid shaft 50. The slots 402 can be oriented substantially perpendicular to a longitudinal axis of the mid shaft 50, with each slot having a proximal side, a distal side, and two circumferentially spaced apart opposite ends. The slots 402 in the mid shaft 50 rotate partially circumferentially around the mid shaft 50. The slots 402 can form a gap configured to close upon application of a force which, in this particular slot configuration allows the mid shaft 50 to steer as guided by the configuration of the slots 402, such as described below. By varying the characteristics of the slots 402, different bending characteristics of the mid shaft 50 can occur.

Figure 7:
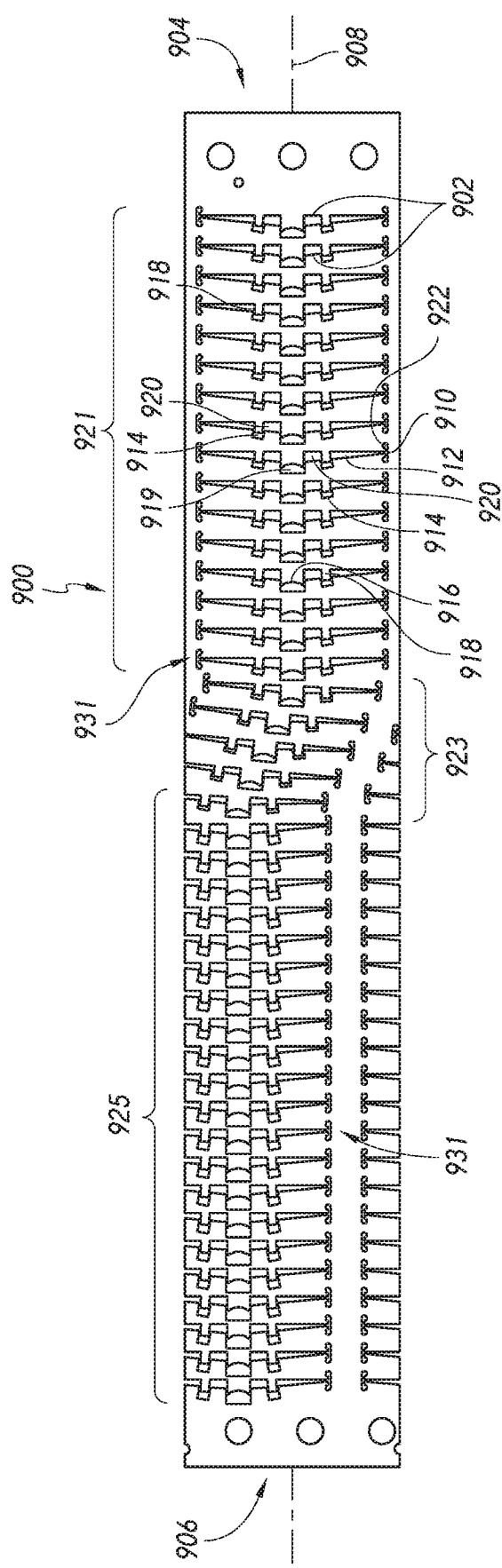
FIG. 7 illustrates a flat pattern of an embodiment of the mid shaft.

FIG. 7 shows a flat pattern 900 of the mid shaft 50 shown in FIG. 5, where the flat pattern illustrates how the tube forming the mid shaft 50 is cut if the tube were to be longitudinally cut along its length to form slots 902 and laid flat. The tube formed from the flat pattern 900, as well as the other flat patterns discussed below, can be formed by seamless drawn tubing where slots are laser cut into the tube. When in a tube form, a spine 931 can be formed along its length between the ends of each slots 902. For example, the mid shaft 50 may be made of a laser cut metal tube, where the tube has a flat pattern 900 as illustrated in FIG. 7. As shown, the flat pattern 900 can have a series of slots 902, in some embodiments greater than 40 slots 902, along its length from the proximal end 904 to the distal end 906. The slots 902 may be discrete slots, each spaced apart longitudinally from each other. While FIG. 7 shows slots 902 that are approximately equally spaced longitudinally from each other, other embodiments may include slots that have varying spacing there between. Slots 902 may be provided along substantially the entire length of the tube as illustrated, or may be provided only in portions along the length of the tube.

The flat pattern 900 can be considered to include a center line 908 extending longitudinally from the proximal end to the distal end, with the slots 902 oriented perpendicular or substantially perpendicular to the center line. In other words, the slots 902 may be oriented perpendicular or substantially perpendicular to a longitudinal axis of the mid shaft 50, and may extend or rotate circumferentially around the mid shaft 50. Slots 902 can rotate circumferentially around the flat pattern 900 in the tubular form almost the entirety of the mid shaft 50, for example over 80, 100, 120, 170, 180, 200, 220, 280, 300, 320, or 340 degrees circumferentially, leaving a small gap between lateral ends of each slot.

Some of the slots 902, for example those closer to the proximal end 904 of the tube (herein referred to as proximal slots 921), may have the same circumferential position over a portion of the length of the tube (here the proximal slot section). As illustrated, there are 16 proximal slots 921 which may be identical to each other, each having a center portion located on the center line 908 and extending transversely from the center line 908 in a symmetrical pattern about the center line 908 (e.g., parallel to the longitudinal axis of the mid shaft 50). Distal to the proximal slots 921 are a plurality of transition slots 923 similar in shape to the proximal slots 921, but having center portions that gradually move transversely further away from the center line 908 so that the transition slots 923 are angled relative to the center line 908. As illustrated, there may be 5 such transition slots 923. Whereas the proximal slots 921 are oriented perpendicular or substantially perpendicular to the longitudinal axis of the shaft 50, the transition slots 923 are slightly angled relative to proximal slots 921.

Distal to the transition slots 923 are a plurality of distal slots 925 in a distal slot section, for example 21 distal slots 925, which may have the same circumferential position over a proximal portion of the tube. The distal slots 925 may be identical to each other. The distal slots 925 may also be identical to the proximal slots 921. The distal slots 925 may each have a center portion that is circumferentially offset from the center portions of the proximal slots 921, and may continue longitudinally along the length of the tube from the proximalmost transition slot. Like the proximal slots 921, the distal slots 925 may be oriented perpendicular or substantially perpendicular to the longitudinal axis of the shaft 50 and the center line 908.

It will therefore be appreciated that the slots 902 can be located at different circumferential positions along the length of the flat pattern 900. For example, the center portions of the distal slots 925 and the center portions of the proximal slots 921 can be about 0-180° apart, preferably from about 45° to about 90°. Other circumferential changes, such as, for example, 10, 20, 30, 40, 45, 50, 60, 70, 80, or 90° could be used as well. A majority of the slots 902 can be the proximal slots 921 and the distal slots 925, with only a small number of transition slots 923 between the two locations. Further, approximately half or more of the slots 902 can be proximal slots, though in other embodiments the number of slots 902 in these positions can change. Further, as shown in FIG. 7, the spine 931 will rotate along a circumference of the tube as well. The spine 932 will extend linearly along the proximal slots 921, turn at an angle to follow the transition slots 923, and again extend linearly along the distal slots 925.

The slots 902 themselves can be generally identical throughout the length of the mid shaft 50, though there may be some minor variations. This can allow the proximal end 904 to generally always be activated (e.g., at least some slight bending) during application of a force at the distal end 906. Each individual slot 902 as illustrated in FIG. 7 has a width (as measured circumferentially or transverse to the longitudinal axis of the mid shaft 50) which is much greater than its length (as measured along the longitudinal axis of the mid shaft 50). Each slot 902 forms three teeth which extend toward the distal end 906 of the mid shaft 50, with a larger tooth 916 located in the center of the slot 902 and two smaller teeth 918 symmetrically located on opposite sides of the larger tooth 916 extending at a slight angle away from the center line 908. Distal to each tooth, the slot 902 forms a center gap 919 and two side gaps 914 that the teeth move distally into when the mid shaft 50 is longitudinally compressed. Between the larger tooth 916 and the two side teeth 918 are gaps 920 and circumferentially outward from the smaller side teeth are triangular shaped gaps 912. At the lateral ends of each slot there is a W-shaped slot 910 which defines in part end gaps 922 having a greater length than the small end of the triangular slots 912. More generally, the ends of the slots 902 may be considered to be T-shaped, which can distribute strain evenly on the edge of the slots 902 and allow the mid shaft 50 to return to its original position after bending. All portions of each slot 902 can be connected as a single slot, or can be broken into a number of different pieces.

The slot patterns described herein advantageously provide for a desired deformation of the slots 902 and therefore the mid shaft 50 as a force is applied to the mid shaft 50. For example, using the pull wire(s) as described below, a proximal force applied to a distal end of the mid shaft 50 will bend or steer the mid shaft 50 in a direction aligned with the slots 902, thereby closing the slots and bending the mid shaft 50 in the direction of the closure. Thus, when a force is applied, the mid shaft 50 can bend in more than one dimension to follow the closure of the slots 902, allowing 3-dimensional bending (and thus 3-dimensional steering) in part due to the transition slots 923. Moreover, the bending in the proximal and distal sections can occur simultaneously or in a two-part manner, depending on the size of the slots 902 and/or the strength of the force applied to the mid shaft 50. Typically, when a pulling force is applied to the distal end of the mid shaft, the proximal section having proximal slots 921 will experience the bending first, following by the transition section having transition slots 923, followed by the distal section having distal slots 925. However, in some embodiments, the above referenced live-on sheath 51 can at least partially surround the proximal section and can stiffen the proximal section during delivery. For example, when crossing a native mitral valve annulus from a transseptal access location, the live-on sheath may at least partially cover the proximal section, providing an outer wall barrier to prevent bending of the proximal section and proximal slots 921, because it can be advantageous for the distal section and distal slots 925 to provide more guiding during implantation than the proximal slots 921. Specifically, the further the distance from the distal end 906, the greater the moment generated by each pound of pull, causing the proximal end 904 to bend first, followed by the distal end 906. Thus, a user can better control the articulation of the mid shaft 50. However, it is advantageous for the proximal slots 921 to be activated by the least force because it can then always be activated during bending, thus providing stability for fine tuning the distal section 925 and providing torque to the entire delivery system 10 for additional positioning.

Figure 8A:
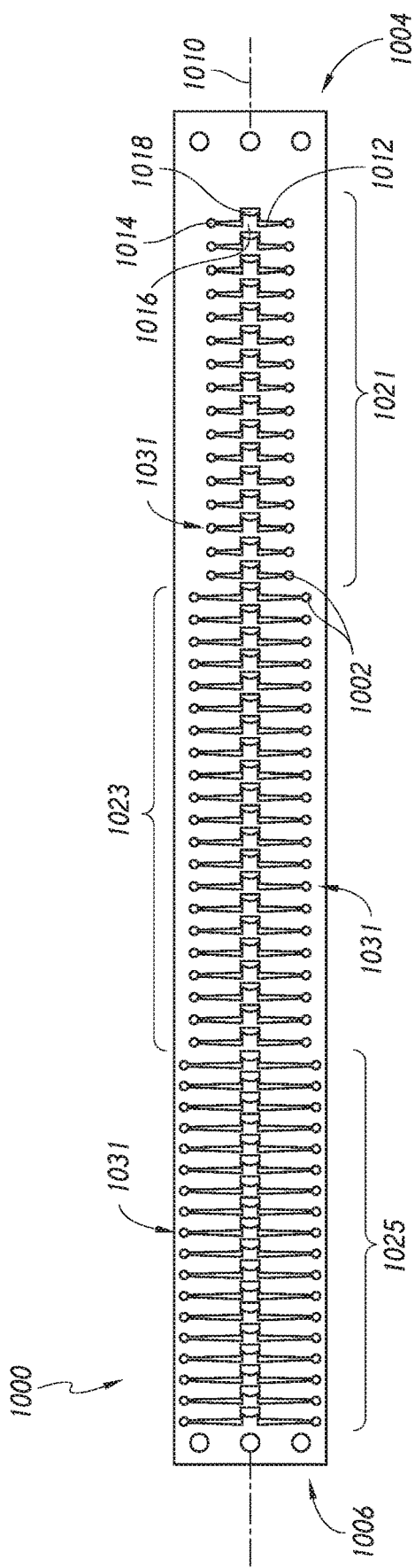
FIGS. 8A-B illustrate flat patterns of alternate embodiments of the mid shaft.
Figure 8B:
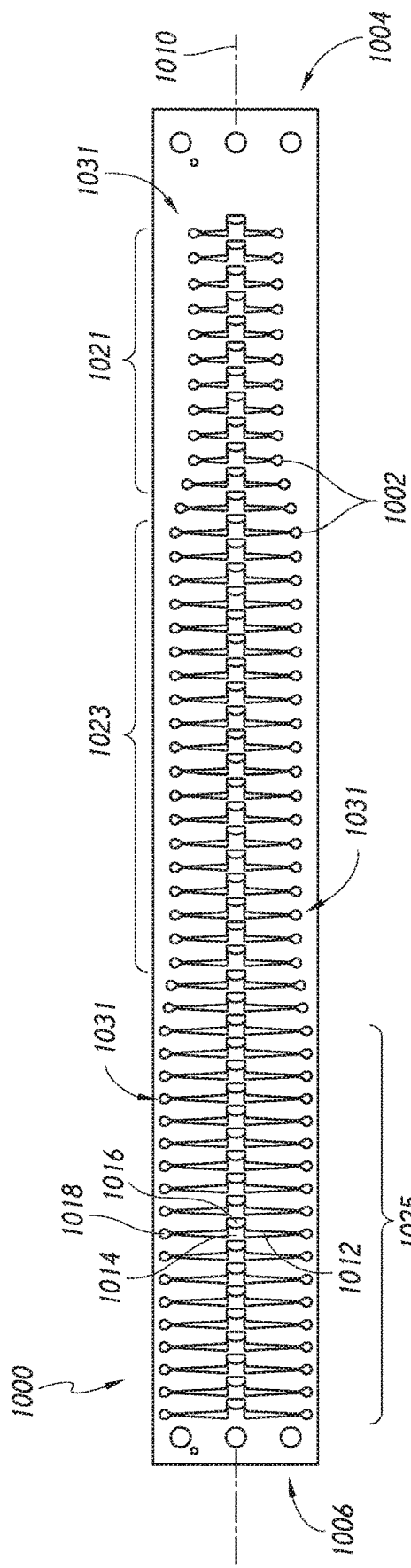

FIGS. 8A-B show alternate embodiments of a flat pattern 1000 for mid shaft 50. As shown, the series of slots 1002 can extend generally linearly over the entire length of the mid shaft 50, extending from the proximal end 1004 to the distal end 1006, where the centers of the slots 1002 remain parallel to the longitudinal axis. Further, when in a tube form, a spine 1031 can be formed along its length between the ends of each slots 1002. Thus, unlike the flat pattern 900 shown in FIG. 7, the flat pattern 1000 of FIGS. 8A-8B will generally have a single plane of motion, which will be generally aligned with the center 1010 of the slots 1002. Accordingly, when a force is applied, as discussed below, the flat pattern 1000 will bend along the plane formed by the center 1010, allowing for a two-dimensional movement. While FIGS.

8A-B shows slots 1002 that are approximately equally spaced longitudinally from each other, other embodiments may include slots that have varying spacing there between. Slots 1002 may be provided along substantially the entire length of the tube as illustrated, or may be provided only in portions along the length of the tube.

The flat pattern 1000 can be considered to include a center line 1010 extending longitudinally from the proximal end 1004 to the distal end 1006, with the slots 1002 oriented perpendicular or substantially perpendicular to the center line. In other words, the slots 1002 may be oriented perpendicular or substantially perpendicular to a longitudinal axis of the mid shaft 50, and may extend or rotate circumferentially around the mid shaft 50.

Further, as shown in FIG. 8A-B the slots can change in dimensions from the proximal end 1004 to the distal end 1006. This can allow for different articulation of the mid shaft 50 at different portions, creating a staged effect so that different sections of the mid shaft 50 bend at different times. Specifically, the further the distance from the distal end 1006, the greater the moment generated by each pound of pull, causing the proximal end 1004 to bend first, followed by the distal end 1006. Thus, a user can better control the articulation of the mid shaft 50.

Some of the slots 1002, for example those closer to the proximal end of the tube (herein referred to as the proximal slot section or proximal slots 1021), may be smaller over a portion of the length of the tube. As illustrated in FIG. 8A, there are 16 proximal slots 1021 which may be identical to each other, each having a center portion located on the center line 1010 and extending transversely from the center line 1010 in a symmetrical pattern about the center line 1010. Distal to the proximal slots 1021 are a plurality of middle slots 1023 (or a middle slot section) having a larger width than the proximal slots 1021 but remaining centered on center line 1010. As illustrated, there may be 21 such middle slots 1023.

Distal to the middle slots 1023 are a plurality of distal slots 1025 (or a distal slot section), for example 18 distal slots 1025, which have a greater width than the middle slots 1023 and proximal slots 1021. The distal slots 1025 may be identical to each other. The distal slots 1025 may each be centered on center line 1010, and may continue longitudinally along the length of the tube from the distalmost middle slot 1023. FIG. 8B has a similar configuration to FIG. 8A, but there are transition sections between the proximal slot section and the middle slot section, and between the middle slot section and the distal slot section. In these transition sections, there are slots that gradually increase in width from the more proximal slot section to the more distal slot section. The spine 1031 will thus extend linearly parallel to center line 1010 but will increase in width from the proximal slots 1021 to the middle slots 1023 and further increase in width from the middle slots 1023 to the distal slots 1025.

The decrease in slot width from the distal end 1006 to the proximal end 1004 can allow the mid shaft 50 to bend at the distal end 1006 prior to the proximal end 1004. Specifically, typically the higher the moment (e.g., force×distance from the force), the quicker the specific area will bend/deflect. In the mid shaft 50, the force is located at the distal end 1006, and thus the highest moment will be experienced at the proximal end 1004 as it is the farthest distance from the force. However, by having distal slots 1025 be larger than the proximal slots 1021, and thus the spine 1031 around the distal slots 1025 is smaller than around the proximal slots 1021, the distal end 1006 will bend first as there is significantly less material to bend and thus a lower moment is needed to bend, even though the distance from the force is the smallest. Further, having the transition slots 1023 with a width between the width of the distal slots 1025 and the width of the proximal slots 1021, thus creating a generally gradual change in width, can provide stress relief that would otherwise concentrate near the proximal end 1004.

The slots 1002 themselves can be generally identical in shape throughout the length of the mid shaft 50, though the dimensions (e.g., width) of the slots 1002 can vary. Each individual slot 1002 as illustrated in FIGS. 8A-B has a width (as measured circumferentially or transverse to the longitudinal axis of the mid shaft 50) which is much greater than its length. Each slot 1002 forms a single tooth 1016 which extend toward the proximal end 1004 of the mid shaft 50 and is located generally centered on longitudinal center line 1010. Proximal to the tooth 1016, the slot 1002 forms a center gap 1018 the tooth 1016 can move proximally into when the mid shaft 50 is longitudinally compressed. At the lateral ends of each slot there is a circular slot 1014 which defines in part end gaps having a greater length than the small end of a triangular slot 1012 located between the circular slot 1014 and the center gap 1018. All portions of each slot 1002 can be connected as a single slot, or can be broken into a number of different pieces.

Further, the flat pattern 1000 shown in FIGS. 8A-B can also allow for an organic compound bend. While the embodiment shown in FIGS. 8A-B generally only bends on a single plane, the mid shaft 50 can be configured to provide for slight bending outside of the plane, which can be used to properly place the implant 70 in a patient. Specifically, as the mid shaft 50 steers in the direction by a user, there can be a bending outside of the two dimensional plane. For example, there is space on the circumferential sides of the tooth 1016 for the tooth 1016 to move laterally, which gives some lateral flexibility (e.g., outside of the single plane of motion) when the mid shaft 50 impacts a portion of a patient's anatomy. Over the course of the entire mid shaft 50, the slight amount of lateral motion can provide for motion similar to that of the flat pattern 900 shown in FIG. 7. Therefore, the flat pattern 1000 can allow for a more forgiving pattern which can conform to the particular anatomy of a patient while the flat pattern 900 of FIG. 7 is more repeatable and provides for greater control as it does not conform to the anatomy.

Figure 9:
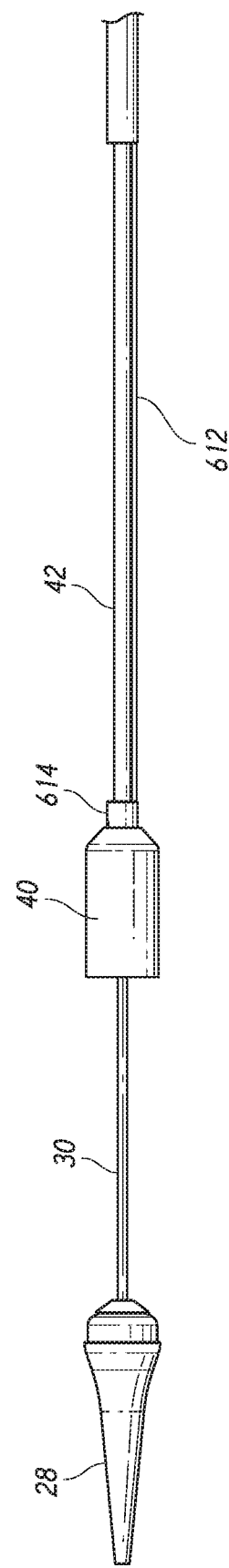
FIG. 9 shows the pull wire position at the distal end of the delivery system of FIG. 1.

Described next is the construction for enacting a force and thus causing the bending of the above disclosed mid shafts 50 having flat patterns as described above. As shown in FIG. 9, which has the outer sheath assembly 22 and mid shaft assembly 20 other than the outer retention ring 40 removed, a pull wire 612 (such as a 0.018 inch diameter pull wire) can be used to connect the outer retention ring 40 to the handle 14. The handle 14 can have a steering knob/actuator 610 (shown in FIG. 1) in order to apply a force and control the bending of the mid shaft 50. In some embodiments, the pull wire 612 can be connected to the nose cone 28, thereby providing a steering point more distal than the outer retention ring 40.

Further, the steering knob 610 can compensate for foreshortening of the delivery system 10 during bending. As the different components of the delivery system 10 bend (for example, the mid shaft bending to close slots 402 or the hypotube 150 of the outer sheath assembly 22 bending to close slots 152 described below), the mid shaft 50 and the outer sheath assembly 22 will reduce in length due to the closure of the slots, which could cause accidental release of prosthesis 70. Thus, the steering knob 610 can be configured to move the outer sheath assembly 22 distally during activation of the steering knob 610, while simultaneously pulling on the pull wire 612. This can prevent unwanted relative motion of the components of the delivery system 10 or unbalanced forces, in particular unwanted release of the prosthesis 70.

The steering knob 610 in the handle 14 can be connected to a pull wire 612 generally at the proximal end of the system 10. The pull wire 612 can extend through the lumen of the mid shaft 50 and on the outside of the inner assembly 18. The pull wire 612 can connect to the outer retention ring connecter 614 which connects the distal portion of the mid shaft 50 to the outer retention ring 40. Specifically, the outer retention ring connecter 614 can act as a weld spot for the pull wire 612 through, for example, a groove in the outer retention ring connector 614. The outer retention ring connector 614 can be connected to the mid shaft 50 by a series of rivets, though the attachment mechanism is not limiting.

The pull wire 612 can be connected to the handle 14 through a proximal wire connector 1200 shown in FIGS. 12A-12B having a proximal end 1202 and a distal end 1204. The proximal wire connector 1200 has a generally tubular shape which can be located/attached within a housing of the handle 14. The proximal wire connector 1200 can have a length of about 0.50 inches. The pull wire 612 can extend through an aperture 1212 forming a longitudinal lumen along a length of the proximal wire connector 1200 at a distal end 1204. As shown, pull wire 612 can attach within the longitudinal lumen radially inward from a generally tear-drop shaped groove 1206 having a larger end 1208 nearest the proximal end 1202 and a smaller end 1210 near the distal end 1204. The groove 1206 can extend through a radius of the proximal wire connector 1200 to meet with the longitudinal lumen. The larger end 1208 can have a radius of curvature of about 0.250 inches and the smaller end 1210 can have a radius of curvature of about 0.0050 inches.

The pull wire 612 can then be welded in place in the longitudinal lumen radially inward from the larger end 1208. The tear-drop shaped groove 1206 is advantageous as the amount of heat the pull wire 612 is exposed to during welding decreases from the proximal end 1202 to the distal end 1204 as more mass is present neared the distal end 1204. Thus, the weld can be more consistent and less prone to issues caused by any heat-affected-zone during welding. Further, whereas most welding occurs at a 20% loss, the tear-shaped groove 1206 allows for about 5% loss or less.

A user can thus manipulate the steering knob 610 to provide or relax a proximal force on the pull wire 612. Specifically, the proximal wire connector 1200 can be placed in a channel in handle 14 that narrows at one point distal to the proximal wire connector 1200. The channel can be pulled proximally by the steering knob 610 and once the proximal wire connector 1200 abuts the narrowed portion of the channel on its distal end, the proximal wire connector 1200 (and thus the pull wire 612) will be pulled proximally along with the channel, creating a proximal force on the pull wire 612. As proximal force is enacted onto the pull wire 612, the mid shaft 50 will bend in the direction of the slot openings. The slot pattern on the mid shaft 50 will cause the mid shaft 50 to bend along the direction of the slots 402 with the enactment of the pull wire 612 force. As mentioned above, in the embodiment shown in FIG. 7, the mid shaft 50 can bend in at least two directions, thus giving the device 10 3-dimensional steerability. The disclosed method is advantageous as the pull wire 612 will not be put under compression, which could lead to kinking.

As the force on the pull wire 612 is removed, the mid shaft 50 can translate back (e.g., "spring back") to its original position. This can occur at least partially due to the material (e.g., nitinol) and partially due to the construction of the ends of slots 902, which are generally T-shaped. This can be advantageous because, as discussed below, the pull wire 612 will not be compressed, thus avoiding kinks. In some embodiments, the mid shaft 50 will remain in the bent configuration even upon removal of the force. In some alternate embodiments, a second pull wire can be used, located in a different portion of the mid shaft 50. For example, the second pull wire can located 90° or 180° from the pull wire 612, thus allowing for two-way steering of the mid shaft 50. A user can operate both pull wires independently, or they can operate in tandem with one another to produce the desired bend in the mid shaft 50.

Outer Sheath Assembly Construction

As mentioned above, the outer sheath assembly 22 can be composed of a number of different parts, namely a first segment 56 a second segment 58, and a third segment 60. These different segments can have different features, builds, or constructions allowing for the segments to have properties advantageous to that particular section.

Starting at the proximalmost portion of the outer sheath assembly 22 is first segment 56 which can be in the tube of a form having a lumen throughout its length. FIGS. 10A-10D illustrate the first segment 56 in an unrolled configuration, or a flat pattern for the tube. This segment 56 can be formed from laser cut stainless steel, though the particular material or method of cutting is not limiting.

As shown in the figures, the first segment can be formed from a series of transverse and longitudinal slot pairs 710, which are designed to transmit torque (e.g., rotating the delivery system 10 clockwise/counter-clockwise) while being flexible. The delivery system 10 can be rotated anywhere between 0 to 180° to reposition the prosthesis 70. Each slot of the slot pairs 710 can be composed of a shorter longitudinal slot 712 and a longer circumferential slot 714 with its end connected approximately at the middle of the longitudinal slot 712. The circumferential slot 714 can be slightly on angle from the longitudinal slot 712 and thus not perpendicular to the longitudinal axis. Thus each of the slot pairs 710 can form a generally T-shaped pattern. This T-shape will allow the first segment 56 to translate back to its original position as the T-shaped pattern can distribute strain more evenly. As shown in FIGS. 10A-10D the slot patterns can be formed with circumferential slots 714 of each slot pair generally overlapping one another circumferentially and spaced apart in the longitudinal direction. The longitudinal slots 712 of the pair 710 can then be located on circumferentially opposite sides of circumferential slots 714 so that they can each longitudinally overlap both of the longitudinal slots 712. These slot pairs 710 can then be repeated around the circumference of the first segment 56 to form slot rings 716. The pairs 710 can be spaced apart on the slot rings 714 to provide for tensile strength.

Further, the slot rings 714 can be repeated along the length of the first segment 56, wherein they can be repeated at a length of about 0.251 inches. The slot rings 716 can extend along approximately 38.251 inches of the first segment 56. In some embodiments, the slot rings 716 are not found in a portion at the beginning and end of the first segment 56. This portion can be about 0.719 inches in length. Any number of slot rings 716 can be used, and the number of slot rings 716 is not limiting.

The longitudinal slots 712 can have a length of about 0.5, 0.6, 0.61, 0.7, or 0.8 inches, though the particular length is not limiting. Further, the longitudinal slots 712 can have a width of about 0.0005, 0.001, 0.0015, or 0.0002 inches. Longitudinal slots 712 of the slot pairs 712 can be spaced about 0.302 inches apart.

On the other hand, the circumferential slots 714 can have a width (as measured circumferentially or transverse to the longitudinal axis of the mid shaft 50) of about 0.2765 inches. In some embodiments, the circumferential slots 714 can have a width that increases in thickness, wherein the thickness portion of the circumferential slots 714 can be located in the middle of the circumferential slots 714, thus forming an extended ovaloid shape. This ovaloid can have a radius of about 1.881 inches. For example, the thickness of the circumferential slots 714 can transition from approximately 0.001 inches at the beginning and end of the circumferential slots 714 to about approximately double in thickness. Circumferential slots 714 of the slot pairs 710 can have an overlap of approximately 0.251 inches. They can be spaced apart by approximately 0.026 inches.

Figure 10C:
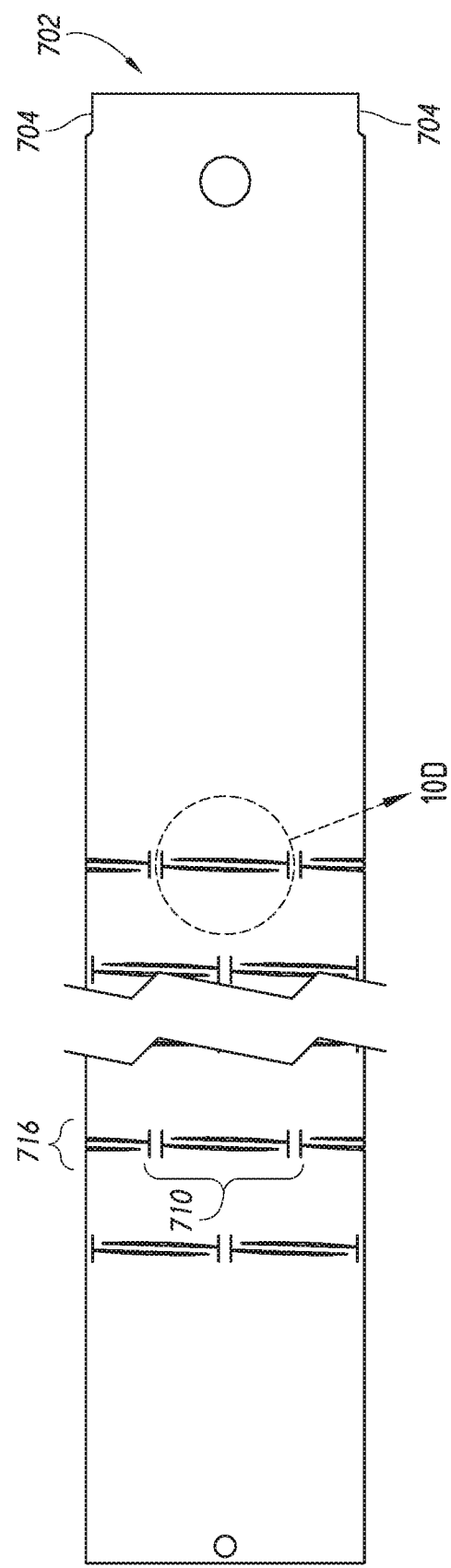
Figure 10D:
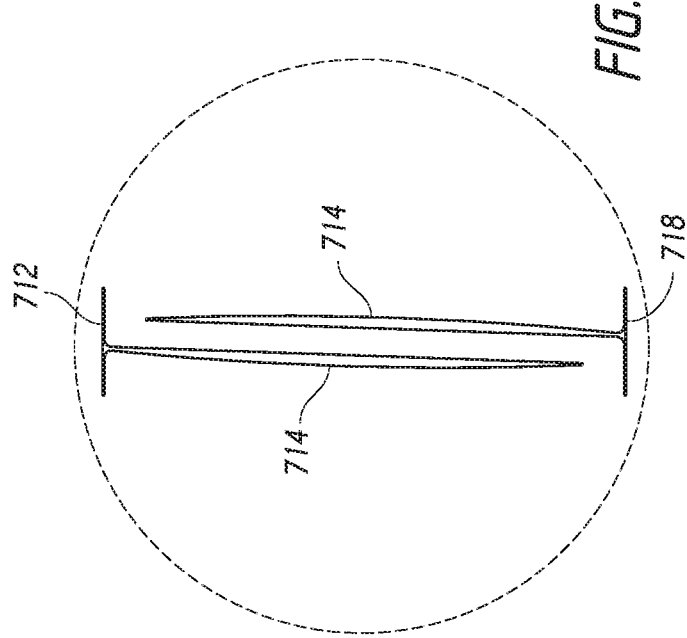

As shown, FIG. 10A has a proximal end 702 that is generally flat, whereas FIG. 10C shows a proximal end 702 which has a pair of notches 704 which can help align the part with the handle 14, for example providing an audible or tactile "click" when installed properly.

Advantageously, embodiments of the disclosed slot configuration can maintain strength and torque-transmission of, for example, stainless steel, while providing new flexibility. The configuration can handle compression, tension, and torque transmission with nearly 1:1 with no stretching. For example, a knob on the handle 14 can translate the outer sheath assembly 22 wherein every inch of turning of the knob results in an inch of translation of the outer sheath assembly 22, hence the 1:1 ratio. This is advantageous over other types of shafts, such as those formed of PEBAX, which would act like a rubber band where a user would see no response for an inch of travel of the knob as the PEBAX would stretch the whole time, and a user would be unsure when the translation would reach the distal end. The distal end would then translate suddenly and with no control, which could cause serious problems in a patient. Further, embodiments of the disclosed outer sheath assembly 22 can have minimal stretching. For example, if a 40 lb weight were attached to the outer sheath assembly, it would only stretch about 0.1 inches over an approximate 40 inches of length. Other types of sheathes, again such as PEBAX, would stretch up to 1.5 inches with the same application of force.

Moving distally, the outer sheath assembly 22 can include a third segment 60 and a second segment 58, the second segment 58 being proximal to the third segment 60. The third segment 60 may be larger in inner diameter and outer diameter than the second segment 58, and may be sized in length and inner diameter to receive a prosthesis 70 as described herein in a collapsed configuration. These two segments can each have a different diameter, thereby forming a stepped configuration.

It should be noted that the second segment 58, relative to the overall length of the delivery system 10, is still generally positioned at a distal portion of the delivery system 10 while the delivery system 10 is being used to deliver the replacement valve towards the in situ implantation site. Moreover, the outer sheath assembly 22 may include other segments positioned proximal of the second segment 58. Such segments may, for example, couple the second segment 58 to a handle of the delivery system 10. The third segment 60 can be positioned radially outward from a replacement valve when the delivery system 10 is in an initial, delivery configuration such that the replacement valve is maintained in the delivery system 10 in an undeployed configuration.

The second segment 58 can be formed from a hypotube 150 (such as a nitinol hypotube) as shown in the embodiment in FIGS. 11A-E showing a flat pattern of the hypotube 150. As shown, the hypotube 150 can have a plurality of spaced slots 152 extending along the length from a distal end 156 to a proximal end 154 of the hypotube 150. Thus, when wrapped in a tube form, a spine 161 can be formed along its length between the ends of each slots 152. As shown, the slots 152 can be generally open and wide towards the middle, thereby allowing ePTFE to pass through the slots so that the first side and second side can be sintered together during manufacturing, thereby fully covering the hypotube 150 in ePTFE. The slots 152 can be a number, e.g., greater than 40, generally repeating and identical slots that extend along the length of the hypotube 150. Slots 152 may be provided along substantially the entire length of the tube as illustrated, or may be provided only in portions along the length of the tube. In some embodiments, as shown in FIG. 11B-C, the hypotube 150 may have a pair of rectangular slots 157 on its proximal and distal ends 156. The rectangular slots 157 can differ in size between the two ends or may be the same in size. In some embodiments, the hypotube 150 may only have the rectangular slots 157 on the proximal end 154, and instead the spaced slots 152 can extend almost to the distalmost end 156. This configuration is shown in FIG. 11A.

As shown, the slots 152 may be formed with a generally H-shaped structure centered on the hypotube 150. The slots 152 may have a generally T-shaped ends 153 spaced circumferentially opposite one another on the flat hypotube 150. These T-shaped ends 153 can be connected by a circumferential slot 155 extending circumferentially between the two slots. The circumferential slot 155 can change in height between the two w-shaped slots. For example, the circumferential slot 155 can have a greater height in the middle than where the circumferential slot 155 connects to the T-shaped ends 153. As shown in FIGS. 11A-B, each of the slots 152 may generally have the same dimensions along the length of the hypotube 150.

In the embodiment shown in FIG. 11C, the slots 152 may change in width between the proximal end 154 to the distal end 156. For example, as shown, the proximal end may have slots 152 having a smaller width than the slots at the distal end 156. Further, the slots 152 can progressively increase in width from the proximal end 154 to the distal end 154, where the majority of slots are the large width slots. As shown in FIG. 11C, the first three slots 152 from the proximal end can have a shorter width than the slots 152 on the proximal end, with the first three slots 152 increasing in width from the proximalmost slot to the distalmost slot of the first three slots 152. Any number of slots and slot configurations can be used. This progression of slot size can be useful in making strain apply more evenly across the hypotube 150 as a proximal force applied to the distal end 154 tends to apply first to the proximal-most slot. Thus, smaller slots 152 at the proximal end 154 can withstand a greater force as there is more material. Further, the spine 161 will increase in width from the proximal end 154 to the distal end 156, while remaining generally parallel with the longitudinal axis of the hypotube 150.

In some embodiments, smaller slots can be used. For example, slots can be spaced offset from one another to create, for example, a spiral pattern. In some embodiments, adjacent slots can be offset by about 90°, thereby forming a repeating pattern along the longitudinal lengths of the hypotube 150.

The outer sheath assembly 22 can include a lumen running therethrough to allow the sheath assembly 22 to be moveable or slideable relative to components contained therein. The walls forming the third segment 60 and/or the walls forming the second segment 58 can be formed from one or more materials, such as PTFE, ePTFE, PEBAX, ULTEM, PEEK, urethane, nitinol, stainless steel, and/or any other biocompatible material. Preferably, the third segment 60 is formed from one or more materials which allow the third segment 60 to be compliant and flexible while still maintaining a sufficient degree of radial strength to maintain a replacement valve within the third segment 60 without substantial radial deformation which could increase friction between the third segment 60 and a replacement valve contained therein, sufficient column strength to resist buckling of the third segment 60, and sufficient tear resistance to reduce the likelihood that the replacement valve causes the third segment 60 to tear. Flexibility of the third segment 60 can be advantageous, particularly for a transseptal approach. For example, while being retracted along a curved member, the third segment 60 can follow the curved member without applying significant forces upon the curved member which may cause the curved member to decrease in radius. Rather, the third segment 60 can bend and/or kink as it is being retracted along such a curved member such that the radius of the curved member is maintained.

The hypotube 150 can be optimized for maximum flexibility and minimum strain while providing for structural rigidity. Thus, the hypotube 150 can be formed from stainless still instead of nitinol, which can advantageously incase processing/manufacturing, though other materials can be used as well. The hypotube 150 can be about 5.5, 6.0, 6.3, 6.5, 7.0, or 7.5 inches in length, the particular dimensions of the hypotube 150 is not limiting.

Delivery Method

Methods of use of the delivery system in connection with a replacement mitral valve will now be described. In particular, the delivery system 10 can be used in a method for percutaneous delivery of the replacement mitral valve to treat patients with moderate to severe mitral regurgitation. The below methods are just a few examples of the how the delivery system may be used. It will be understood that the delivery systems described herein can be used as part of other methods as well.

Figure 13:
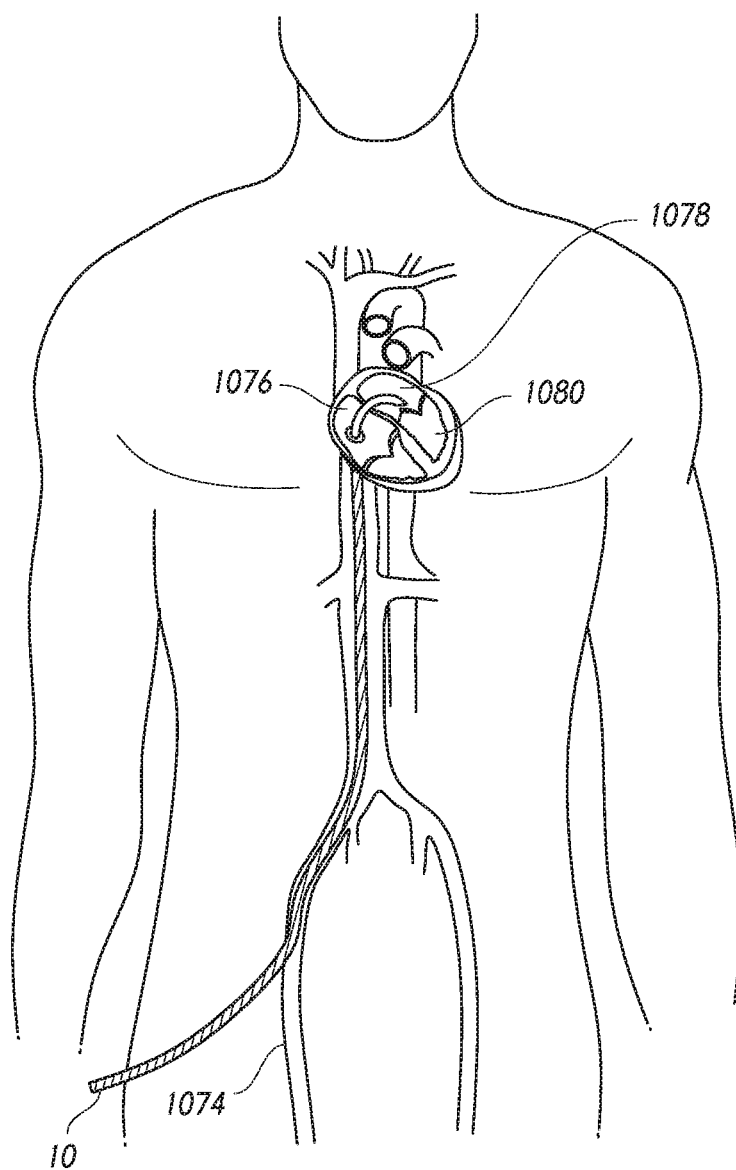
FIG. 13 illustrates a schematic representation of a transfemoral delivery approach.

As shown in FIG. 13, in one embodiment the delivery system 10 can be placed in the ipsilateral femoral vein 1074 and advanced to the right atrium 1076. A transseptal puncture using known techniques can then be performed to obtain access to the left atrium 1078. The delivery system 10 can then be advanced in to the left atrium 1078 and then to the left ventricle 1080. FIG. 13 shows the delivery system 10 extending from the ipsilateral femoral vein 1074 to the left atrium 1078. In embodiments of the disclosure, a guide wire is not necessary to position the delivery system 10 in the proper position, although in other embodiments, one or more guide wires may still be used.

Accordingly, it can be advantageous for a user to be able to steer the delivery system 10 through the complex areas of the heart in order to place a replacement mitral valve in line with the native mitral valve. This task can be performed with or without the use of a guide wire with the above disclosed system. The distal end of the delivery system can be inserted into the left atrium 1078. A user can then turn the steering knob 610 on the handle 14 in order to cause bending of the mid shaft 50, and thus the distal end of the delivery system 10. A user can then continue to pass the bent delivery system through the transseptal puncture and into the left atrium 1078. A user can then further manipulate the steering knob 610 to create an even greater bend in the mid shaft 50. Further, a user can torque the entire delivery system 10 to further manipulate and control the position of the delivery system 10. In the fully bent configuration, a user can then place the replacement mitral valve in the proper location. This can advantageously allow delivery of a replacement valve to an in situ implantation site, such as a native mitral valve, via a wider variety of approaches, such as a transseptal approach.

Figure 14:
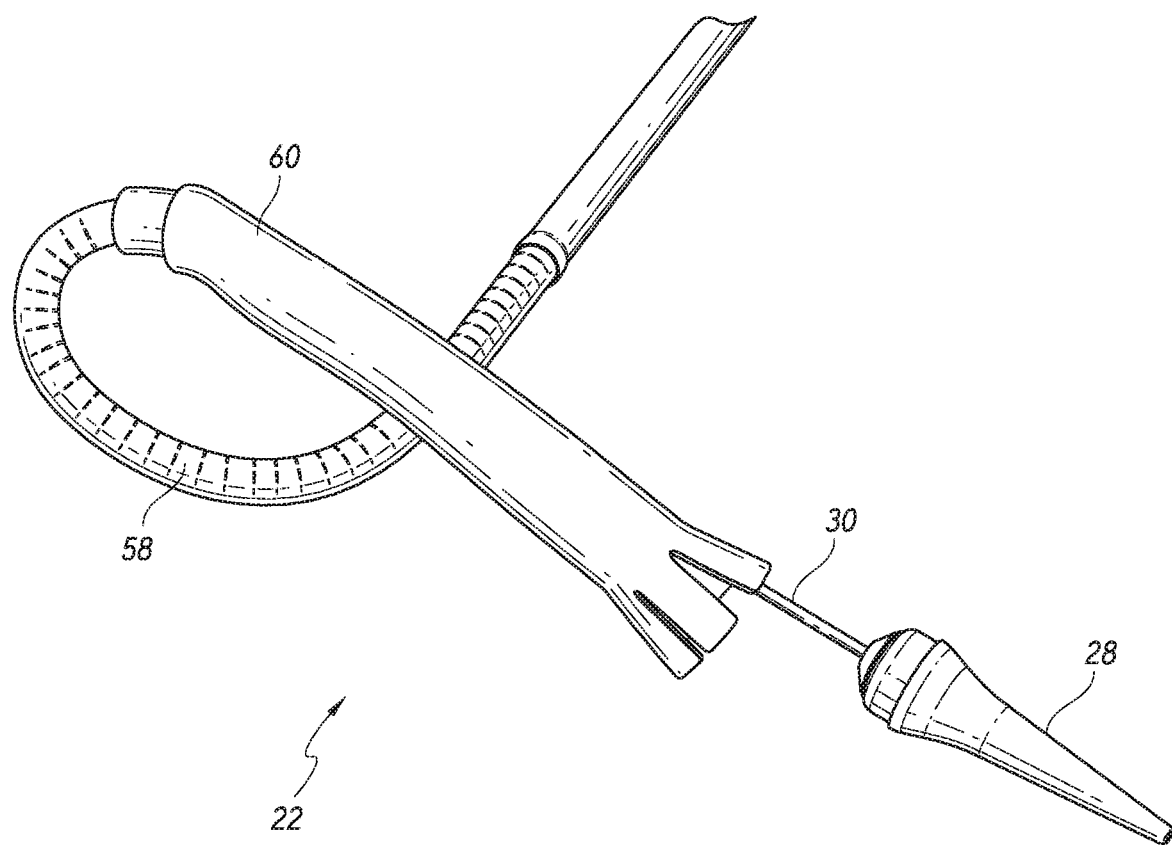
FIG. 14 illustrates bending of a delivery system.

FIG. 14 illustrates the bending motion of the outer sheath assembly 22. As discussed above, the mid shaft 50 (not shown but within outer sheath assembly 22) can be bent through actuation of the steering knob 610. As the mid shaft 50 is bent, it will press against an inner surface of the outer sheath assembly 22, thereby forcing the outer sheath assembly 22 to bend along with the mid shaft 50. Further, an inner surface of the mid shaft 50 will press against an outer surface of the inner retention shaft 42, which will press against the nose cone shaft 30, thus bending the inner retention shaft 42 and the nose cone shaft 30 along with the mid shaft 50. Accordingly, the distal end of the delivery system 50 will bend as shown in FIG. 14 due to the actuation of the mid shaft 50.

As shown in FIG. 14, the outer sheath assembly 22, specifically second segment 58 can be substantially bent to conform to the bending of the mid shaft 50. The embodiment shown in FIG. 14 can allow for three-dimensional bending of the delivery system 10. For example, as shown, the nose cone 28 can be angled approximately 90° from a longitudinal axis of the delivery system 10 when in an unbent position. However, FIG. 14 shows one particular position, and the delivery system 10 can be bent into other angles as well. The delivery system 10 can be bent in a manner to align with the anatomy of a heart, thus allowing the delivery system 10 to pass through the transseptal puncture and position the delivery system 10 to deliver a prosthesis 70 into the mitral valve annulus.

It should be understood that the bending experienced by the delivery system especially between the right atrium 1076 and the mitral valve are relatively complex and are generally not in a single plane, although single plane flexibility can be used. This part of the delivery system may experience bending between 110-180 degrees and typically between 130-160 degrees, of course this is dependent on the actual anatomy of the patient.

Further descriptions of the delivery methodology, as well of a discussion of a guide wire which can be used in some embodiments, can be found in U.S. Provisional App. No. 62/210,165, filed Aug. 26, 2015.

Figure 15:
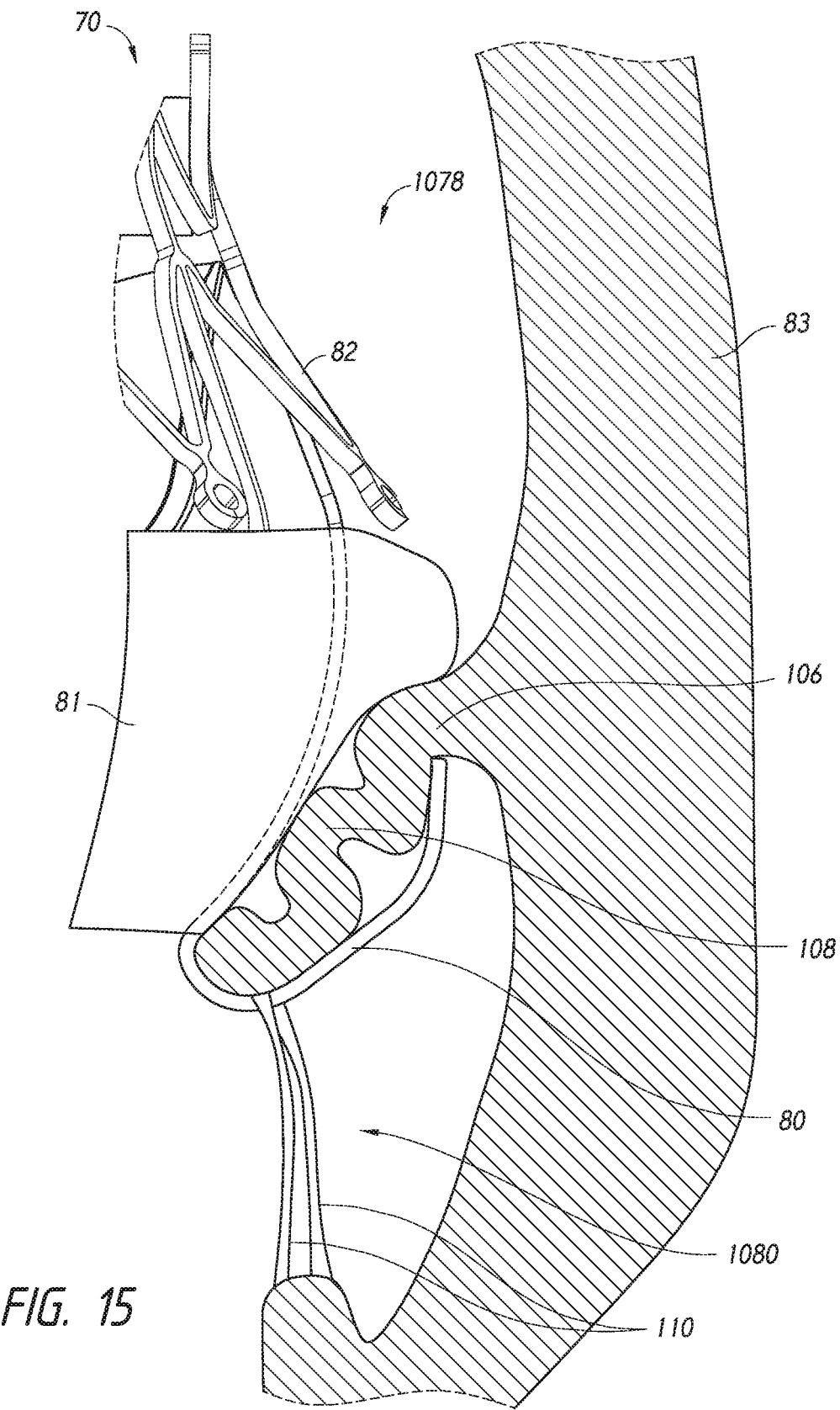
FIG. 15 illustrates a schematic representation of a valve prosthesis positioned within a native mitral valve.

Reference is now made to FIG. 15 which illustrates a schematic representation of an embodiment of a replacement heart valve (prosthesis 70) positioned within a native mitral valve of a heart 83. Further details regarding how the prosthesis 70 may be positioned at the native mitral valve are described in U.S. patent application Ser. No. 14/716,507, filed May 19, 2015, the entirety of which is hereby incorporated by reference, including but not limited to FIGS. 13A-15 and paragraphs [0036]-[0045]. A portion of the native mitral valve is shown schematically and represents typical anatomy, including a left atrium 1078 positioned above an annulus 106 and a left ventricle 1080 positioned below the annulus 106. The left atrium 1078 and left ventricle 1080 communicate with one another through a mitral annulus 106. Also shown schematically in FIG. 15 is a native mitral leaflet 108 having chordae tendineae 110 that connect a downstream end of the mitral leaflet 108 to the papillary muscle of the left ventricle 1080. The portion of the prosthesis 70 disposed upstream of the annulus 106 (toward the left atrium 1078) can be referred to as being positioned supra-annularly. The portion generally within the annulus 106 is referred to positioned intra-annularly. The portion downstream of the annulus 106 is referred to as being positioned sub-annularly (toward the left ventricle 1080).

As shown in the situation illustrated in FIG. 15, the replacement heart valve (e.g., prosthesis 70) can be disposed so that the mitral annulus 106 is between the distal anchors 80 and the proximal anchors 82. In some situations, the prosthesis 70 can be positioned such that ends or tips of the distal anchors 80 contact the annulus 106 as shown, for example, in FIG. 15. In some situations, the prosthesis 10 can be positioned such that ends or tips of the distal anchors 80 do not contact the annulus 106. In some situations, the prosthesis 70 can be positioned such that the distal anchors 80 do not extend around the leaflet 108. Further, the prosthesis 70 can be at least partially surrounded by an annular flap 81 between the distal anchors 82 and the proximal anchors 82. This flap 81 can wrap around the frame of the prosthesis 70 and help position the prosthesis 70 in the desired position in the body.

As illustrated in FIG. 15, the replacement heart valve 70 can be positioned so that the ends or tips of the distal anchors 80 are on a ventricular side of the mitral annulus 106 and the ends or tips of the proximal anchors 82 are on an atrial side of the mitral annulus 106. The distal anchors 80 can be positioned such that the ends or tips of the distal anchors 80 are on a ventricular side of the native leaflets beyond a location where chordae tendineae 110 connect to free ends of the native leaflets. The distal anchors 80 may extend between at least some of the chordae tendineae 110 and, in some situations such as those shown in FIG. 15, can contact or engage a ventricular side of the annulus 106. It is also contemplated that in some situations, the distal anchors 80 may not contact the annulus 106, though the distal anchors 80 may still contact the native leaflet 108. In some situations, the distal anchors 80 can contact tissue of the left ventricle 104 beyond the annulus 106 and/or a ventricular side of the leaflets.

During delivery, the distal anchors 80 (along with the frame) can be moved toward the ventricular side of the annulus 106 with the distal anchors 80 extending between at least some of the chordae tendineae 110 to provide tension on the chordae tendineae 110. The degree of tension provided on the chordae tendineae 110 can differ. For example, little to no tension may be present in the chordae tendineae 110 where the leaflet 108 is shorter than or similar in size to the distal anchors 80. A greater degree of tension may be present in the chordae tendineae 110 where the leaflet 108 is longer than the distal anchors 80 and, as such, takes on a compacted form and is pulled proximally. An even greater degree of tension may be present in the chordae tendineae 110 where the leaflets 108 are even longer relative to the distal anchors 80. The leaflet 108 can be sufficiently long such that the distal anchors 80 do not contact the annulus 106.

The proximal anchors 82 can be positioned such that the ends or tips of the proximal anchors 82 are adjacent the atrial side of the annulus 106 and/or tissue of the left atrium 1078 beyond the annulus 106. In some situations, some or all of the proximal anchors 82 may only occasionally contact or engage atrial side of the annulus 106 and/or tissue of the left atrium 1078 beyond the annulus 106. For example, as illustrate in FIG. 15, the proximal anchors 82 may be spaced from the atrial side of the annulus 106 and/or tissue of the left atrium 1078 beyond the annulus 106. The proximal anchors 82 could provide axial stability for the prosthesis 10. In some situations, some or all of the proximal anchors 82 may not contact an annular flap 81. This may occur when the annular flap 81 is in a collapsed configuration although it may also occur when the annular flap 81 is in an expanded configuration. In some situations, some or all of the proximal anchors 82 may contact the annular flap 81. This may occur when the annular flap 81 is in an expanded configuration although it may also occur when the annular flap 81 is in a collapsed configuration. It is also contemplated that some or all of the proximal anchors 82 may contact the atrial side of the annulus 106 and/or tissue of the left atrium 1078 beyond the annulus 106

The annular flap 81 can be positioned such that a proximal portion of the annular flap 81 is positioned along or adjacent an atrial side of the annulus 106. The proximal portion can be positioned between the atrial side of the annulus 106 and the proximal anchors 82. The proximal portion can extend radially outward such that the annular flap 81 is positioned along or adjacent tissue of the left atrium 1078 beyond the annulus 106. The annular flap 81 can create a seal over the atrial side of the annulus 106 when the flap 81 is in the expanded state.

Alternate Valve Prosthesis

Figure 16:
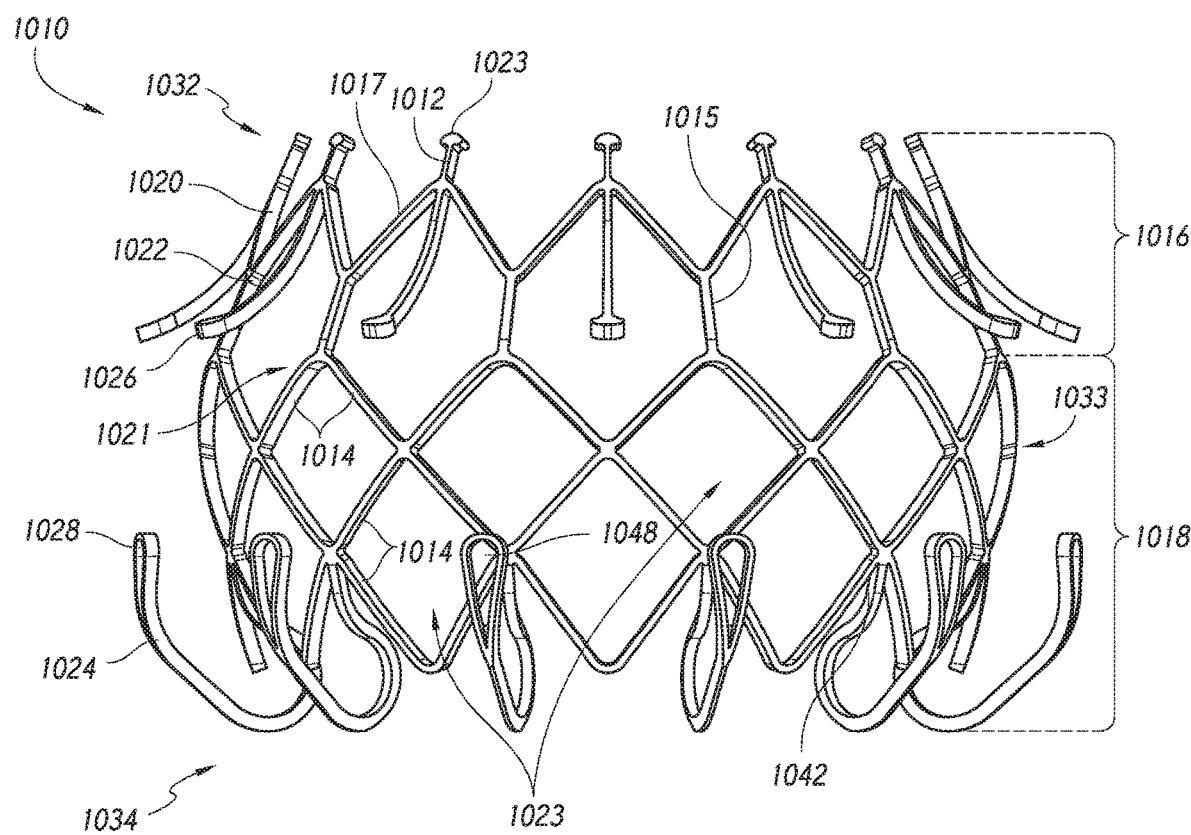
FIG. 16 shows a side view of an alternate embodiment of a valve prosthesis that may be delivered using the delivery systems described herein.

FIG. 16 illustrates an alternate embodiment of a valve prosthesis 1010 which can be used in conjunction with the delivery systems disclosed herein. The illustrated prosthesis 1010 includes a frame 1020 that may be self-expanding or balloon expandable. The prosthesis 1010 may be a replacement valve that can be designed to replace a damaged or diseased native heart valve such as a mitral valve, as discussed above. The additional features of the replacement valve are not shown in FIG. 16 in order to more clearly illustrate features of the frame 1020. It will also be understood that the prosthesis 1010 is not limited to being a replacement valve. In addition, it will be understood in FIG. 16, that only a front portion of the frame 1020 is shown for further ease of illustration.

The frame 1020 can be made of many different materials, but is preferably made from metal. In some embodiments, the frame 1020 can be made from a shape memory material, such as nitinol. A wire frame or a metal tube can be used to make the frame 1020. The wire frame of a metal tube can be cut or etched to remove all but the desired metal skeleton. In some embodiments a metal tube is laser cut in a repeating pattern to form the frame 1020. As shown, one of the anchors 1022 can include an eyelet, which can help manufacturing with alignment. As the frame 1020 can be generally round and symmetric, the eyelet can serve as a reference position for frame dimensional measurements as well as alignment. However, the eyelet may not be included in all embodiments. Further, more eyelets can be included on the anchors 1022 as well, and the particular number of eyelets is not limiting. The flat pattern can be cut from a metal tube and then the tube can be shaped and/or bent to the expanded shape shown in FIG. 16. In some embodiments, the frame 1020 is self-expanding so that it naturally assumes the expanded shape or configuration. The frame 1020 can further be expanded and/or compressed and/or otherwise worked to have the desired shape or shapes, such as for introduction and implantation.

As shown, the frame when in an expanded configuration, such as in a fully expanded configuration, has a bulbous or slightly bulbous shape, with a middle portion 1033 being larger than the proximal 1032 and distal 1034 ends. In some embodiments, the inside diameter of the both ends can be the same, or it can be bigger on one end than the other, while still having a middle portion 1033 larger than both the proximal and distal ends 1032/1034. In some embodiments, the effective diameter of the distal frame end 1034 is smaller than the effective diameter of the middle portion 1033. The bulbous shape of the frame 1020 can advantageously allow the frame 1020 to engage a native valve annulus or other body cavity, while spacing the inlet and outlet from the heart or vessel wall. This can help reduce undesired contact between the prosthesis and the heart or vessel, such as the ventricular wall of the heart. In some embodiments, the frame 1020 may not have a bulbous portion, and can have substantially the same outer dimension along its entire length (e.g., cylindrical), or it may have one end larger than the other end. The prosthesis 1010 and frame 1020 may be similar to the replacement heart valves and associated frames disclosed in U.S. Pat. No. 8,403,983, U.S. Publication Nos. 2010/0298931, 2011/0313515, 2012/0078353, 2014/0277390, 2014/0277422, 2014/0277427, and 2016/0317301, the entireties of each of which are hereby incorporated by reference and made a part of this specification. This is inclusive of the entire disclosure and is not in any way limited to the disclosure of the replacement heart valves and associated frames.

A number of struts collectively make up the frame 1020. FIG. 16 illustrates the frame in an expanded configuration with a number of proximal struts 1012 that extend substantially longitudinally to enlarged proximal ends 1013. A proximal row of circumferentially-expansible struts 1017 connects the proximal struts 1012, having a zig-zag or undulating shape such that between each proximal strut 1012, the struts 1017 form a V-shape. From the distal ends of each of the V's, vertical struts 1015 extend substantially longitudinally in a distal direction. The distal ends of the vertical struts 1015 then connect to a row of diamond-shaped cells 1023 formed by a plurality of circumferentially-expansible struts 1014 having a zig-zag or undulating shape. As illustrated, the proximalmost row of struts 1014 extend distally away from the distal ends of the vertical struts 1015 in a V-shape, thereby forming hexagonal-shaped cells 1021 bounded by the proximal row of struts 1017, the vertical struts 1015, and the proximalmost row of struts 1014. The embodiment of FIG. 16 further comprises a second, distal row of diamond-shaped cells 1023 further defined by additional circumferentially-expansible struts 1014, wherein the proximalmost corner of the second row of diamond-shaped cells 1023 coincides with the distalmost corner of the hexagonal-shaped cells 1021 and the side corners of the diamond-shaped cells in the first, proximal row.

The proximal struts 1012 and the vertical struts 1015 may be arranged so that they are parallel or generally or substantially parallel to a longitudinal axis of the frame. The proximal struts 1012 and the vertical struts 1015 can further be inclined relative to the longitudinal axis so that the proximal ends of the proximal struts 1012 are closer to the longitudinal axis than distal ends of the proximal struts 1012. The longitudinal axis of the frame 1020 may be defined as the central axis that extends through the center of the frame 1020 between the proximal 1032 and distal 1034 ends.

The illustrated embodiment includes one ring, or row of hexagonal or generally hexagonal cells 1021 shown in proximal portion 1016 of the frame 1020, and two rows of diamond-shaped cells 1023 shown in distal portion 1018. As discussed in more detail below, the proximal portion 1016 includes the portion of the hexagonal cells 1021 extending proximally from the distal end of vertical struts 1015 and may be considered to be or to include a substantially non-foreshortening portion. Foreshortening refers to the ability of the frame to longitudinally shorten as the frame radially expands. The distal portion 1018 includes the diamond-shaped cells 1023 extending distally from the distal ends of the vertical struts 1015 and may be considered a foreshortening portion. In some embodiments, the hexagonal cells 1021 can be irregular hexagons. For example, the hexagonal cells 1021 can be symmetrical about a vertical axis extending from proximal to distal ends of the hexagonal cell 1021. Vertical struts 1015 can form opposite sides, while circumferentially-expansible struts 1014 of two adjacent diamond-shaped cells 1023 in the proximalmost row can form a base of the hexagonal cell 1021 ending at a distalmost corner that is distal to the distal ends of the vertical struts 1015. These circumferentially-expansible struts 1014 can connect to the vertical struts 1015. Further, the proximal row of circumferentially-expansible struts 1017 can form the upper sides of the hexagonal cell 1021 that extend to a proximalmost corner of the hexagonal cell 1021 that is proximal to the proximal ends of vertical struts 1015. These circumferentially-expansible struts 1017 can connect to the proximal ends of the vertical struts 1015. In some embodiments, two of the sides of the hexagonal cells 1021 can be one length, while the other four sides of the hexagonal cells 1021 can be a greater length. In some embodiments, the two sides with the same length can be generally parallel to one another.

As described above, the frame 1020 has a proximal portion 1016 and a distal portion 1018. In FIG. 16 it can be seen that the proximal struts 1012 and the majority of the hexagonal cells 1021 are included in the proximal portion 1016, while circumferentially-expansible struts 1014 form the distal portion 1018 having a first, proximal row of diamond-shaped cells 1023 and a second, distal row of diamond-shaped cells 1023. As illustrated, adjacent cells between the proximal row and the distal row may share common struts. In some embodiments, the diamond-shaped cells 1023 in the second, distal row may have a larger longitudinal height than the diamond-shaped cells 1023 in the first, proximal row. When the frame is radially collapsed or compacted, the struts 1014 become more parallel with respect to the longitudinal axis of the frame, causing an outer diameter of the frame to decrease and the longitudinal length of the frame to increase in the distal portion 1018. As the frame moves from a compacted position to an expanded position, the longitudinal length of the frame can decrease due to foreshortening of the diamond-shaped cells 1023 in distal portion 1018. But, the frame length does not substantially change length in the proximal portion 1016 due to the vertical struts 1015, although the proximal row of circumferentially-expansible struts 1017 in the proximal portion 1016 may allow for some foreshortening.

The frame 1020 shown in FIG. 16 can have a relatively squat configuration. For example, the ratio of the width of the largest portion of the frame 1020 to the height (e.g., extending from the proximal 1032 to distal end 1034) of the frame 1020 when the frame is in its expanded configuration can be about 3:1, about 2.5:1, about 2.0:1, about 1.5:1, about 4:3, about 1.3:1, about 1.25:1, or about 1.0:1. Thus, in some embodiments the width at the largest portion of the frame 1020 can be greater than the height. Generally, the frame 1020 can have a larger aspect ratio than the prosthesis 70 shown in FIG. 15. In some embodiments, the height of portion 1016 can be greater than, equal to, or less than the height of portion 1018. In some embodiments, the height of proximal portion 1016 can be approximately ½ the height of distal portion 1018. In some embodiments, the frame 1020 can have an overall height of about 32 mm (or about 32 mm). The frame 1020 can have an inner diameter of 40 mm (or about 40 mm). In some embodiments, the frame 1020 can have a height of 29, 30, 31, 33, 34, 35, or 36 mm (or about 29, about 30, about 31, about 33, about 34, about 35, or about 36 mm).

Foreshortening of the frame 1020 can be used to engage and secure the prosthesis to intralumenal tissue in a body cavity, for example tissue at or adjacent a native valve, such as a native valve annulus and/or leaflets. Opposing anchors 1022, 1024 can be constructed on the frame 1020 so that portions of the anchors, such as tips or ends 1026, 1028, move closer together as the frame foreshortens. As one example, this can allow the anchors 1022, 1024 to grasp tissue on opposite sides of the native mitral annulus to thereby secure the prosthesis at the mitral valve. In some embodiments, one set of anchors (such as anchors 1024) are secured to or grasp tissue, while the other set of anchors (such as anchors 1022) are used to provide stabilization and help align the prosthesis, and may or may not directly engage tissue, as described further below.

The anchors 1022, 1024 and anchor tips 1026, 1028 are preferably located along the frame 1020 with at least part of the foreshortening portion positioned between the anchors so that a portion of the anchors will move closer together with expansion of the frame. As shown, distal anchors 1024 are connected to the distal portion 1018, and may extend from distalmost corners of the diamond-shaped cells 1023. As illustrated, the distal anchors 1024 extend distally from distalmost corners of the proximal row of diamond-shaped cells 1023, such that the second, distal row of diamond-shaped cells 1023 extend longitudinally alongside a portion of the distal anchors.

Preferably, each of the anchors 1022, 1024 is positioned or extends generally radially outwardly from the frame 1020 so that the anchor tips 1026, 1028 are generally spaced away or radially outward from the rest of the frame 1020 and from where the base of the anchors connect to the frame. For example, the anchor tips may be located radially outward from the middle portion 1033 of the frame, with the tips 1026 and 1028 being axially spaced from one another. The middle portion 1033, which has the largest cross-sectional dimension when the frame is radially expanded, can be defined by the proximalmost row of diamond-shaped cells 1023. The anchors 1022, 1024 can include a base located on the anchor on a side opposite the tip. The base can be for example where the anchor begins to extend from or away from the frame 1020.

Proximal anchors 1022 are shown having a single strut extending into the hexagonal cells 1021 of portion 1016. Thus, the anchor 1022 extends from a proximal intersection of two segments of the hexagonal cell 1021, for example, from the proximalmost corner of the hexagonal cells 1021. As shown, the proximal anchors 1022 extend generally distally into the hexagonal cells 1021 while curving outwards away from the frame 1020. Thus, the anchor 1022 extends radially outwardly from the frame 1020 as it extends generally distally towards the tip 1026. The tips 1026 of the proximal anchors 1022 can end after extending approximately half the length or more of the hexagonal cells 1021. Further, the tips 1026 can extend farther outwards than the main body of the frame 1020.

In some embodiments, the tip 1026 of the anchor 1022 also includes an enlarged or bulbed portion 1026, which can be generally circular in shape, though the particular shape is not limiting. As illustrated, the bulbed portion 1026 is located at the distal end, though the bulbed portion 1026 can be positioned in other locations along the anchor 1022. The bulbed portion 1026 can have a radius greater than the width of the rest of the anchor 1022, making the bulbed portion 1026 larger than the rest of the anchor 1022. As illustrated, the enlarged or bulbed portions can extend in a direction generally or substantially perpendicular to the longitudinal axis, caused for example by gradual bending of the anchor 1022 distally and radially outwardly.

As another example, the distal anchors 1024 are shown having looped ends 1048. The looped ends can be larger near the tip to form a type of elongated teardrop. In some embodiments, the tips 1028 may be substantially flat. The looped end may assist the frame in not getting caught up on structures at or near the treatment location. For example, each loop can be configured so that when the frame is deployed in-situ and expands, the movement of each loop from a delivered position to a deployed position avoids getting caught on the papillary muscles.

Figure 21:
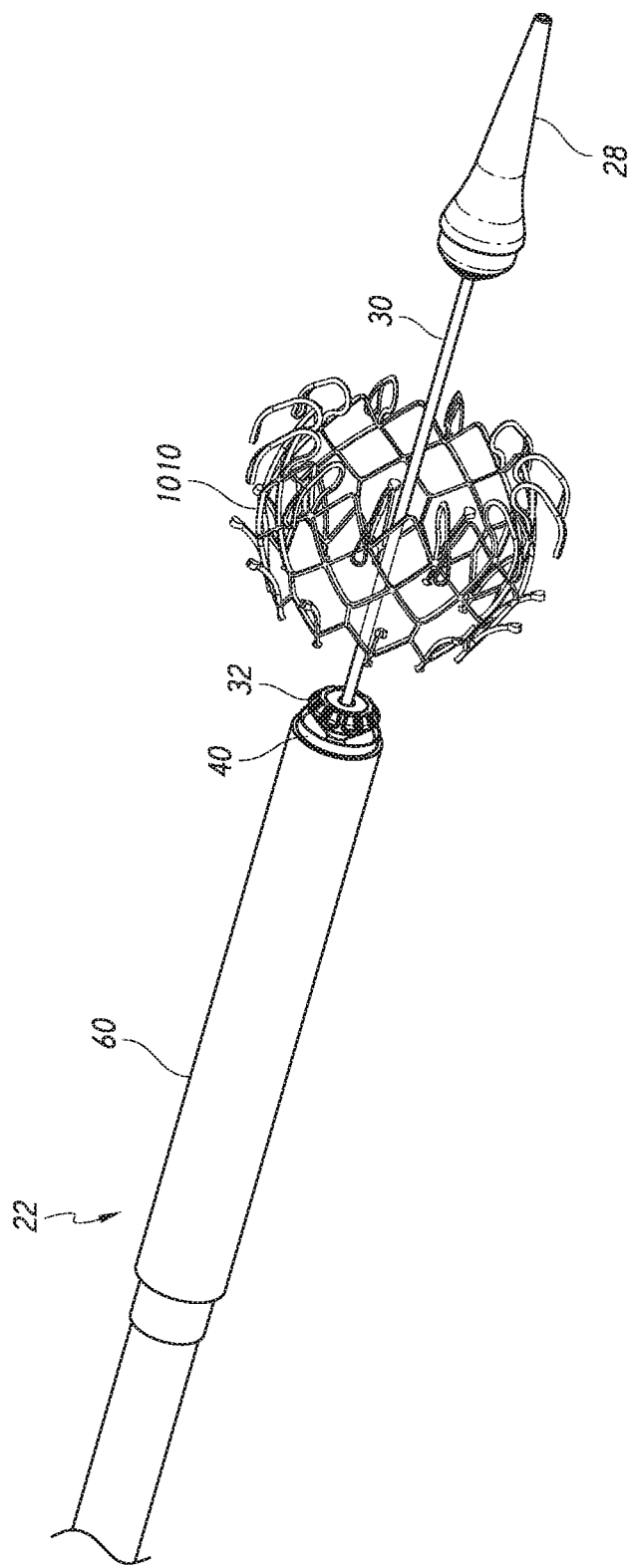

Each distal anchor 1024 is connected to the frame at a base 1042. As illustrated in FIG. 21, the base of the distal anchor may be at a location where the corners of adjacent cells meet, such that the base is proximal to the distal end 1034 of the frame. In other embodiments, the base of the distal anchor may be at a distal most corner of a cell, which corresponds to a distal most point on the frame The distal anchors as illustrated extend from the base 1042 generally distally before bending back around in an arcuate and/or bent segment where the distal anchor extends generally proximally and radially outwardly from the frame. As shown, the anchors 1024 may also extend generally distally and radially inwardly from the base with respect to the frame such that the distal most point on the prosthesis has a smaller inside diameter than where the base 1042 connects to the frame. The inside diameter at the distal most point can be the same or substantially the same as the inside diameter of the proximal end, or may be smaller. As illustrated, the anchors 1024 may extend distally from the base 1042 and bend or curve radially inwardly and then curve approximately in a half-circle first further radially inwardly, and then around so that the anchor extends radially outwardly. This half-circle can provide a space for the distal ends of the leaflets to be stored, such as in the configurations described below. The anchors may then extend in a linear segment radially outwardly and proximally. Finally, the anchor may extend towards the tip 1028 in a direction parallel or substantially parallel to the longitudinal axis. Thus, the anchor as illustrated is bent around about 180 degrees from its base so that the tip 1028 extends in the opposite, proximal direction, which may be parallel or substantially parallel to the longitudinal axis of the frame. For example, in FIG. 16 it can be seen that the distal anchors 1024 are bent near the tips 1028 such that the ends of the anchors point proximally and are generally parallel with the longitudinal axis of the frame. Alternatively, the tip 1028 may extend generally proximally but still extend radially outwardly inclined or at an acute angle relative to the longitudinal axis of the frame It will be understood that the anchors can have various other configurations, including the various embodiments that follow. In some embodiments, each of the anchors can extend radially outwardly from the frame at an anchor base and terminate at an anchor tip. The anchors can be connected to the frame at one of many different locations including apices, junctions, other parts of struts, etc. The anchors can comprise first, second, third, or more spaced apart bending stages along the length of each anchor. The anchors can also extend either distally or proximally before and/or after one or more of the bending stages. A portion of the anchor may extend with the frame before or after any bending stages.

The tips or ends 1013 of proximal struts 1012 can be enlarged relative to other portions of the tips 1013. For example, the ends of tips 1013 can have a generally "mushroom" shape. The proximal struts 1012 and enlarged tips 1013 can form locking tabs used to engage a locking mechanism of a delivery system for the prosthesis. In some embodiments, the longitudinal extensions 1012 and the mushroom tips 1013 can be inclined generally radially inward.

Figure 17:
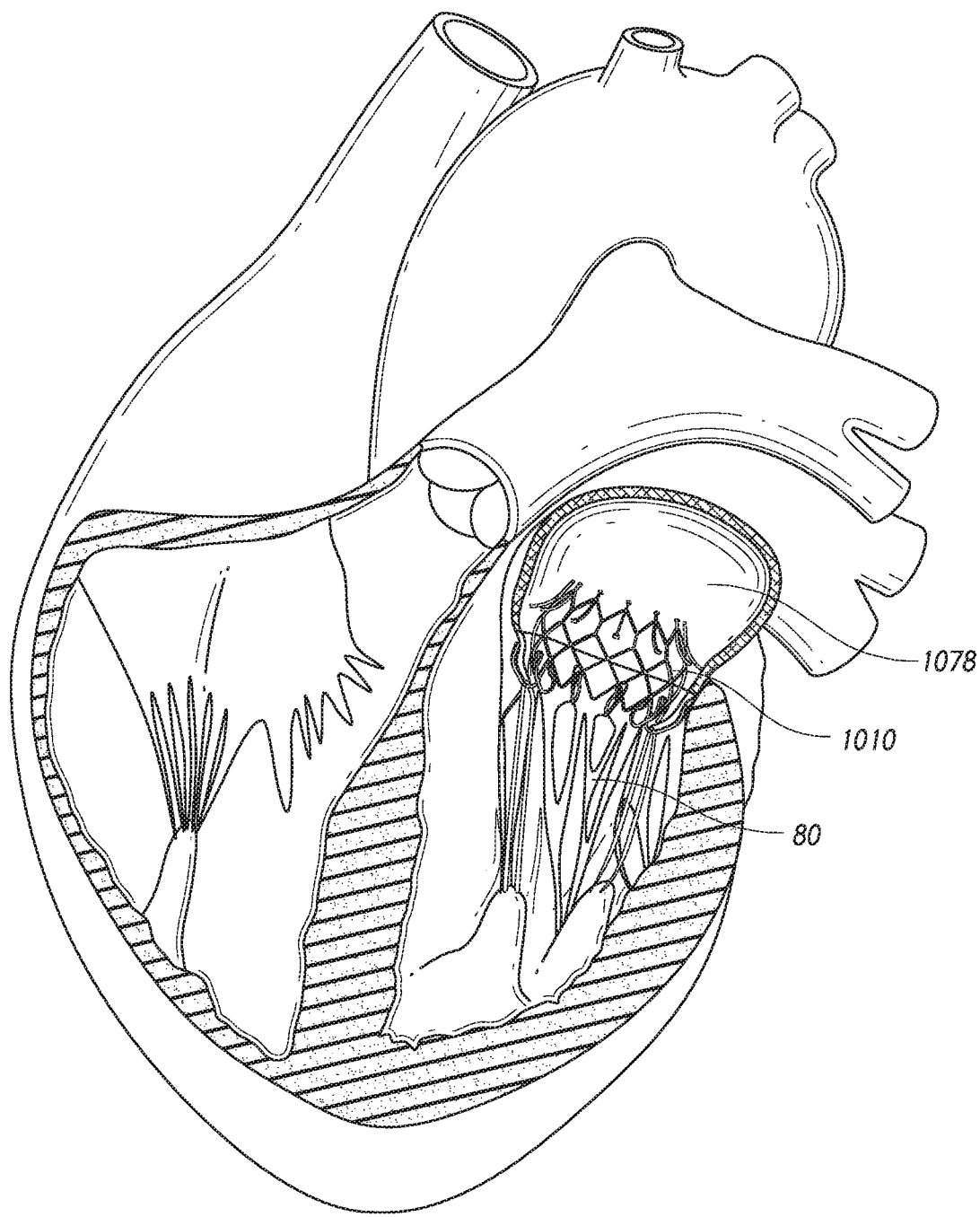
FIG. 17 shows the valve prosthesis frame of FIG. 16 located within a heart.

FIG. 17 shows the location of the prosthesis 1010 (with only the frame 1020 showing) delivered to a native mitral valve and located between left atrium 1078 and left ventricle 1080. The prosthesis 1010 may engage native tissue in a manner similar to that discussed in detail above with conjunction to FIG. 15.

Delivery Method

FIGS. 18-21 illustrate a method of delivery of the prosthesis 1010 to a desired anatomical position in a patient, such as to replace a mitral valve, to illustrate how the delivery system 10 is utilized to release the prosthesis. While the below disclosure is discussed with relation to prosthesis 1010, similar or the same procedure can be performed with respect to prosthesis 70. During the initial insertion of the prosthesis 1010 and the delivery system 10 into the body, the prosthesis 1010 can be located within the system 10, similar to as shown in FIG. 2A. The distal end 1034 of the prosthesis 1010, and specifically the distal anchors 1024, are restrained within the third segment 60 of the outer sheath assembly 22, thus preventing expansion of the prosthesis 1010. Similar to what is shown in FIG. 2A, the distal anchors 1024 can extend distally when positioned in the third segment 60. The proximal end 1032 of the prosthesis 1010 is restrained within the outer retention ring 40 and within a portion of the inner retention member 32.

The system 10 can first be positioned to a particular location in a patient's body, such as at the native mitral valve, through the use of the steering mechanisms discussed herein or other techniques. With reference next to the step of FIG. 18 once the system 10 has positioned the prosthesis 1010 at the in situ target location, e.g. the native mitral valve, the outer sheath assembly 22 can be moved relatively proximally away from the nose cone 28 to uncover at least a portion of the prosthesis 1010, in particular the distal end 1034 of the prosthesis 1010. At this point, the distal anchors 1024 can flip proximally and the distal end 1034 begins to expand radially outward. For example, if the system 10 has been delivered to a native mitral valve location through a transseptal approach, the nose cone is positioned in the left ventricle, thus having the prosthesis 1010 be generally perpendicular to the plane of the mitral annulus. The distal anchors 1024, which may be considered ventricular anchors, expand radially outward within the left ventricle. The distal anchors 1024 can be located above the papillary heads, but below the mitral annulus and mitral leaflets. In some embodiments, the distal anchors 1024 may contact and/or extend between the chordae in the left ventricle, as well as contact the leaflets, as they expand radially. In some embodiments, the distal anchors 1024 may not contact and/or extend between the chordae or contact the leaflets. Depending on the position of the prosthesis 1010, the distal ends of the distal anchors 1024 may be at or below where the chordae connect to the free edge of the native leaflets.

Figure 19:
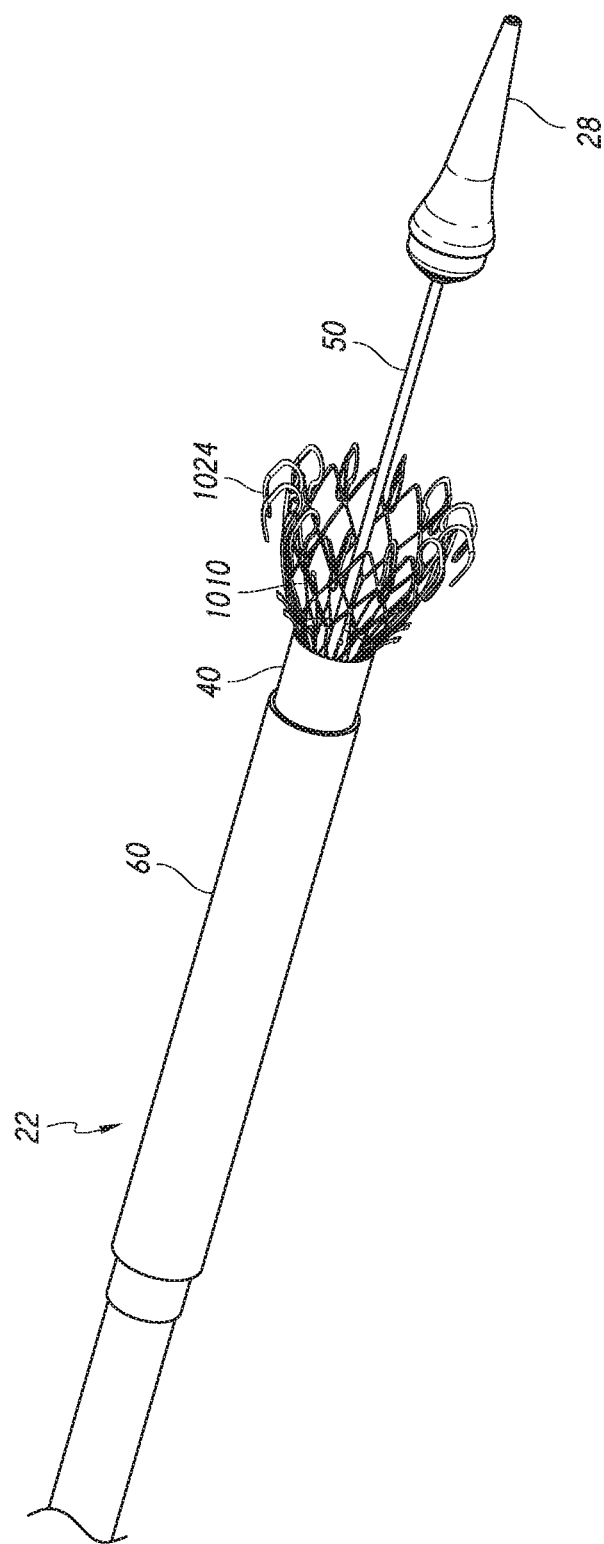

With reference next to the step of FIG. 19, outer sheath assembly 22 can be further moved relatively away from the nose cone 28 to further uncover the prosthesis 1010. As shown in the illustrated embodiment, the distal end 1034 of the prosthesis 1010 is expanded outwardly. It should be noted that the proximal end 1032 of the prosthesis 1010 can remain covered by the outer retention ring 40 during this step such that the proximal end 1032 remains in a radially compacted state. At this time, the system 10 may be withdrawn proximally so that the distal anchors 1024 capture and engage the leaflets of the mitral valve, or may be moved proximally to reposition the prosthesis 1010. Further, the system 10 may be torqued, which may cause the distal anchors 1024 to put tension on the chordae through which at least some of the distal anchors may extend between. However, in some embodiments the distal anchors 1024 may not put tension on the chordae. In some embodiments, the distal anchors 1024 may capture the native leaflet and be between the chordae without any further movement of the system 10 after withdrawing the outer sheath assembly 22.

Accordingly, during this step the system 10 may be moved proximally or distally to cause the distal or ventricular anchors 1024 to properly capture the native mitral valve leaflets. In particular, the tips of the ventricular anchors 1024 may be moved proximally to engage a ventricular side of the native annulus, so that the native leaflets are positioned between the anchors 1024 and the body of the prosthesis 1010. When the prosthesis 1010 is in its final position, there may or may not be tension on the chordae, though the distal anchors 1024 can be located between at least some of the chordae.

Figure 20:
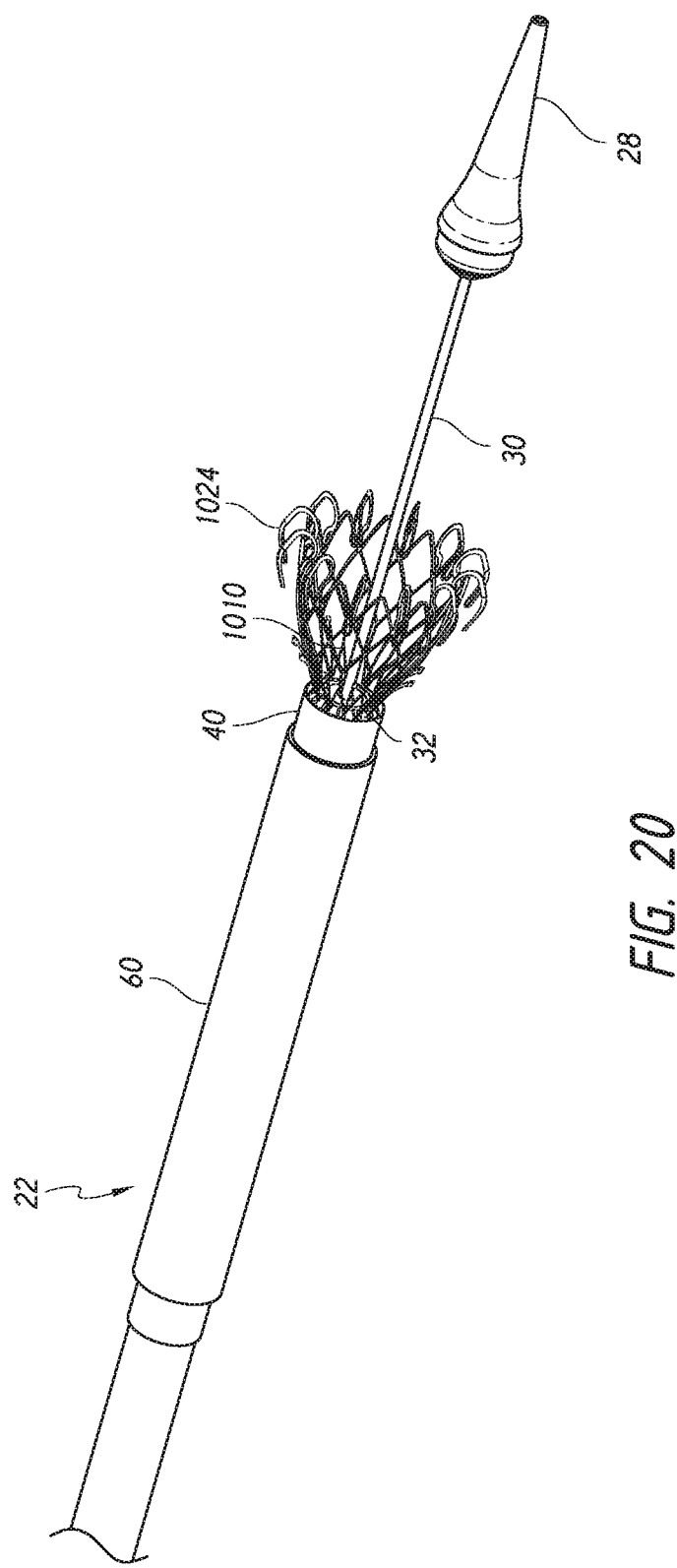

As shown in FIG. 20, once the distal end 1034 of the prosthesis 1010 is fully expanded (or as fully expanded as possible at this point), the outer retention ring 40 can be moved relatively proximally to expose the inner retention member 32, thus beginning the expansion of the proximal end 1032 of the prosthesis 1010. For example, in a mitral valve replacement procedure, after the distal or ventricular anchors 1024 are positioned between at least some of the chordae tendineae and/or engage the native mitral valve annulus, the proximal end 1032 of the prosthesis 1010 may be expanded within the left atrium.

With reference next to the step of FIG. 21, the outer retention ring 40 can continue to be moved proximally such that the proximal end 1032 of the prosthesis 1010 can radially expand to its fully expanded configuration. After expansion and release of the prosthesis 1010, the nose cone 28 can be withdrawn through the center of the expanded prosthesis 1010 and into the outer sheath assembly 22. The system 10 can then be removed from the patient.

Alternative Systems and Modifications

FIGS. 22-24B show embodiments of a delivery system 5000 which can have some modifications over the above-discussed system 10. However, it will be understood that components discussed below can be incorporated into the system 10 above, but for ease of disclosure they will be discussed separately below. Further, reference numbers discussed above are used for unmodified components discussed below. The delivery system 5000 can be utilized similar to how system 10 was described to deliver prostheses such as the prostheses 70 and 1010.

Figure 22:
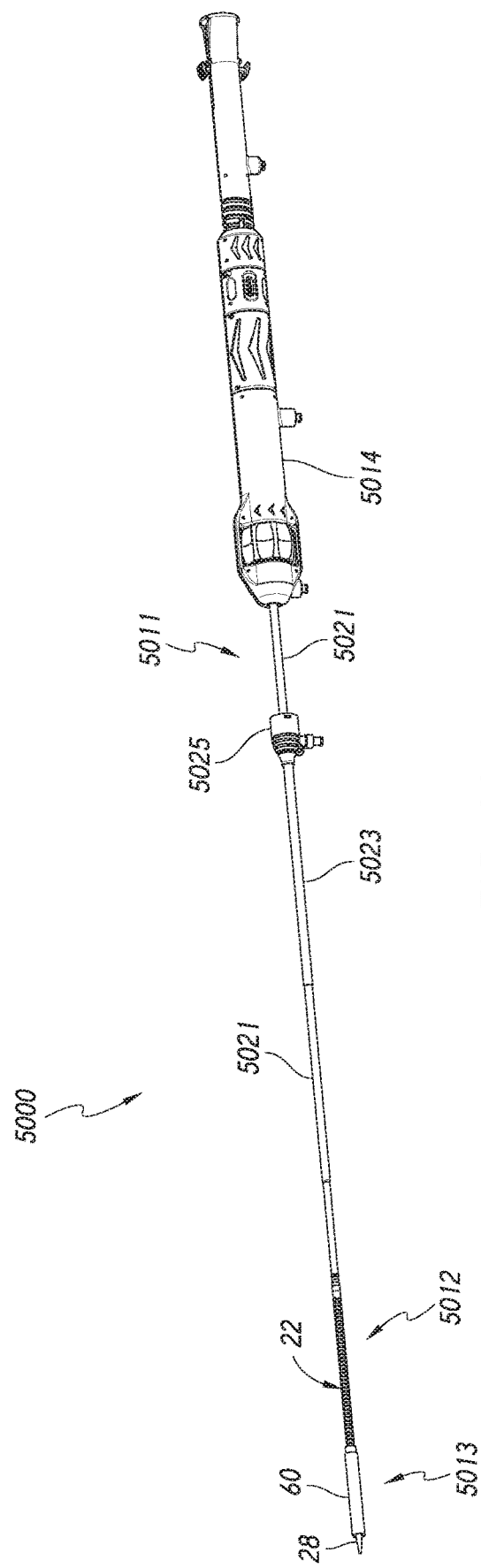
FIG. 22 shows an alternate embodiment of a delivery system.

As shown in FIG. 22, the delivery system 5000 can include an elongate shaft assembly 5012 comprising a proximal end 5011 and a distal end 5013, wherein a handle 5014 is coupled to the proximal end of the assembly 5012. The elongate shaft assembly 5012 can be used to hold the prosthesis 70/1010 for advancement of the same through the vasculature to a treatment location.

Surrounding the outer sheath assembly 22 can be a stationary sheath (or shaft) 5021. The stationary sheath 5021 can extend partially down the length of the system 5000. The proximal end of the stationary sheath 5021 can be fixed to the handle 5014.

Surrounding the stationary sheath 5021 can be the integrated (or live-on) introducer sheath 5023. The introducer sheath 5023 can be relatively rigid, and approximately a foot in length, though the particular dimensions are not limiting. The introducer sheath 5023 can contain a hemostasis gasket within its lumen that can seal with the stationary sheath 5021. In some embodiments, introducer sheath 5023 can be a braided 72D Pebax shaft with a PTFE internal liner, though other materials can be used as well. Further, the introducer sheath 5023 can include a port assembly 5025 for flushing of the lumen of the introducer sheath 5023.

The stationary sheath 5021 allows the outer sheath assembly 22 to be withdrawn through the introducer sheath 5023 without unwanted movement of the system 5000. For example, if the gasket of the introducer sheath 5023 was sealed onto the outer sheath assembly 22, attempts to retract the outer sheath assembly 22 may move the entire system 5000 forward instead due to the high friction of the gasket on the outer sheath assembly 22.

Moving now to FIG. 23, the outer sheath assembly 60 (shown in FIG. 4) and mid shaft assembly 20 (shown in FIG. 5) have been removed from the distal end 5013 of FIG. 22, though the outer retention ring 40 remains for clarity. As shown, the delivery system 5000 can include a spacer sleeve 5020 located concentrically between the mid shaft 50 of the mid shaft assembly 20 and the inner retention shaft 42 of the inner assembly 18 and proximal to the outer retention ring 40. The pull wire 612 can pass along an outer surface of the spacer sleeve 5020. The spacer sleeve 5020 can be made of a polymer material such as braided Pebax and can be lined, for example with PTFE, on the inner diameter, though the particular material is not limiting. The spacer sleeve 5020 can advantageously reduce friction as the mid shaft 50 and inner retention shaft 42 are made of metal. Further, the mid shaft 50 can have teeth that would break on the inner retention shaft 42 upon bending of the mid shaft assembly 20. Thus, the spacer sleeve 5020 can act as a buffer between the mid shaft 50 and the inner retention shaft 42. Further, the spacer sleeve 5020 can take up any gap in radius between the mid shaft 50 and the inner retention shaft 42, preventing compressing or snaking of the inner assembly 18 during bending.

Accordingly, the spacer sleeve 5020 can float between the two layers (inner assembly 18 running through its lumen and the mid shaft assembly 20 being on the outside) which can take out any of the extra space. Thus, when the prosthesis 70/1010 is released, the inner assembly 18 no longer snakes and is held concentric. This can lead to a 1:1 motion during prosthesis 70/1010 release and a smooth and reliable prosthesis 70/1010 release.

The spacer sleeve 5020 can be mechanically contained by the other lumens and components (e.g., radially by the inner assembly 18 and mid shaft assembly 20 and longitudinally by the outer retention ring 40 and the first segment 43 of the mid shaft assembly 20), and is thus not physically attached to any of the other components, allowing the spacer sleeve 5020 to be "floating" in that area. In some embodiments, the spacer sleeve 5020 may have a shorter length than the mid shaft 50, in some embodiments approximately 1 cm shorter. The floating aspect of the spacer sleeve 5020 allows it to move where needed during deflection and provide a support and/or lubricious bear surface/surfaces. However, in some embodiments, the spacer sleeve 5020 can be connected to other components.

Figure 24A:
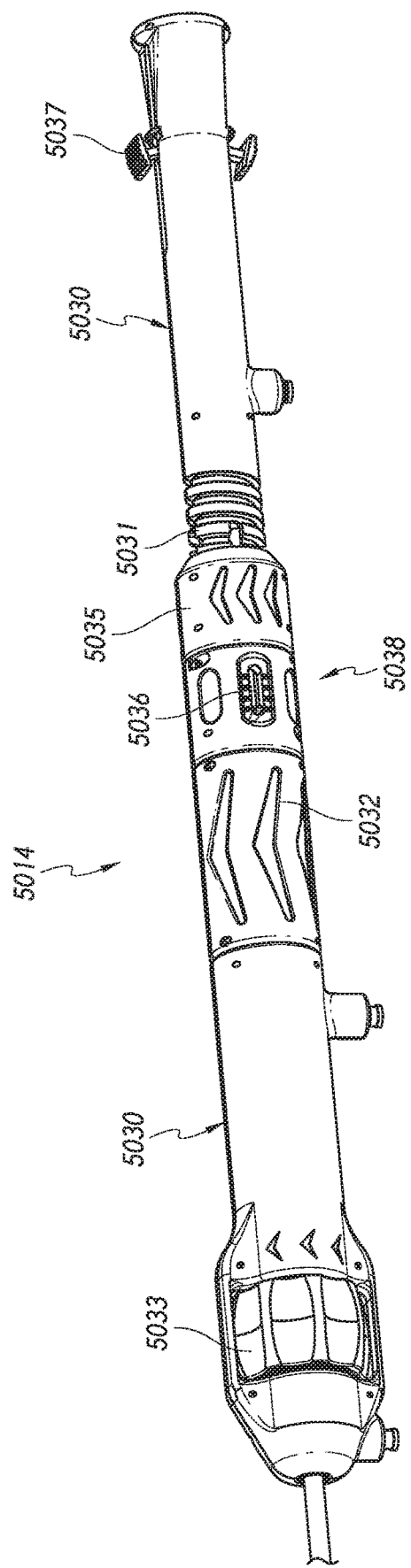
FIGS. 24A-B illustrate the handle of the delivery system of FIG. 22 in a distal and proximal position, respectively.
Figure 24B:
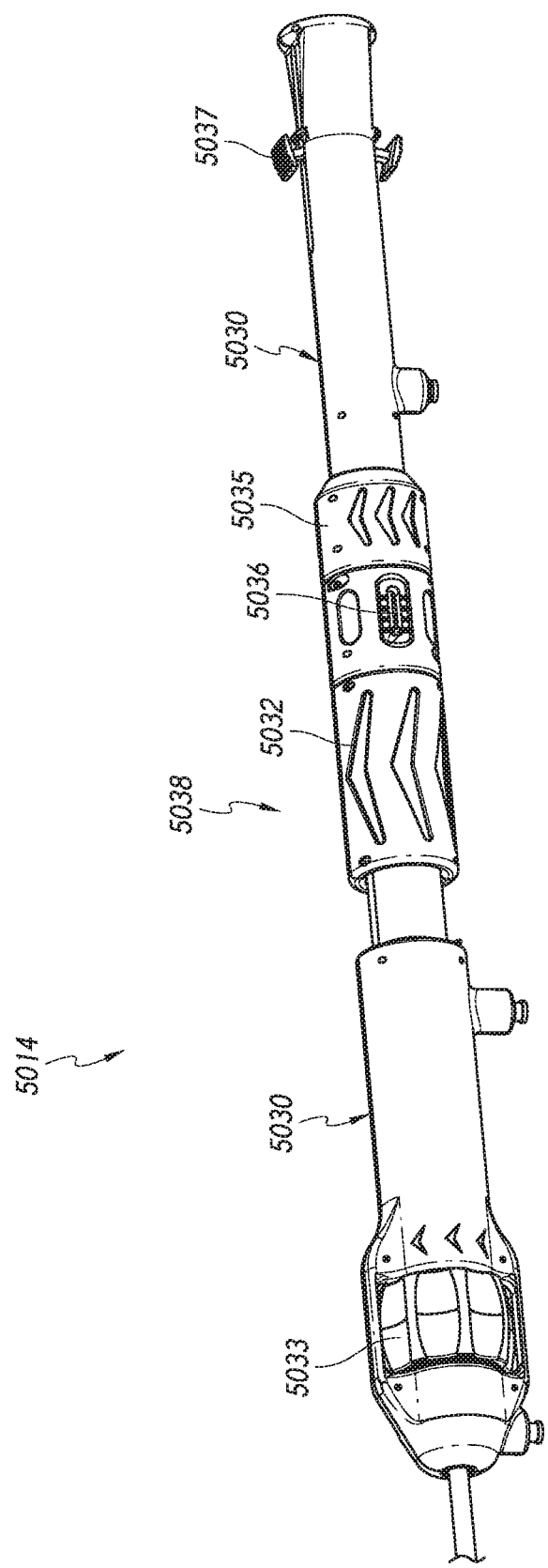
Figure 24C:
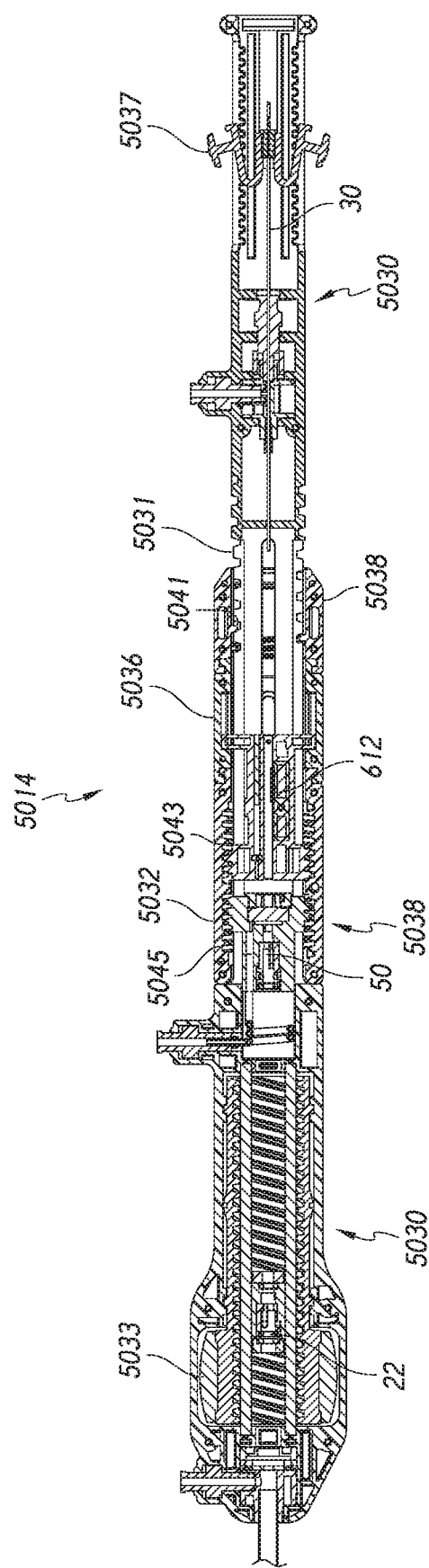
FIG. 24C illustrates a cross section of the handle of the delivery system of FIG. 22.

Further, FIGS. 24A-B show an embodiment of a handle 5014 that can be used in conjunction with the systems discussed in detail above. FIG. 24C illustrates a cross-section of the handle 5014 in the distal position. As shown, the handle 5014 can include an outer sheath assembly knob 5033 which can be rotated for translating the outer sheath 22, a deflection knob 5032 which can be rotated for bending the system 5000 (specifically activating the pull wires 612 to deflect the mid shaft 50), an indicator 5036 (discussed below), a mid shaft retraction knob 5035 which can be rotated for translating the mid shaft assembly 20, and a nose cone articulator 5037 which can be translated longitudinally for translating the nose cone assembly 31. In some embodiments, the deflection knob 5032 can distally pull the pull wire 612 while also proximally pushing the mid shaft assembly 20, thus preventing accidental release of the prosthesis 70/1010.

The deflection knob 5032, indicator section 5036, and mid shaft retraction knob 5035 can be generally connected and translated as one section, or sleigh, 5038 over the rest of the handle 5014 designated as stationary portion 5030.

Specifically, as shown the stationary portion 5030 includes outer threads 5031 that can be threadably attached to the mid shaft retraction knob 5035, such as with inner threads 5041. The proximal end of the mid shaft assembly 20 can be attached to an internal surface of the mid shaft retraction knob 5035. Thus, as the mid shaft retraction knob 5035 is rotated, it translates proximally or distally on the outer threads 5031 of the handle 5014. Thus, as the mid shaft retraction knob 5035 is rotated, the mid shaft assembly 20, deflection knob 5032, and indicator section 5036 translate along the thread as well. Accordingly, the sleigh 5038 can have a distal position (FIG. 24A) and a proximal position (FIG. 24B) where the sleigh 5038 is translated over the threads 5031 of the stationary portion 5030 of the handle 5014.

Indicators section 5036 can include indicators on the outer surface of the handle 5014 in order to provide a user with visual or auditory indications of the locations of certain parts of the system 5000. For example, in some embodiments, the indicators 5036 can provide visual or auditory indications of the deflection of the distal end of the system 5000. The indicator 5036 can contain "speed bumps" on an inside surface of a slot that can provide a clicking sound as the distal end of the system 5000 is deflected. In some embodiments, the indicators 5036 can include a number of a tab running through a slot with a number of markings, each marking being one rotation of the deflection knob 5032 as the tab passes through the slot.

In some embodiments, proximal connections of the mid shaft assembly 20 and the inner assembly 18 can include snap features to secure them (typically as rigid hypotubes on their proximal end) to the internal portions of the handle 5014. These snap features can provide strong connections and can resist both torque and compression/tension. In some embodiments, the snap connections can be supported externally from another component, which further prevents them from disengaging during use. Additionally, in some embodiments an O-ring can be used to seal the snap mechanisms hemostatically.

Operation of Handle

Discussed next is the operation of the distal end of the system 5000, shown in FIGS. 18-21, based on the embodiment discussed with respect to FIGS. 22-24B. The operation of the handle is described with reference to delivery of a replacement mitral valve prosthesis, though the handle and delivery system can be used to deliver other devices as well.

First, the distal end 5013 of the system 5000 is positioned into the desired location, such as at the mitral valve. The deflection knob 5032 can be rotated to pull the pull wire 612 attached to the outer retention ring 40. Thus, as the deflection knob 5032 is rotated, the mid shaft 50 will bend along the direction of the pull wire 612. Thus, this bending can be used to position the system 5000, in particular the distal end, at the desired patient location, such as at the native mitral valve. In some embodiments, rotation of the deflection knob can help steer the distal end of the delivery system 5000 through the septum and left atrium and into the left ventricle so that the prosthesis 1010 is located at the native mitral valve.

Further, rotation of the deflection knob 5032 can push the mid shaft 50 distally, in some cases simultaneously with the pulling of the pull wire 612, thus preventing unwanted release of the prosthesis 1010. The deflection knob 5032 can perform this action by having two sets of threads 5043/5045 on its internal surface that are in opposite directions. One of the threads is attached to the pull wire 612, and the other is attached to the mid shaft 50. Thus, when the deflection knob 5032 is rotated, one set of threads 5043 pull the pull wire 612 proximally while the other set of threads 5045 push the mid shaft 50 distally.

The system 5000 can be used to place the prosthesis 1010, covered by the outer sheath assembly 22 at this time, so that a central portion of the prosthesis 1010 is along the plane formed by the native mitral annulus. Thus, at this time the atrial anchors 1022 can be located in the left atrium and the ventricular anchors 1024 can be located in the left ventricle.

Figure 18:
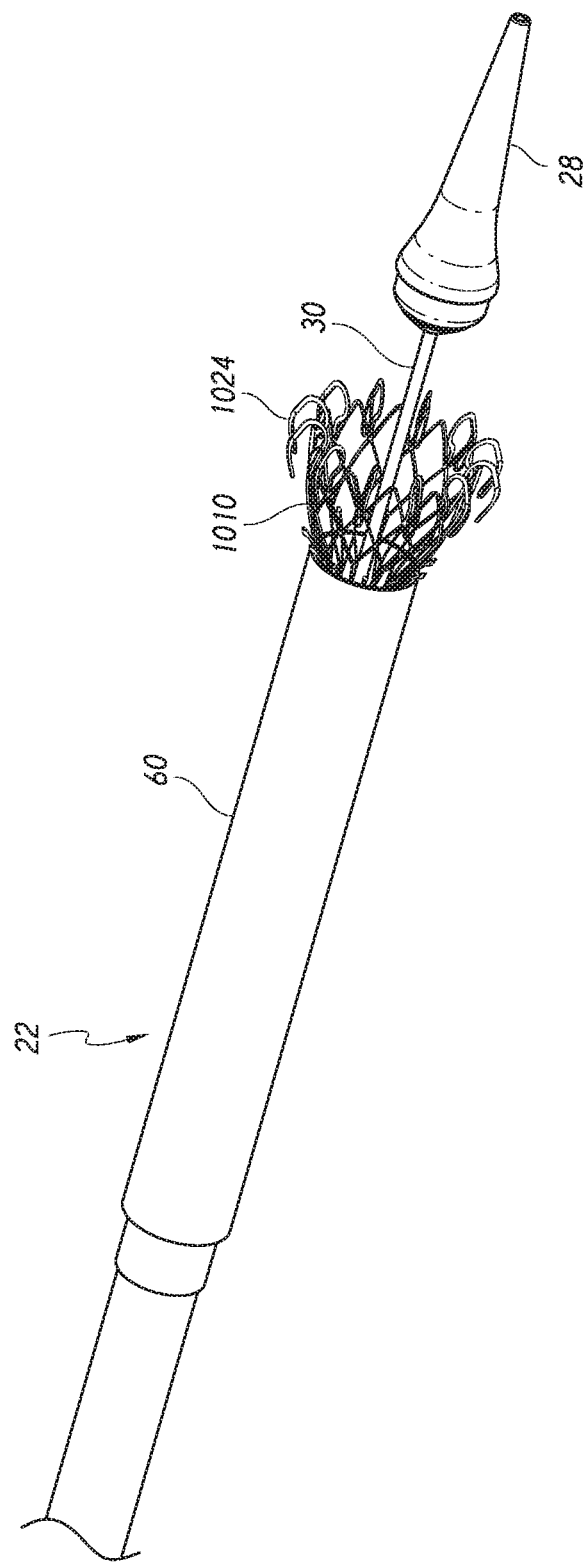
FIGS. 18-21 show steps of a method for delivery of the valve prosthesis of FIG. 16 to an anatomical location.

Next, the outer sheath assembly knob 5033 can be rotated in order to retract the outer sheath assembly 22 proximally relative to the nose cone 28, as shown in FIG. 18. Thus, the distal end of the prosthesis 1010 begins to expand, and the ventricular anchors 1024 flip from a distal position within outer sheath assembly 22 to a proximal position outside of the outer sheath assembly 22. The ventricular anchors 1024 can be located below the native mitral valve leaflets and between the chordae at this time, or may be distal to where the chordae connect to the free edge of the native valve leaflets. Further, the outer sheath assembly knob 5033 can be rotated further in order to further retract the outer sheath assembly 22, exposing the outer retention ring 40 as shown in FIG. 19.

At this time, the prosthesis 1010 can be repositioned as need be in the mitral valve area. For example, the system 5000 can be moved proximally or distally to capture the native valve leaflets by the ventricular anchors 1024, with the ventricular anchors 1024 positioned behind (or radially outward) of the native valve leaflets. In some embodiments, rotation of the outer sheath assembly knob 5033 to release the prosthesis 1010 will cause the ventricular anchors 1024 to hold the native mitral valve leaflets, such as shown in FIG. 15 as well as extend between chordae. In some embodiments, the system 5000 can be moved proximally to capture and hold the native mitral valve leaflets.

Once the prosthesis 1010 is in the desired position, such as with the ventricular anchors 1024 secured to tissue on a ventricular side of the native mitral valve annulus, the mid shaft retraction knob 5035 can then be rotated to retract the mid shaft assembly 20 proximally, as shown in FIG. 20. This allows the proximal end of the prosthesis 1010 to begin expanding. Further rotation of the mid shaft retraction knob 5035 exposes the inner retention ring 32, thus releasing the prosthesis 1010 and allowing it to fully expand into position as shown in FIG. 21, giving the prosthesis 1010 the final position shown in FIG. 15 and FIG. 17.

After release of the prosthesis 1010, the nose cone articulator 5037 can be moved proximally in order to withdraw the nose cone 28 through the prosthesis 1010 and into the outer sheath assembly 22 so that the nose cone 28 does not catch on tissue while removing the system 5000. Once the nose cone 28 is in the proper position, the entire system 5000 can be withdrawn from the patient.

Articulating Steering Mechanism

As discussed in detail above, a pull wire can be used for steering of the system 10. However, other steering mechanisms can be used as well, and the particular steering mechanism is not limiting. For example, as shown in FIGS. 25-27 and discussed in detail below, a pivoting bending section can be used in conjunction with (or replacing) the mid shaft assembly 20 or the outer sheath assembly 22, which can allow for two-way (or three-way, four-way, five-way, etc.) articulation of each "vertebra" connected to the next "vertebra." The pivoting bending section can also be used as a component in delivery systems other than those described herein. In some embodiments, more components can be added to provide four-way articulation. Thus, the bending section can bend to the "up-down" direction and the "right-left" direction simultaneously, allowing complicated articulations inside the cardiovascular system. In some embodiments, the articulation can be used to move the system 10 in a single plane. In some embodiments, the articulation can be used to move the system 10 in multiple planes (e.g., both up and down as well as left and right), such as two planes, three planes, four planes, etc. The handle 2001, represented as a box, can be any of the handles 14 or 5014 discussed above, or other modified handles.

FIG. 25 illustrates an articulation system 2000 that can be made up of a bending section 2002, a plurality of angulation wires 2004/2005, a chain and sprocket system 2006, and an angulation knob 2008. These components can be used in addition to the components discussed herein or can be used in as replacements to those components. In some embodiments, the articulation system 2000 can surround the outer sheath assembly 22 so that the outer sheath assembly 22 can pass through a lumen of the articulation system 2000. In some embodiments, a distal end 2024 of the articulation system 2000 can be proximal to the distal end of the outer sheathe assembly 22. In some embodiments, the articulation system 2000 can replace the outer sheath assembly 22.

As shown in FIG. 25, a pair of angulation wires 2004/2005 can be attached to the distal end 2024 of the bending section 2002. In some embodiments, the wires 2004/2005 are attached near to the distal end 2024. The wires 2004/2005 can be attached to opposite sides of the distal end of the bending section 2002 in order to provide motion to the bending section 2002. The wires 2004/2005 can extend through the system 10 and the bending section 2002 so that their proximal ends are attached to ends of a chain 2010 of the chain and sprocket system 2006, as shown in FIG. 25. For example, the proximal end of the first wire 2004 can be attached to one end of the chain 2010, and a proximal end of the second wire 2005 can then be attached to the opposite end of the chain 2010. The chain 2010 can then be wrapped around a sprocket 2012 so that turning of the sprocket 2012 can turn the chain 2010. Thus, if the first wire 2004 is pulled proximally by the sprocket 2012, the second wire 2005 will relieved of pressure from the sprocket 2012. The sprocket 2012 can be controlled through, for example, an angulation knob 2008 connected to the sprocket 2012, which gives the user control over the bending section 2002. In some embodiments, additional pull wires and another sprocket system and knob can be used to provide further dimensions of motion to the bending section 2002.

Figure 26A:
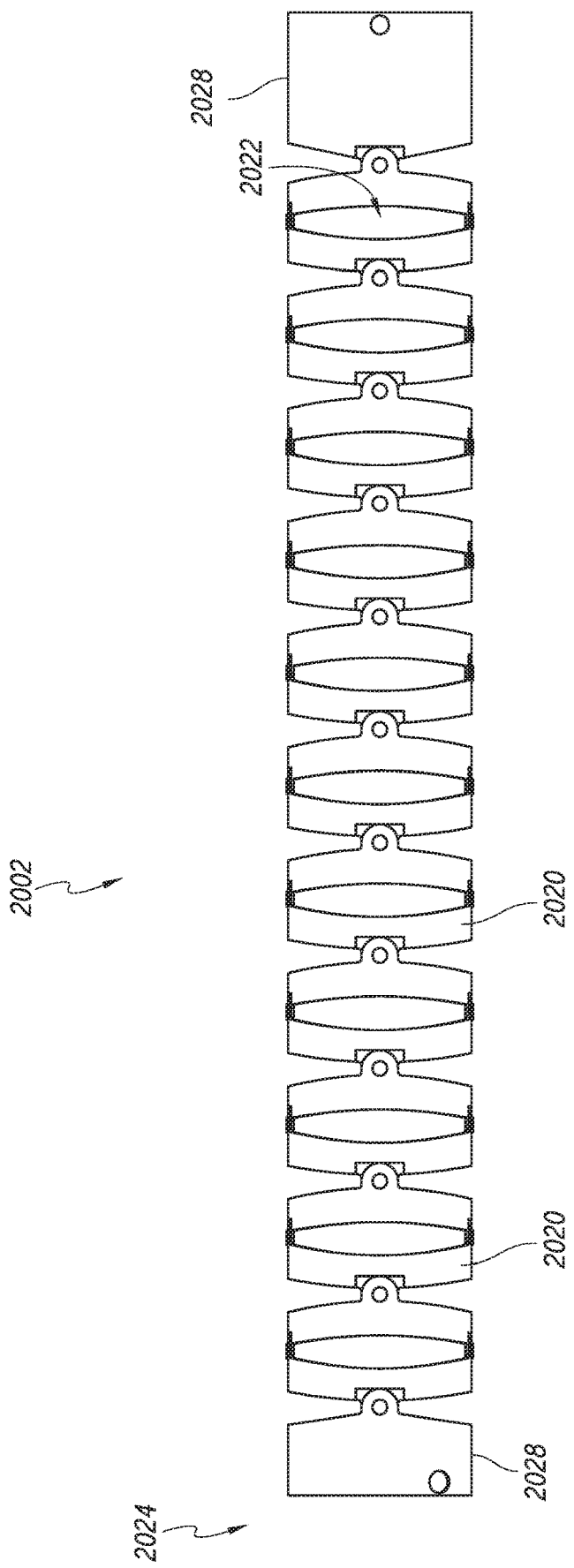
FIGS. 26A-C illustrate components of the articulating mechanism of FIG. 25.
Figure 27:
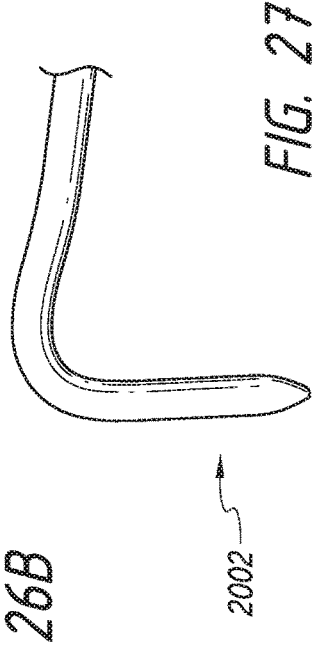
FIG. 27 illustrates example motion of the delivery system using the articulating mechanism of FIG. 25.

FIG. 26A illustrates an embodiment of the bending section 2002. As shown, the bending section 2002 can be formed from a number of different rings 2020 pivotably attached to one another. The rings 2020 can be attached to one another to form a lumen 2022 throughout the center of the rings 2020, thus allowing for the components discussed above to pass through, such as the different shafts and valve. In some embodiments, twenty three rings can be used, but the number of rings is not limiting. Further, at the distal 2024 and proximal 2026 ends of the bending sections, end ring components 2028 can be used to stabilize the bending section 2002. In some embodiments, such as shown in FIG. 26A, the end ring components 2028 have a greater longitudinal width than the rings 2020. In some embodiments, the end ring components 2028 may only have one set of pivot members as discussed below.

Figure 26C:
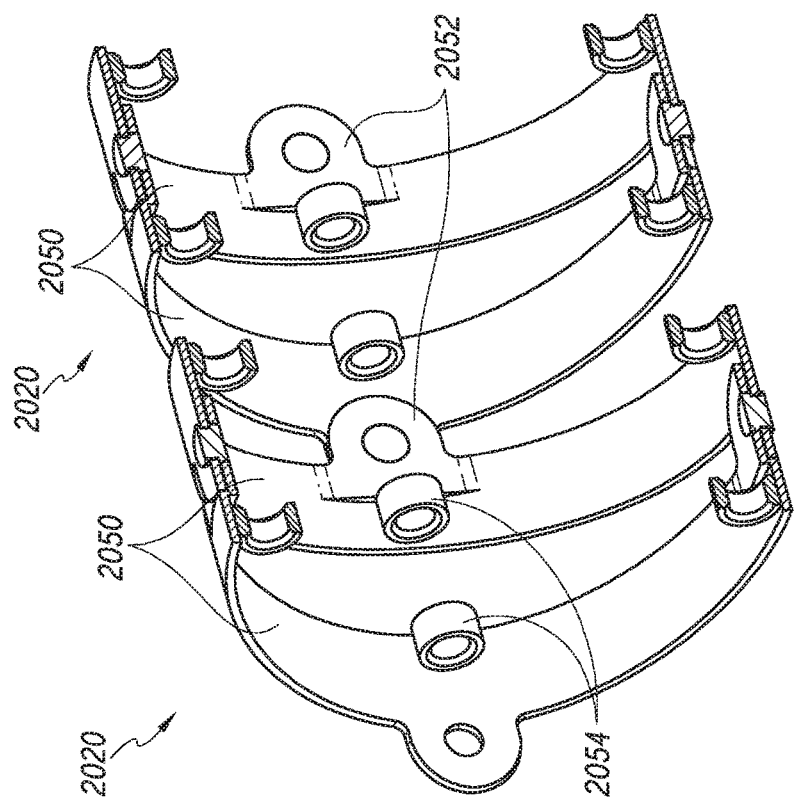
Figure 26B:
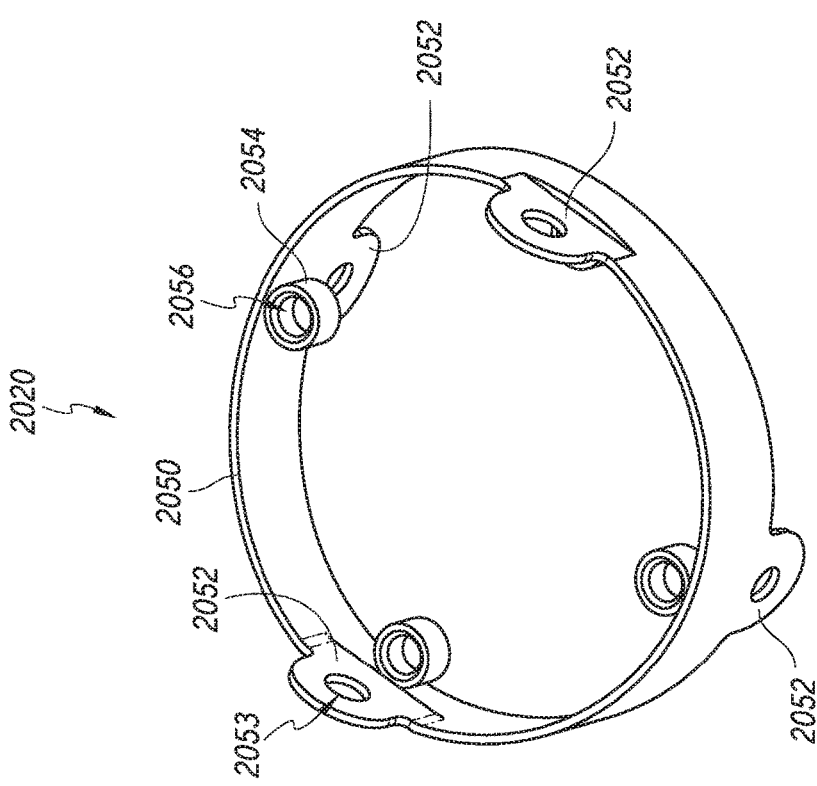

FIG. 26B illustrates a single ring 2020 which can be used in the bending section 2002. The rings 2020 can all be generally identical to one another, or there can be slight variations. As shown, the ring 2020 can include a body portion 2050 that forms the general ring shape. Further, extending from the body 2050 are a number of pivot members 2052. These members 2052 can extend longitudinally from the ring 2020, either proximally or distally. The pivot members 2052 can be generally semi-circular in shape and include an aperture 2053 extending radially, though the particular shape of the pivot member 2052 is not limiting.

In some embodiments, the body 2050 can include four different pivot members 2052, though other numbers of pivot members 2052 can be used as well such as 1, 2, 3, 5, or 6 pivot members, and the particular number of pivot members 2052 is not limiting. As shown, the pivot members 2052 can be spaced generally evenly around the body 2050, thus being approximately 90° spaced from one another. Other spacing can be used as well, especially with configurations that include more or less than four pivot members 2052. In some embodiments, adjacent pivot members 2052 can extend in an opposite longitudinal direction. For example, a first pivot member 2052 can extend in the proximal direction, a second pivot member 2052 can extend in the distal direction, a third pivot member 2052 can extend in a proximal direction, and a fourth pivot member 2052 can extend in a distal direction. Thus, pivot members 2052 on opposite sides of the body 2050 can extend the same longitudinal direction.

In addition, the ring 2020 can include eyelets 2054 attached to the inner surface of the ring 2020, though in some embodiments the eyelets 2054 can be on the outside. The eyelets 2054 can have an aperture 2056 that extend in the longitudinal direction. The eyelets 2054 can be used to receive the articulation wires 2004/2005 discussed above. In some embodiments, the eyelets 2054 can be aligned in the same circumferential position as the pivot members 2052. In some embodiments, the number of eyelets 2054 can be the same as the number of pull wires. For example, for 2D articulation two eyelets 2054 would be used for two pull wires, whereas for 3D articulation four eyelets 2054 would be used for four pull wires.

FIG. 26C illustrates a number of rings 2020 attached to one another. As shown, adjacent rings 2020 can be oriented so that the distally extending pivot members 2052 of one ring 2020 overlap the proximally extending pivot members 2052 of an adjacent ring 2020. A rivet, or other attachment mechanism, can then be placed through the apertures 2053 of the pivot members 2052, connecting all of the rings 2020 together.

Accordingly, articulation of the knob 2008 turn the sprocket 2012, pulling the chain 2010 attached to the proximal ends of the pull wires 2004/2005. Accordingly, the motion of the chain 2010 would pull one of the pull wires 2004 while releasing tension on the other pull wire 2005. As the pull wires 2004/2005 extend through the eyelets 2054 of the rings 2020 and connect to the distal end ring component 2028, this articulation would cause the bending section 2002 to flex by pivoting of the rings 2020 with respect to adjacent rings. Through the use of one sprocket and chain system 2006 with the two pull wires 2004/2005, single plane motion can occur in the bending section 2002. If additional systems and pull wires were used, three-dimensional movement of the bending section 2002 could be achieved, allowing for turning of the distal end 2028 as shown in FIGS. 25 and 27.

Steerable Distal Portion Construction

Disclosed herein are embodiments of a steerable distal portion for a delivery system, such as the delivery system 10 of FIG. 1. These portions can be used in conjunction with the delivery systems disclosed above. Further, while this section is discussed with respect to prosthesis 70 and delivery system 10, it will be understood that it can be used with respect to prosthesis 1010 and delivery system 5000, or other prostheses and delivery systems.

As shown in FIG. 2A, the distal anchors 80 of the prosthesis 70 can point generally distally when loaded on the delivery system 10. That is, the prosthesis 70 has a greater longitudinal length when in the delivered configuration than in the deployed configuration. As such, it can be advantageous for the delivery system 10 to have greater flexibility at the distal end of the delivery system 10 for steering the nosecone 28 and the distal portion of the delivery system 10 loaded with the prosthesis 70. Also, as has been mentioned, the distal anchors 80 can flip positions to point generally proximally by withdrawing proximally the outer sheath assembly 22 when deploying the prosthesis 70.

Accordingly, described below is a mechanism for a controlled release of the distal anchors 80 after the outer sheath assembly 22 is withdrawn proximally. The mechanism can operate by applying a force on the nose cone 28 (or a component within the nose cone 28) in the proximal direction to "steer" the nose cone 28 in a particular direction. More details of the application of the force will be described below. It can thus be advantageous for the delivery system 10 to be stiff enough to resisting bending or buckling at its flexible distal end so that the nose cone 28 can be pulled to steer the distal end of the delivery system 10, in particular through the steering of the nose cone 28. As shown in FIG. 28A, in some embodiments, the delivery system 10 can have a modified distal section 120 configured to bend for steering the nose cone 28 and the prosthesis 70 in the delivered configuration, and to stiffen for deploying the prosthesis 70 at the desired implanting location.

As shown in FIGS. 28A-D, which have the outer sheath assembly 22 and the mid shaft assembly 20 of delivery system 10 removed for clarity, the modified distal section 120 can include the nose cone 28, an inner tube 1220, an outer tube 1240, and a pull wire 1260 connecting the nose cone 28 and the outer tube 1240. A distal end of the inner tube 1220 can be connected to the nose cone 28 by any method known in the art. A proximal end of the inner tube 1220 can be coupled directly or indirectly to the handle 14.

In some embodiments, the inner tube 1220 can be the nose cone shaft 30 of FIG. 2A with its distal portion modified as described herein to be bendable. The inner tube 1220 can be, for example, a metal hypotube with a lumen sized and configured to slidably accommodate a guide wire. In some embodiments, the inner tube 1220 can be a different tube than the nose cone shaft 30 of FIG. 2A and can have a lumen sized and configured to slidably accommodate both a guide wire and the nose cone shaft 30 of FIG. 2A. In some embodiments, the inner tube 1220 can be covered or encapsulated with a layer of ePTFE, PTFE, or other material so that an outer and/or inner surface of the inner tube 1220 is generally smooth.

As shown in FIGS. 28A-D, the inner tube 1220 can have a bendable and steerable distal portion 1222, the mechanics of which are further discussed below. The bendable distal portion 1222 in some embodiments can have a length of about ⅓" to about 1½". The bendable distal portion 1222 can have reduced rigidity, and thus increased flexibility, for bending due to perforations 1224 on a wall of the distal portion 1222 of the inner tube 1220. The particular patterns and/or formation of the perforations are not limiting. In the illustrated embodiment, the bendable distal portion 1222 comprises interconnecting diamond-shaped cells 1225 of substantially the same size, though size and shape variations may occur throughout and the diamond-shapes are simply one example and the particular size and shape is not limiting. The cells 1225 can be formed by laser cutting, or other means. In some embodiments, density of the perforations throughout the wall of the bendable distal portion 1222 can vary to provide varying flexibility throughout the bendable distal portion 1222. In some embodiments, the distal bendable section can include a Pebax catheter having a low value on a durometer scale. For example and not by way of limitation, the Pebax catheter can include a Pebax 55D or Pebax 35D. In some embodiments, the delivery system 10 may not use a guide wire or may have a separate lumen for the guide wire and thus a proximal end of the inner tube 1220 can be formed by a solid rod, such as a metal or plastic rod, attached to the bendable distal portion 1222.

In some embodiments, the outer tube 1240 can be a metal hypotube optimized for maximum flexibility and minimum strain while providing for structural rigidity. For example, the outer tube can be formed from stainless steel, though other materials can be used as well. In some embodiments, the outer tube 1240 can be covered or encapsulated with a layer of ePTFE, PTFE, or other material so that an outer and/or inner surface of the inner tube 1220 is generally smooth. The outer tube 1240 can have a lumen sized and configured to slidably accommodate the inner tube 1220. In some embodiments, the outer tube 1240 can be placed immediately within the inner retention shaft 42 described above and have an outer diameter configured to allow the outer tube 1240 to slide smoothly within the inner retention shaft 42. The outer tube 1240 can have a proximal end operably coupled to the handle 14. For example, the proximal end of the outer tube 1240 can extend into the handle 14. The sliding of the outer tube 1240 can be controlled by the steering knob/actuator 610 (shown in FIG. 1), which also control the bending of the mid shaft 50 so that the mid shaft 50 and the distal section 120 can be bent simultaneously. The outer tube 1240 can also be controlled by a different control mechanism so that the bending of the distal portion 120 can be controlled independent of the control of the mid shaft 50.

In order to bend the bendable distal portion 1222, a pull wire 1260 can be attached to the nose cone 28, either on its proximal end or on its inner surface. The pull wire 1260 can be made of stainless-steel including SS316, 304, or other suitable grades, Nitinol, or fiber threads including Dyneema rope, suture, or the like. The pull wire 1260 can in some embodiments have a diameter of about 0.008" to about 0.028". For example, the diameter of the pull wire 1260 can be 0.018". The pull wire 1260 can have a length that is substantially the same as the length of the bendable portion 1222 of the inner tube 1220. In the illustrated configuration, the pull wire 1260 is connected to a proximal end of the nose cone 28 and a distal end of the outer tube 1240. The pull wire 1260 can be connected to other parts of the nose cone 28 and/or the outer tube 1240 as well. Further, the pull wire 1260 can be connected to the nose cone 28 and the outer tube 1240 by any methods known in the art, such as welding.

As shown in FIG. 28A, the pull wire 1260 is taut when the distal end of the outer tube 1240 is near a proximal end of the bendable distal portion 1222 of the inner tube such that a shortest distance between the proximal end of the nose cone 28 and the distal end of the outer tube 1240 is substantially the same as the length of the pull wire 1260. As shown in FIG. 28B, the pull wire 1260 can be under tension when the outer tube 1240 is pulled proximally and away from the nose cone 28. The tension can cause the bendable distal portion 1222 of the inner tube 1220 to bend to the side of the pull wire 1260 because the shortest distance between the proximal end of the nose cone 28 and the distal end of the outer tube 1240 is limited by the length of the pull wire 1260. As shown in FIG. 28C, pushing the outer tube 1240 back toward its position as shown in FIG. 28C allows the bendable portion 1222 of the inner tube 1220 to straighten and the nose cone 28 to return to its position in FIG. 28A, that is, aligning with a longitudinal axis of the inner tube 1220. As shown in FIG. 28D, the pull wire 1260 is loose when the outer tube 1240 is pushed distally and toward the nose cone 28.

The modified distal section 120 having the solid outer tube 1240 and the inner tube 1220 with the bendable distal portion 1222 advantageously provides for a deformation of the distal section 120 of the delivery system 10, such as bending, as a force is applied to the modified distal section 120. Another advantage is that the distal section 120 is only flexible when needed, such as when steering the delivery system 10 through sharp corners of the patient anatomy. Described next are methods for enacting a force and thus causing the bending of the modified distal section 120 of the delivery system 10.

Whenever the distal section 120 of the delivery system 10 needs to make a turn, for example, at least when going through the inferior vena cava, the fossa ovalis, the left atrium and the right atrium, the user can then turn a knob on the handle 14 in order to cause bending of the bending distal portion 1222 of the inner tube, and thus the modified distal section 120 of the delivery system 10. A proximal force is applied by a steering knob to the proximal end of the outer tube 1240, which pulls the pull wire 1260 proximally. As described above and shown in FIG. 28B, because the shortest distance between the distal end of the outer tube 1240 and the proximal end of the nose cone 28 is limited by the length of the pull wire 1260, the bendable distal portion 1222 of the inner tube is bent as well, thereby deflecting the nose cone 28 to the side of the pull wire 1260. In some embodiments, the bendable distal portion 1222 can bend in more than one dimension, allowing 3-dimensional bending (and thus 3-dimensional steering). In some embodiments, the bendable distal portion 1222 of the inner tube can bend only in one direction, that is, to the side of the pull wire 1260. The delivery system 10 can be rotated so that the bendable distal portion 1222 of the inner tube can bend in a desired direction. Further, a number of different pull wires 1260 can be used to provide bending in different directions.

In some embodiments, the prosthesis 70 can be located at least partially proximal of the bendable distal portion 1222, for example, as shown in FIGS. 30A-D (except that the delivery system 10 of FIG. 30B has a bendable outer tube and a stiff inner tube). For example and not by way of limitation, the distal anchors 80 of the prosthesis 70 can at least partially overlap with the bendable distal portion 1222. Although not shown in FIGS. 28A-D, when the bendable distal portion 1222 of the inner tube is bent, the generally distally pointing distal anchors 80 of the prosthesis 70 that is loaded on the delivery system 10 can also bend to conform with the bending of the inner tube 1220 (shown in FIG. 30B). The bending of the generally distally pointing distal anchors 80 can advantageously reduce a longitudinal length of the prosthesis 70, thereby easing maneuvering of the prosthesis 70 along the delivery system 10. The prosthesis 70 can also press against an inner surface of the outer sheath assembly 22, thereby forcing the outer sheath assembly 22 to bend along with the inner tube 1220. A user may further manipulate the knob to create an even greater bend in the distal section 120 of the delivery system 10 if needed. Further, the user may combine the bending of the mid shaft 50 and the distal section 120 to place the prosthesis 70 in the proper location. This can advantageously allow delivery of a prosthesis 70 to an in situ implantation site, such as a native mitral valve, via a wider variety of approaches, such as a transseptal approach, or other approaches requiring steering the delivery system through the complex areas of the heart in order to place a replacement mitral valve in line with the native mitral valve.

As shown in FIG. 28C, when the proximally pulling force on the pull wire 1260 is removed, the bendable distal portion 1222 of the inner tube can translate back (e.g., "spring back") to its original position. In some embodiments, this can occur at least partially due to the material being superelastic (e.g., nitinol) of the inner tube 1220. In some embodiments, a significant pulling force can be applied to initiate bending, and releasing the pulling force can make the inner tube return to its normal shape, which can be straight or slightly curved. This can be advantageous because, as discussed below, the pull wire 1260 will not be compressed, thus avoiding kinks. In some embodiments, the bendable distal portion 1222 of the inner tube 1220 will remain in the bent configuration even upon removal of the force and a second pull wire (not shown) can be used, located in a different portion, e.g. diametrically opposite from the first pull wire 1260, of the bendable distal portion 1222, to straighten the inner tube 1220. The second pull wire can thus allow for two-way steering of the bendable distal portion 1222. The user can operate both pull wires independently, or they can operate in tandem with one another, with forces of the same or different magnitudes, to produce the desired bend in the bendable distal portion 1222 and to straighten the bendable distal portion 1222 to its origin position. For example, there may be a knob on the handle.

After the delivery system 10 has reached the desired location, for example, across the mitral valve, the user can manipulate the knob to push the outer tube 1240 distally. As described above, the pull wire 1260 can relax because the distance between the distal end of the outer tube 1240 and the proximal end of the nose cone 28 is now smaller than the length of the pull wire 1260. The pull wire 1260 can be configured to have sufficient axial rigidity such that when the outer tube 1240 is pushed distally, the pull wire 1260 can fold with two ends of the pull wire 1260 next to each other, thus avoiding kinks. The outer tube 1240 can be configured to at least partially surround the bendable distal portion 1222 of the inner tube and provide structural rigidity to the distal section 120 of the delivery system 10. The stiffened distal section 120 can then withstand the proximally pulling force on the nose cone 28 in the controlled deployment of the distal anchors 80 described below.

FIGS. 29A-D illustrate an alternate embodiment where the outer tube 1240 can be replaced by a hollow needle 1240' and the inner tube 1220 (or an inner shaft for delivery systems that do not require guide wire(s) for advancing to the surgical site) can have a nose portion 28' with reduced size in a distal section 120' of the delivery system 10. FIGS. 29A-D also have the outer sheath assembly 22 and, the mid shaft assembly 20 removed for clarity. The distal section 120' of FIGS. 29A-D can have features of the distal section 120 of FIGS. 28A-D except as described below. Accordingly, features of the distal section 120' of FIGS. 29A-D can be incorporated into features of the distal section 120 of FIGS. 28A-D and features of the distal section 120 of FIGS. 28A-D can be incorporated into features of the distal section 120' of FIGS. 29A-D.

As shown in FIGS. 29A-D, the needle 1240' can have a pointed tip 1242 at its distal end. The pointed tip 1242 can have a length of about ½" to about 1½".

The nose portion 28' in FIGS. 29A-D can have a uniform outer diameter over a length from a proximal end to a distal end so that the nose portion 28' can be cylindrical instead of conical. The nose portion 28' is sized and configured to be slidably accommodated in a lumen of the needle 1240'.

The pull wire 1260 can be connected at the pointed tip 1242 of the needle and at the distal end of the nose portion 28'. A person of ordinary skill in the art will appreciate that the pull wire 1260 can be connected to other locations on the needle 1240' and the nose portion 28'.

As shown in FIG. 29A, when the delivery system 10 is being steered through the patient anatomy, the needle 1240' can be pulled proximally so that the pointed tip 1244 of the needle is proximal of the nose portion 28'. In the illustrated embodiment, a distal end of the pointed tip 1242 is next to a bendable portion 1222 of the inner tube 1220. This configuration prevents the pointed tip 1242 from being exposed and causing trauma, e.g. puncturing, body tissue of the patient as the delivery system 10 is advanced through the patient anatomy.

FIG. 29B illustrates proximal retracting of the needle 1240' by a force in the proximal direction to cause the pull wire 1260 to bend the inner tube 1220 at the bendable portion 1222. FIG. 29C shows that releasing the inner tube 1220 from the proximal running force causes the inner tube 1220 to straighten and return to its original position shown in FIG. 29A.

When the delivery system 10 needs to puncture the body tissue, such as when crossing the septum wall, the needle 1240' can be advanced distally until the pointed tip 1242 is distal of the nose portion 28' as shown in FIG. 29D. The bendable portion 1222 of the inner tube can be stiffened by a wall of the needle 1240' and the pointed tip 1242 of the needle can be exposed. The exposed pointed tip 1242 can thus puncture the body tissue, e.g. the septum wall, without the distal section 120' of the delivery system 10 buckling at the bendable portion 1222 of the inner tube.

FIGS. 29E-H illustrate an alternate embodiment with hollow needle 1240' and a rigid inner tube 1220 (or an inner shaft for delivery systems that do not require guide wire(s) for advancing to the surgical site). In FIGS. 29E-H, the inner tube/rod 1220 does not have a bendable distal portion and can be rigid throughout the inner tube/rod 1220. At a distal end, the rigid inner tube/rod 1220 can be connected by the pull wire 1260 to the needle's distal tip 1242. The needle 1240' can also have a plurality of slits 1244 running only in the circumferential direction on a portion that is immediately distal of the pointed tip 1242. In some embodiments, the plurality of slits 1244 can be laser cut, but the particular method is not limiting. The circumferentially running slits 1244 allow the needle 1240' to have some flexibility under radial forces but to maintain its rigidity under forces parallel to a longitudinal axis of the needle 1240'.

Initially, the rigid inner tube 1220 can be located within a lumen of the needle 1240', as shown in FIG. 29E, and can be proximal to the plurality of slits 1244. The proximal location of the rigid inner tube/rod 1220 can have the advantage of not hindering bending of the needle 1240' at the plurality of slits 1244 when desired, for example and not by way of limitation, during maneuvering of the delivery system 10 in the patient's anatomy. The circumferentially running slits 1244 allow the needle 1240' to deflect when being pulled by the pull wire 1260, which can be connected to a distal end of the rigid inner tube 1220, as shown in FIG. 29F. When the rigid inner tube 1220 is pulled proximally, the pull wire 1260 provides a force to bend the needle 1240' as shown in FIG. 29F. When the rigid inner tube 1200 is moved back distally, the needle 1240' can extend back to the original position as shown in FIG. 29G. Further, when penetration of a patient's anatomy is desired, the rigid inner tube/rod 1220 can be advanced distally to overlap at least partially with and stiffen the plurality of the slits 1244 on the needle 1240', as shown in FIG. 29H. The pointed tip 1242 can thus puncture the body tissue without buckling of the needle 1240'.

In yet another embodiment, the inner tube 1220 can be replaced by a needle (not shown) in the modified distal section 120 of FIGS. 28A-D. The needle can have features of the inner tube 1220 except as described below. Accordingly, features of the needle can be incorporated into features of the inner tube 1220 and features of the inner tube 1220 can be incorporated into features of the needle. The needle can have a pointed tip that is distal of a bendable portion. When flexing of the needle is desired, such as when steering the delivery system 10 through complex patient anatomy, the outer tube 1240 can be retracted proximally under a force in the proximal direction. As has described above, the release of the outer tube 1240 from the proximal force can cause the needle to straighten. Further, the outer tube 1240 can be advanced distally to at least partially overlap with the bendable portion of the needle so that the distal section of the delivery system is stiff when the pointed tip of the needle punctures the body tissue to advance the delivery system.

FIGS. 30A-D illustrate an alternate non-limiting embodiment of the distal section 120" of the delivery system 10 that utilize the flex and stiff principle described herein, such as with respect to FIGS. 28A-D, but with the outer shaft being bendable instead of the inner shaft. FIGS. 30A-D also show the prosthesis 70 loaded on the distal section 120" of the delivery system, which will be described later Like FIGS. 28A-D, FIGS. 30A-D have the outer sheath assembly 22 and the mid shaft assembly 20 removed for clarity. The distal section 120" of FIGS. 30A-D can have features of the distal sections 120, 120' of FIGS. 28A-D and/or FIGS. 29A-D except as described below. Accordingly, features of the distal section 120" of FIGS. 30A-D can be incorporated into features of the distal sections 120, 120' of FIGS. 28A-D and FIGS. 29A-D and features of the distal sections 120, 120' of FIGS. 28A-D and FIGS. 29A-D can be incorporated into features of the distal section 120" of FIGS. 30A-D.

As shown in FIGS. 30A-D, the distal section 120" of the delivery system can have the distal end of the bendable distal portion 1245 of the outer tube 1240" attached to the proximal end of the nose cone 28. In some embodiments, the outer tube 1240" can be the nose cone shaft 30 of FIG. 2A with its distal portion modified as described herein to be bendable. The bendable distal portion 1245 shown in FIGS. 30A-D comprises a cut-out slot 1246 such that a cross section at the bendable distal portion 1245 does not form a complete circle but is a partial circle. The partial circle can be about ½ of a full circle to about ¾ of a full circle. The size of the partial circle is not limiting. The slot 1246 can have a length of about ⅓" to about 1½".

The inner tube 1220" shown in FIGS. 30A-D can be made of the same material as the outer tube 1240 of FIGS. 28A-D or other materials optimized for maximum flexibility and minimum strain while providing for structural rigidity. The inner tube 1220' can pass through a lumen of the outer tube 1240. The inner tube 1220" can connect to one end of the pull wire 1260 at its distal end. The other end of the pull wire 1260 can be connected to the proximal end of the nose cone 28. The inner tube 1220" can also be operably coupled at its proximal end to the handle 14 such that a knob (not shown) or equivalent control mechanism on the handle 14 can cause the inner tube 1220" to slide both proximally and distally from its original position shown in FIG. 30A. When assembled, the inner tube 1220" can be oriented with respect to the outer tube 1240" such that the pull wire 1260 is next to the slot 1246 instead of being next to the partial circle. Placing the pull wire 1260 on the side of the slot 1246 can cause the bendable distal portion 1245 of the outer tube 1240" to bend on the side of the slot 1246, as shown in FIG. 30B, by pulling distally on the inner tube 1220". Placing the pull wire 1260 on the side of the partial circle can cause the bendable distal portion 1245 of the outer tube 1240" to bend on the side of the partial circle, that is, bending in an opposite direction. Accordingly, in some embodiments, the knob can further allow rotation of the inner tube 1220" to toggle the two bending directions of the outer tube 1240". One of ordinary skill in the art will appreciate that in the distal section with the bendable inner tube and the stiff outer tube, the inner tube can also have a slot at the bendable portion and the direction of bending can also be controlled by the orientation of the outer tube and the pull wire with respect to the slot.

When the prosthesis 70 is ready for deployment, as shown in FIGS. 30C-D, the inner tube 1220" can be advanced distally to overlap with the slot 1246 and stiffen the distal section 120" of the delivery system such that the nose cone 28 can be pulled proximally without the outer tube 1240" buckling at the bendable portion 1245.

Described next is the controlled partial deployment of a prosthesis 70 by the delivery system 10. As has been described, the distal anchors 80 can be restrained in the delivered configuration by the outer sheath assembly 22. Accordingly, when the outer sheath 22 is withdrawn proximally, the distal anchors 80 can flip positions to a deployed configuration (e.g., pointing generally proximally). The deployed distal anchors 80 can extend between at least some of the chordae tendineae to provide tension on the chordae tendineae. Flipping of the distal anchors 80 may happen suddenly and in an uncontrollable manner. The distal anchors 80 may catch at least some of the chordae tendineae during the sudden flipping. Accordingly, it can be advantageous to have mechanisms for controlled deployment of the distal anchors 80 as the distal anchors 80 flip from pointing generally distally to pointing generally proximally.

FIGS. 30A-D and 31-32 show the modified distal section 120" of the delivery system 10 loaded with a replacement mitral valve prosthesis 70 or another mitral valve prosthesis 70'. The outer sheath assembly 22 and the mid shaft assembly 20 have also been removed from FIGS. 30A-D and 31-32 for clarity. Further, only two distal anchors 80 are shown in FIGS. 30A-D in order to show details of the inner tube 1220" (shown in FIGS. 30C-D only), the outer tube 1240", and the pull wire 1260, which will be blocked by the distal anchor 80 in FIGS. 30A-D.

Figure 31:
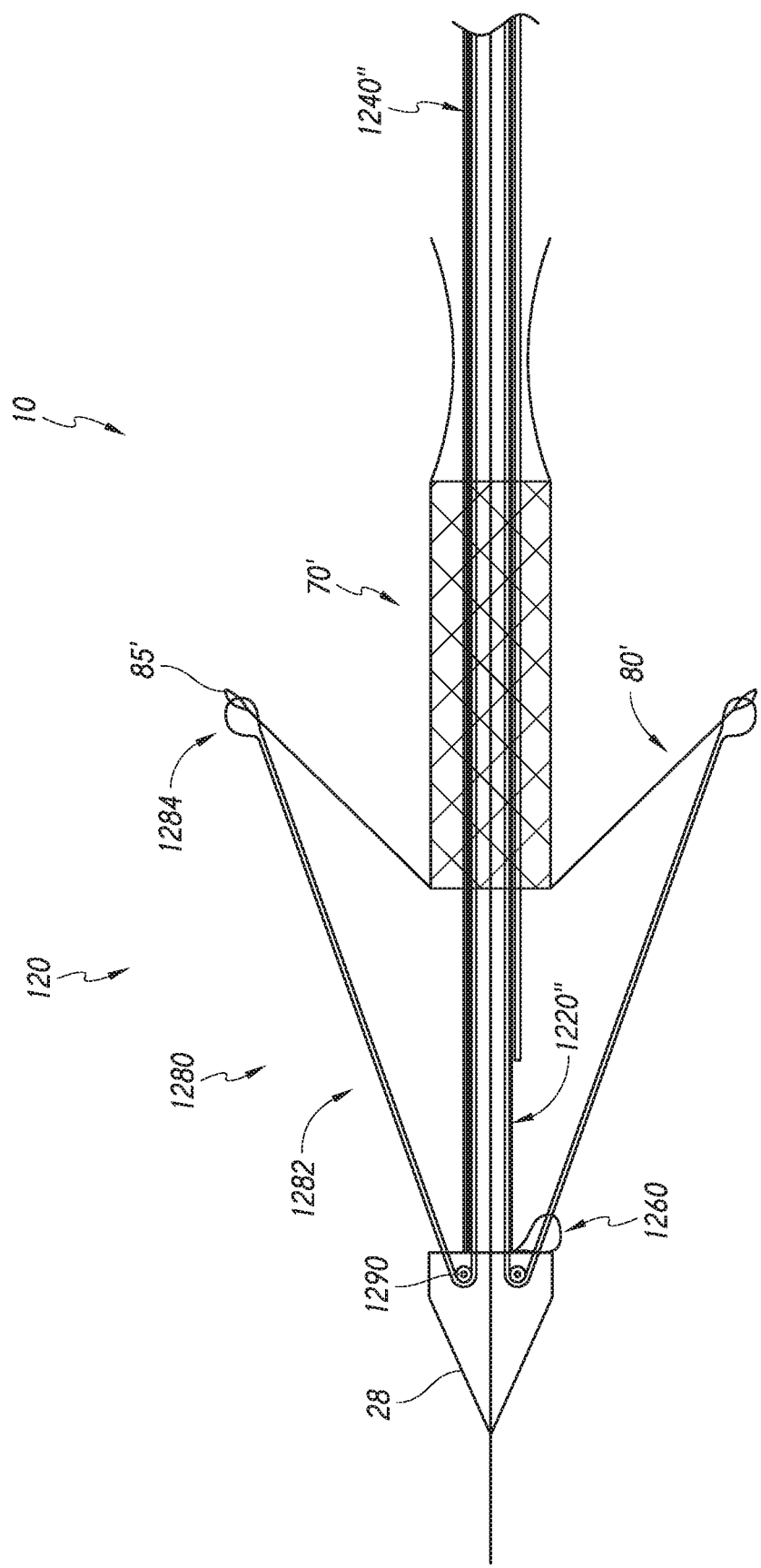
FIG. 31 shows a schematic representation of an embodiment of a distal end of a delivery system with the outer sheath assembly and the mid shaft assembly removed and including an outer tube with a bendable portion and loaded with a schematic representation of a valve prosthesis.

As described above, the distal anchors 80 of the prosthesis 70 point generally distally when the prosthesis 70 is in the delivered configuration because the distal anchors 80 are restrained from flipping to their preset shapes by the outer sheath 22. FIGS. 30A-D and 31-32 show a plurality of tethers (e.g., pull wires or cables) 1280 for restraining the distal anchors 80 in addition to the outer sheath 22. Although FIGS. 30A-D and 32 show only two tethers 1280 for clarity, one of ordinary skill in the art may appreciate from the disclosure herein that every distal anchor 80 can be connected to a tether 1280. For example, the delivery system 10 can have 12 tethers 1280 if the prosthesis 70 has 12 distal anchors 80. For example, FIGS. 30A-D and 32 show the delivery system 10 loaded with the prosthesis 70 and the delivery system 10 can thus have twelve tethers 1280 for the twelve distal anchors 80. FIG. 31 shows the delivery system 10 loaded with a different valve prosthesis 70' having two distal anchors 80' and the delivery system 10 can thus have only two tethers 1280.

Figure 32:
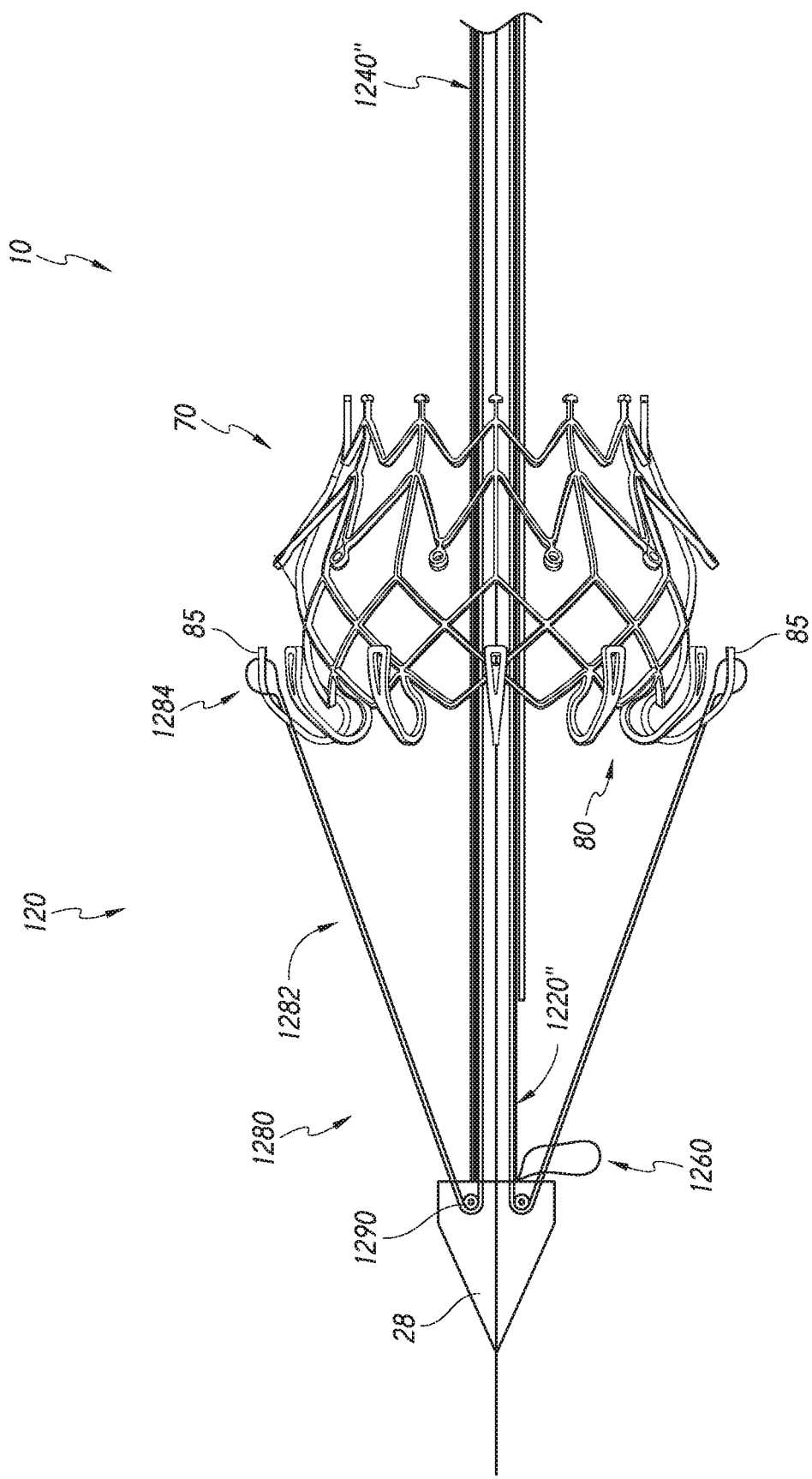
FIG. 32 show a schematic representation of an embodiment of a distal end of a delivery system with the outer sheath assembly and the mid shaft assembly removed and including an outer tube with a bendable portion and loaded with the valve prosthesis.

As more clearly shown in FIGS. 31-32, each tether 1280 can comprise a pull wire or cable folded into a double-strand 1282 by looping the pull wire through the distal anchors 80, 80' so that both loose ends of the pull wire end at a proximal end of the double strand 1282. The proximal end can be operably coupled to the handle 14 at a control mechanism, such as a tether knob. As shown in FIG. 32, the tether 1280 can be looped through eyelets 85, 85' on distal ends of the distal anchors 80, 80', forming a continuous or looped end 1284 of the double strand 1282. In some embodiments, the eyelets 85, 85' may not be available for the tether 1280 to loop through. For example, the eyelets 85, 85' may be occupied by a suture or wire used to sew a valve body onto the prosthesis 70, 70'. In another example, cushions (not show) can wrap around one or more of the distal ends of the distal anchors 80, covering up the eyelets 85. In those embodiments, the tether 1280 can be looped through a separate eyelet (not shown) next to the eyelets 85 on the distal ends of the distal anchors 80. In other embodiments, the cushions can each have one or more holes on both sides of the eyelet 85 that is covered up by the cushion so that the tether 1280 can pass through these holes and the eyelet 85. The tether 1280 can be made of metal, fabric, plastic, or other materials and a diameter of the pull wire or cable is not limiting.

The nose cone 28 further comprises a pulley 1290 for each tether 1280. For example and not by way of limitation, the pulley 1290 can be a pin nailed on the nose cone 28 or on an internal component of the nose cone 28. The double strand 1282 is pulled taut by the generally distally pointing distal anchors 80, 80', which tend to spring back to point generally proximally due to their preset shapes, and the tether knob on the handle 14, with a change of direction of the double strand 1282 at the pulley 1290. Before the controlled deployment of the distal anchors 80, 80', such as shown in FIGS. 30A-C, a length of the double strand 1282 (more clearly shown in FIGS. 31-32) between the continuous end 1284 and the pulley 1290 is at a minimum. Accordingly, distal movement of the proximal end of the double strand 1282 can cause the taut double strand 1282 to move along part of a circumference of the pulley 1290 and then move proximally after making a turn at the pulley 1290, increasing the length of the double strand 1282 between the continuous end 1284 and the pulley 1290. The increased length of the double strand 1282 can gradually expand the distal anchors 80, 80' until they reach a fully deployed configuration. In some embodiments, the tether 1280 can be used to pull back the deployed distal anchors 80, 80' and to straighten the distal anchors 80, 80'. For example, the tether knob (not shown) on the handle can have mechanisms allowing the tether 1280 to be retracted toward the handle. The inner shaft retention shaft 42 can be pushed distally to cover the distal anchors 80, 80' in the delivered configuration in order to recapture the prosthesis 70, 70'. Recapturing the prosthesis 70, 70' can advantageously allow the prosthesis 70, 70' to be repositioned. In some embodiments, the recapturing can be repeated multiple times until a desired position of the prosthesis 70, 70' can be achieved.

As described above, the stiff inner tube can be advanced distally to overlap with the bendable portion of the outer/inner tube, thereby preventing the distal section 120, 120', 120" from buckling when the nose cone 28 or the nose portion 28' is pulled proximally by the tethers 1280. In the illustrated embodiment, the pulleys 1290 are on a side wall of the nose cone 28 near its proximal end. In other embodiments, the pulley 1290 can be on a side wall of an internal component of the nose cone 28. Thus, the pulley 1290 can be internal or external of the nose cone 28. Locations of the pulleys 1290 on the nose cone 28 are not limiting. One of ordinary skill in the art may also appreciate that other methods of sliding the double strand 1282, such as via a sliding channel on the nose cone 28, can likewise translate the distal movement of the loose end of the double strand 1282 to the proximal movement of the continuous end 1284 and thus the expansion of the distal anchors 80, 80'.

After the distal anchors 80, 80' are fully deployed, as shown in FIGS. 30D and 31-32, the two loose ends of the pull wire or cable can be released from the tether knob on the handle 14. One of the released loose ends can be pulled proximally. The other loose end can follow the pulled loose end by first moving distally to the pulley 1290, then moving proximally toward the eyelet 85, 85', then moving back toward the pulley 1290 after clearing the eyelet 85, 85' and releasing the valve prosthesis 70, 70', and finally moving proximally again at the pulley 1290 to be retracted from the delivery system 10.

Wire Balloons for Chordae Avoidance

During the delivery procedure, a delivery system is guided through the mitral apparatus, typically, though not necessarily, on a guide wire. However, there is a risk that the guide wire will go in between chordae of the heart during implantation. If this occurs, the delivery system may have difficulty being positioned correctly and might get stuck which can cause procedure failure and possibly cause serious damage to the patient.

The common method to mitigate this risk is using a balloon catheter on a guide wire. One option is to pass through the mitral valve with the balloon deflated, inflate it and pull back the balloon to see if it gets stuck on chordae. If it does, the balloon and guide wire are pulled back and more attempts are made until successful. A second option is to pass through the mitral apparatus while the balloon is inflated so it cannot pass between chordae and the balloon catheter is pushed through the mitral valve, avoiding the chordae and ensuring a safe trajectory. After verification the balloon catheter is pulled out and the guide wire is left in place. The delivery system is then advanced on the guide wire to start the procedure.

However, the use of the inflatable balloon can be cumbersome and difficult since the balloon tends to be pushed by the blood flow and go in a direction not specified by the physician due to the there being no way for blood to pass through the balloon. Further, balloons are typically made of very flexible material and thus can be very unstable in the body. Moreover, the balloon catheter is an extra device that needs to be used during implantation, and requires further equipment such as a syringe and saline. Accordingly, various balloon devices and methods are commonly used. None of them are particularly convenient or ensure a stable and straight forward application.

As a potential to alleviate the problems with the previously used balloons, disclosed herein are embodiments of a wire balloon. FIGS. 33A-D illustrate such embodiments of a wire balloon 3300. Embodiments of a wire balloon can be used for a delivery system, such as the delivery system 10 of FIG. 1. The wire balloon can be used in conjunction with the delivery systems disclosed above. Further, while this section is discussed with respect to prosthesis 70 and delivery system 10, it will be understood that it can be used with respect to prosthesis 1010 and delivery system 5000, or other prostheses and delivery systems.

Figure 33A:
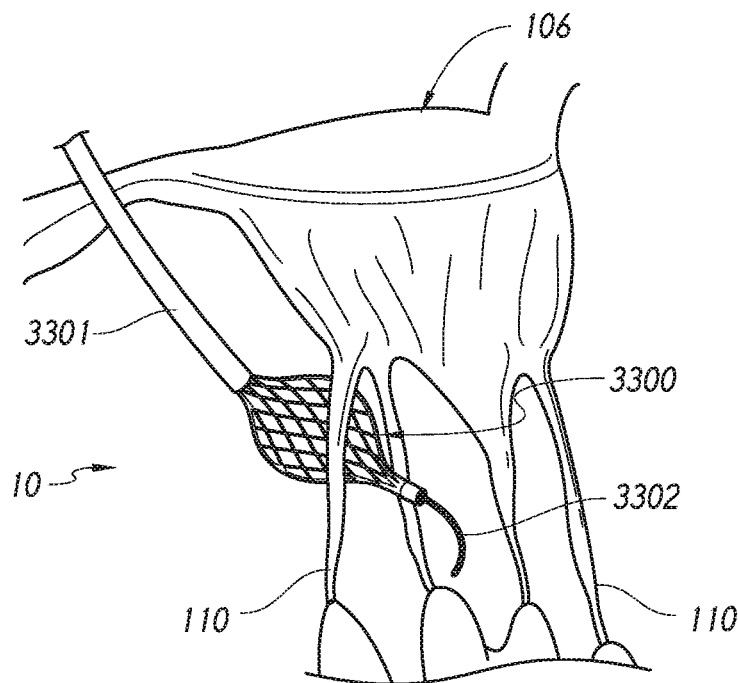
FIGS. 33A-D illustrates embodiments of a wire balloon.

In some embodiments, the wire balloon 3300 can be used in a similar manner as a standard balloon to avoid chordae 110 by following a guide wire 3302, as shown in FIG. 33A. For example, the wire balloon 3300 can be expanded in the left ventricle to avoid the chordae 110 so that the guide wire 3302 can be located in the proper location for delivery of the delivery system 10.

In some embodiments, the wire balloon 3300 can be a pre-shaped formation of wires or laser cut tube/wire. Other self-expanding structure can be used as well. In some embodiments, the wire balloon 3300 can be made of a material that is less flexible than a standard guide wire balloon, providing a user more control. The wire balloon can be shaped as a balloon, sphere, rugby ball, football, or similar shape and the particular shape does not limit the disclosure. Additionally, the wire balloon 3300 can be configured to have a compressed and an expanded position. In some embodiments, the wire balloon 3300 can self-expand to the expanded position once released from any constraints. In some embodiments, a user can manually expand the wire balloon 3300. In some embodiments, the wire balloon 3300 can have a central lumen for a guide wire 3302 to pass through.

The wire balloon 3300 can include a number of through holes/apertures so that blood can pass through the wire balloon 3300, which can improve positioning of the balloon 3300 during blood flow. For example, as the wire balloon 3300 has a number of access points through the wire balloon 3300, it will not be pushed/shifted by the blood flow as much as a typical balloon since the blood can flow through it. Moreover, application of the wire balloon 3300 into the patient can be easier since there is no need for the use of saline to inflate the balloon, and the wire balloon 3300 can self-expand.

The wire balloon 3300 can be made of any number of materials, such as polymers, plastics, or metals. Metals which are typically used for thin wires can be advantageous in the manufacturing of the wire balloon 3300. In some embodiments, the wire balloon 3300 can be made of Nitinol.

Thus, the wire balloon 3300 can be more rigid and controllable than a standard inflatable balloon. The wire balloon 3300 can be made of a metallic net or frame into a sphere, rugby ball, or similar shape. The wire balloon 3300 can be heat-shaped to form the specific design, though the particular method is not limiting.

In some embodiments, the wire balloon 3300 can be compressed into a cover tube 3301 for deployment. Thus, the wire balloon 3300 can be pulled into the cover tube 3301 for crimping and encapsulation or pushed out for expansion to a preset shape. In some embodiments, the wire balloon 3300 can automatically expand to its expanded position once released from the cover tube 3301. In some embodiments, the wire balloon 3300 can be pushed out of the cover tube 3301, such as by a hypotube or shaft that can be connected or disconnected from the wire balloon 3300. In some embodiments, the cover tube 3301 can be retracted and the wire balloon 3300 can remain in the same location to expand the wire balloon 3300.

Figure 33B:
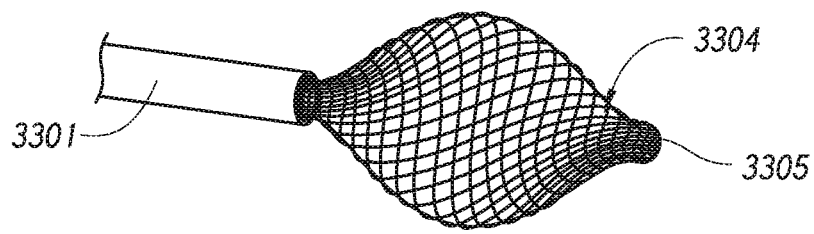

FIG. 33B illustrates a wire bundle shape balloon 3304. A number of wires can be twisted or woven and pre shaped, such as by heat, to the particular shape, such as the spherical shape shown in FIG. 33B. The particular shape is not limiting. In some embodiments, the wires can be connected at the tip at the distal end 3305 of the wire bundle shape balloon 3304 to create an atraumatic tip as shown in FIG. 33B. The wires can further be connected at a proximal tip and be connected to a rod/shaft for actuation at the proximal end of the cover tube 3301. As shown, the wire bundle shape balloon 3304 can have a number of passages for blood to flow through.

Figure 33C:
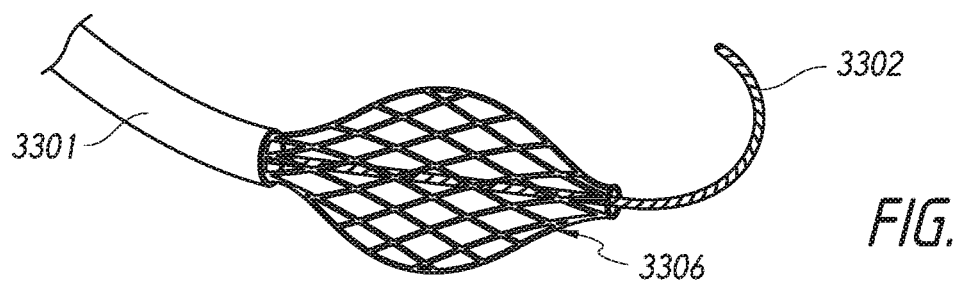

FIG. 33C illustrates a laser-cut tube balloon 3306. This laser-cut tube balloon 3306 can be cut as a frame and expanded to a spherical shape and heat set in the expanded form. In some embodiments, the laser-cut tube balloon 3306 can be made of a thin hollow Nitinol tube cut into the particular shape having the apertures as shown in FIG. 33C. A guide wire 3302 can be located inside the balloon 3306 in a central lumen so once the passage procedure is done the laser-cut tube balloon 3306 is pulled out and the delivery procedure can start on the existing guide wire 3302 with no further exchange.

Figure 33D:
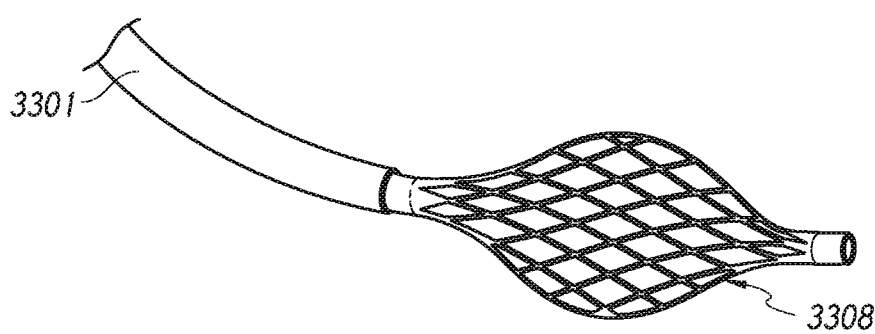

FIG. 33D illustrates a laser cut wire balloon 3308. This can be similar to the laser cut tube balloon 3306 of FIG. 1C, but made of one wire that is cut and shaped to a frame. Application of the laser cut wire balloon 3308 can be similar to that of the wire bundle shape balloon 3304 of FIG. 1B.

Transformable Nosecone

A nose cone is one of the basic components of a delivery system and is typically tapered to facilitate atraumatic passage through a patient's vasculature and heart. It can be conical in shape to enable smooth transition of the delivery system within the anatomy. However, there may be difficulty in removing the nose cone, specifically when needed to retrieve back through an already deployed implant or when passing through body structures.

FIGS. 34-37 illustrate embodiments of a "transformable nose cone" which can be incorporated into the above-disclosed delivery system 10. Further, while this section is discussed with respect to prosthesis 70 and delivery system 10, it will be understood that it can be used with respect to prosthesis 1010 and delivery system 5000, or other prostheses and delivery systems. This nose cone can replace the nose cone 28 discussed in detail above. Advantageously, the nose cone can mitigate the risk of difficult implantation, minimize damage to implant performance, and reduce negative impact to implant position.

The transformable nose cone can generally have two configurations. A first configuration is the active (or on/expanded) configuration. In this configuration the nosecone can be in its full size, e.g., the inflated size, and can serve the same purpose as a conventional nose cone. A second configuration is the inactive (or off/deflated) configuration. Here, the nosecone can collapse or "disappear" by a reduction in its diameter, and thus its overall profile, allowing it to be more easily withdrawn through a deployed prosthesis 70. Thus, the diameter of the nose cone in the active configuration is greater than the diameter of the nose cone in the inactive position. For example, the diameter of the inactive nose cone can be ½, ⅓, ¼, ⅕, ⅙, 1/7, or ⅛ of the diameter of the active nosecone. In some embodiments, the diameter of the inactive nose cone can be less than ½, ⅓, ¼, ⅕, ⅙, 1/7, or ⅛ of the diameter of the active nosecone. Further, the inactive configuration can be less stiff than the active configuration.

Thus, the nose cone can act as an atraumatic nose cone during delivery of a prosthesis 70, but with the additional ability to be deflated/collapse (and then re-inflated and re-deflated if needed) during the delivery procedure. The transformation of the nose cone from active to inactive can effectively provide a reduced stiff section and smaller profile for ease of withdrawal.

In some embodiments, the nose cone 3400 can be made of a polymer/plastic/rubber (e.g., balloon-like) as shown in FIG. 34. It can then be inflated/deflated by adding or removing saline (though other liquids and/or gasses can be used as well), which can be delivered from the handle 14 at the proximal end of the delivery system 10, such as through the nose cone shaft 30. This can be done with or without a radiopaque additive. For example, the nose cone 3400 can be inflated with a radiopaque liquid (such as saline with dye) to enable fluoroscopic control of the nosecone state, such as the degree of inflation/collapse). Similarly, liquid can be removed from the nose cone 3400 to reduce the diameter.

In some embodiments, the nose cone 3402 can be made of a shape-memory material, such as Niti Mesh, and covered in fabric as shown in FIGS. 35A-B. It can then be "activated" by pushing and pulling its distal tip while holding its proximal end, or vice versa (e.g., holding the distal tip while actuating the proximal end). For example, the nose cone 3402 can be attached to a pull wire 3404 that can be attached to a knob (or other actuator) in the handle 14. When the pull wire 3404 is activated (e.g., pulled proximally), it can pull on a proximal end of the nose cone 3402 thereby stretching it and compressing it. Upon release of the pull wire 3404 the nose cone 3402 can return to its standard size. In some embodiments, release allows the nose cone 3402 to automatically expand. In some embodiments, a force is used to re-expand the nose cone 3402. In some embodiments, the pull wire 3404 can be attached to the distal end of the nose cone 3402. A proximal force can be applied to pull back on the distal end to expand the nose cone 3402, and release of the force can cause the nose cone 3402 to extend forward and reduce the diameter. In some embodiments, radiopaque markers can be used to indicate the nose cone 3400 position using fluoroscopy.

Figure 36A:
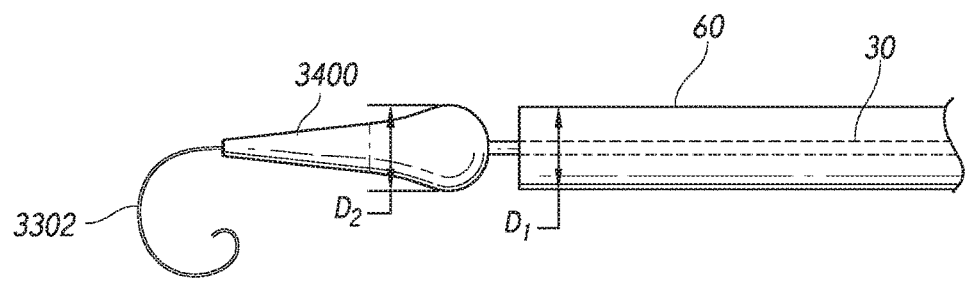
FIGS. 36A-B illustrate a transformable nosecone in an inflated and deflated position.
Figure 36B:
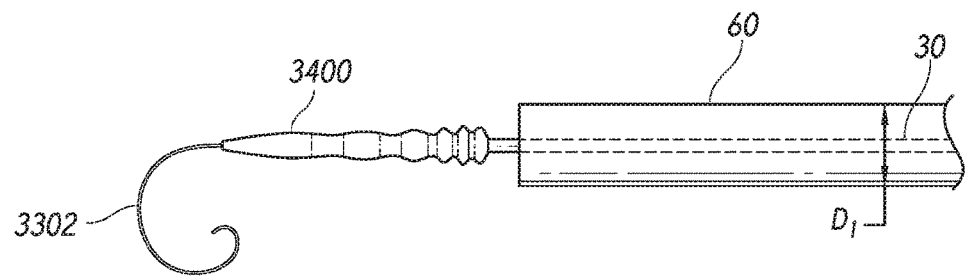
Figure 37:
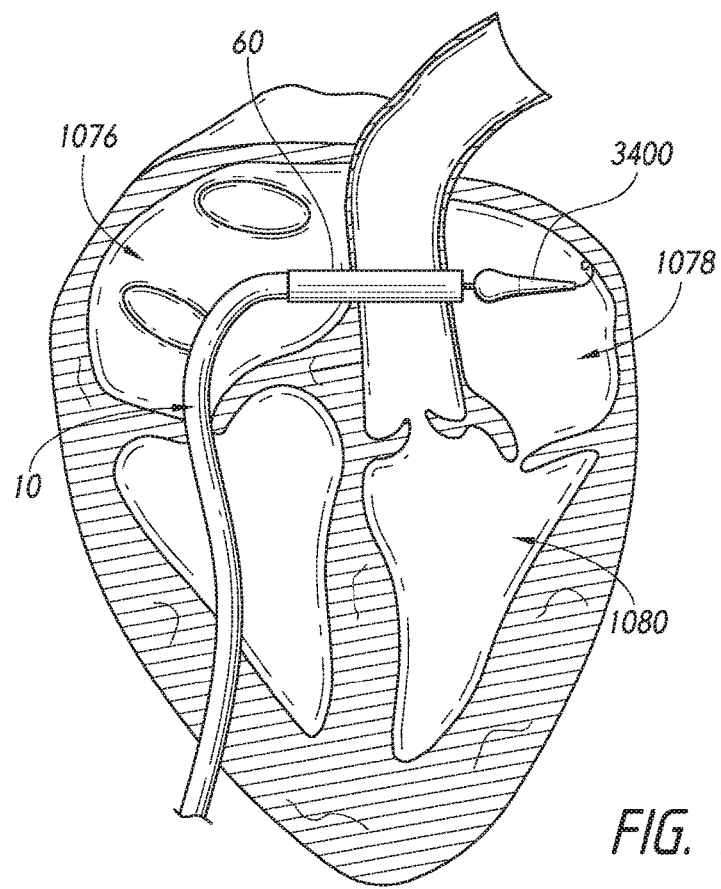
FIG. 37 illustrates an embodiment of a transformable nosecone in a transseptal delivery approach.

FIG. 36A illustrates the nose cone 3400 in the inflated position where FIG. 36B illustrates the nose cone 3400 in the deflated position. The active configuration can serve to facilitate atraumatic delivery of the delivery system 10 through a patient's vasculature and heart, specifically antegrade and retrograde crossing of native structures such as the septum and native mitral valve. The inactive configuration serves to facilitate retrieval, primarily by reducing the nosecone profile and therefore easing nose cone retraction through the deployed valve. Further, the ability to shrink the nose cone 3400 can be particular advantageous for transseptal crossing, where the native anatomy may introduce significant obstacles to delivery and retrieving the delivery system 10. For example, the delivery system 10 must first cross the septum, maneuver down to the left ventricle 1078 without getting stuck in the left atrial appendage (shown in FIG. 37), cross the native valve and then retrieved back through the deployed implant. The reduced stiff section of the nose cone eases delivery of the device during maneuvering.

Transseptal Steerability

Figure 38:
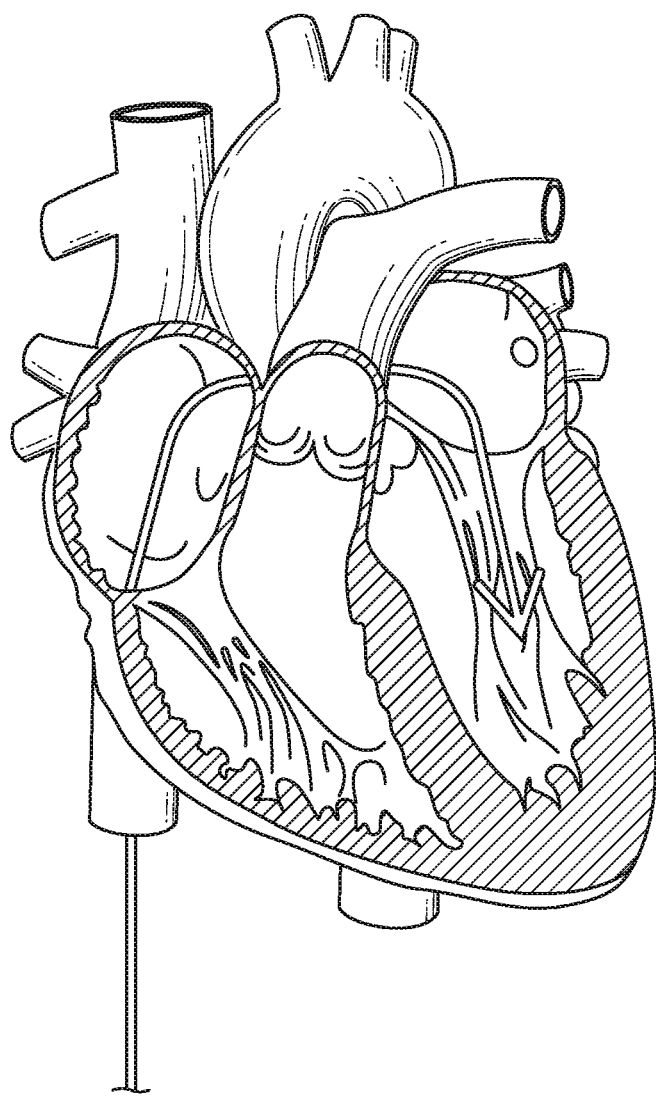
FIG. 38 illustrates a schematic of a transseptal delivery approach for mitral valve replacement.

Transseptal mitral valve replacement can utilize complicated maneuvers in order to overcome the anatomical limitations which include the fossa ovalis (FO) height above the mitral plane and the left atrium dimensions (LA). The fossa ovalis is a depression of the right atrium of the heart. The longer the implant is, the more challenging it can be to maneuver it. FIG. 38 illustrates the transseptal approach which passes through the following route: femoral vein access, inferior vena cava, right atrium, septum penetration through fossa ovalis, left atrium, and final position through the mitral valve into the left ventricle.

Figure 39:
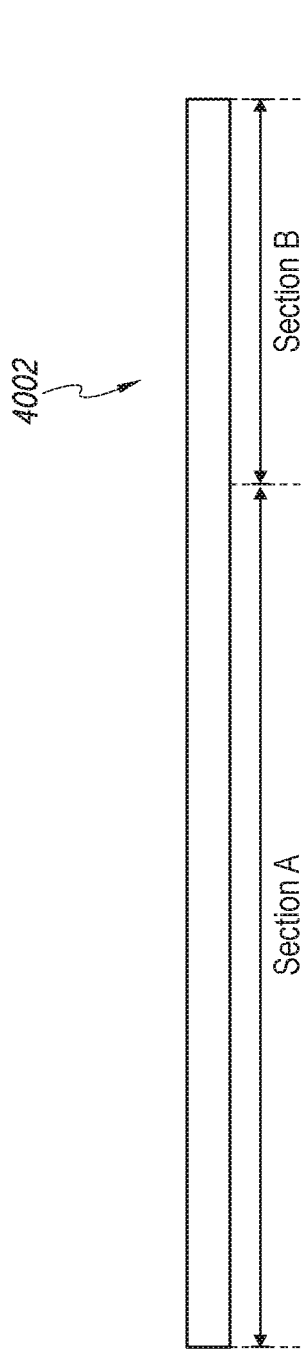
FIG. 39 illustrates portions of a delivery system configured for use in a hinging delivery approach.
Figure 40:
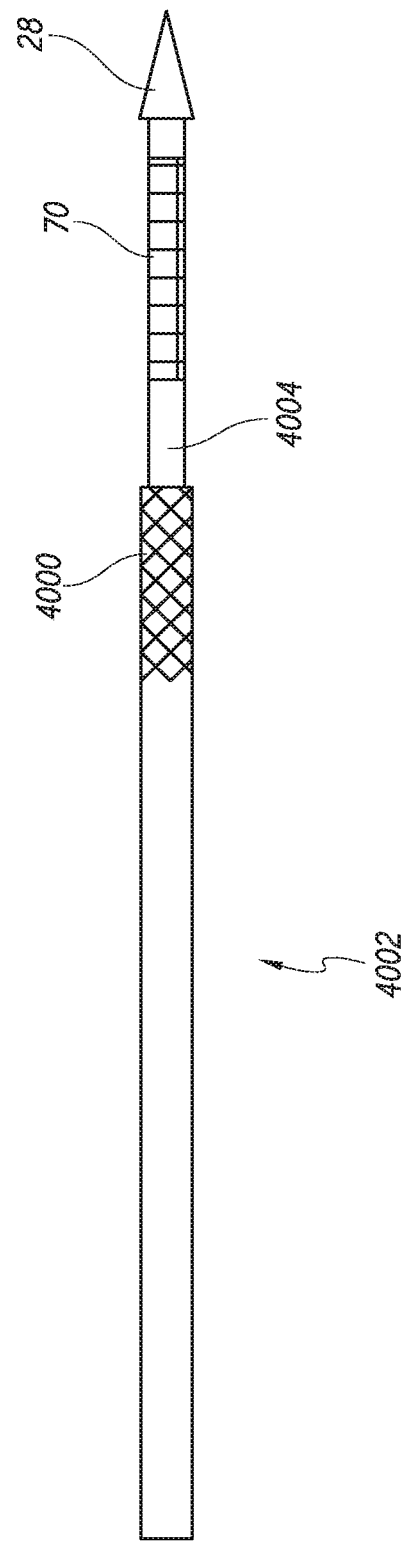
FIG. 40 illustrates a delivery system configured for use in a hinging delivery approach.

Accordingly, disclosed herein is a method for transseptal delivery that for a delivery system which can have at least a 90° bending ability as well as a flexible bending area, such as U.S. Pat. Pub. Nos. 2011/0137397 and U.S. Pat. Pub. No. 2014/0222136, both of which are hereby incorporated by reference in their entirety, or the above disclosed delivery system using a steering catheter. The general delivery system structure is shown in FIGS. 39-40. In particular, FIG. 39 illustrates a non-flex zone (section A) and a flex zone (section B) of a steering catheter 4002. As shown in FIG. 40, the delivery system can include a steering catheter 4002 as the outermost shaft. FIG. 40 illustrates the flex zone 4000 (such as section B of FIG. 39) of the steering catheter 4002, as shown at the distal end of the steering catheter 4002. Thus, the crimped valve 70 is slidable within the steering catheter 4002, such as within another sheath 4004. In some embodiments, sheath 4004 can be equivalent the outer sheath assembly 22 discussed above.

Figure 41:
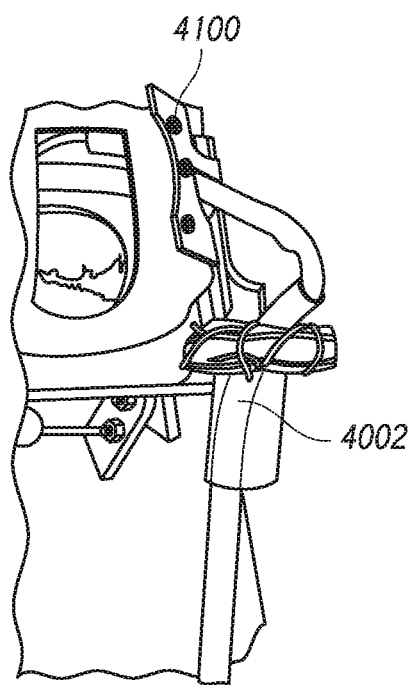
FIG. 41 illustrates steering a catheter away from the fossa ovalis during use of the delivery system.
Figure 42A:
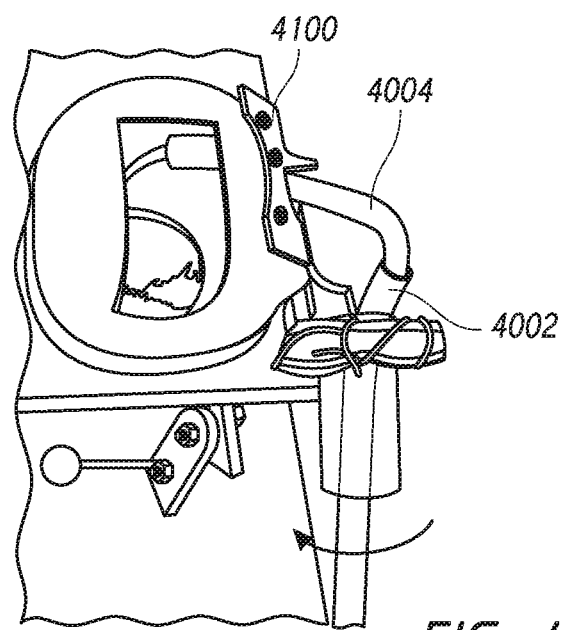
FIG. 42A illustrates applying a force on the fossa ovalis to create a hinge point.
Figure 43:
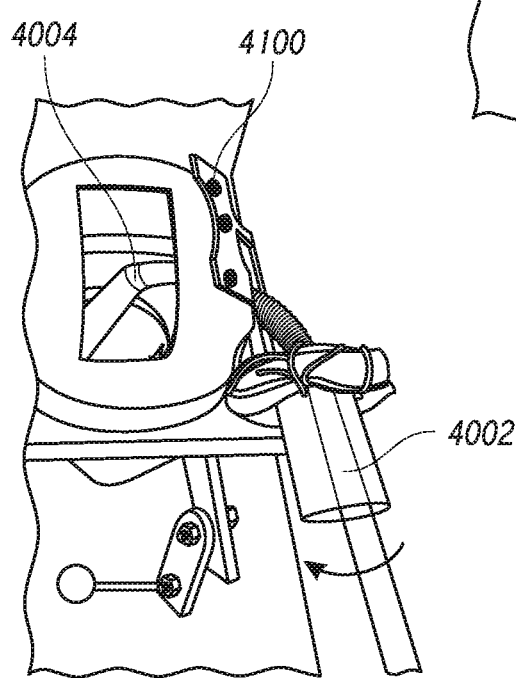
FIG. 43 illustrates the approach direction of the delivery system after hinging on the fossa ovalis.

Specifically, the disclosed methodology utilizes space within the right atrium in conjunction with usage of the fossa ovalis as a hinge which enables tracking of the prosthesis 70 from the septum into the left ventricle. This can be performed by bending the steering catheter 4002 away from the fossa ovalis, opposite to the intuitive direction of towards and into the fossa ovalis that is typically done, and using the fossa ovalis as a hinge by raising the prosthesis' proximal end in the right atrium while its distal end is in the left atrium. FIGS. 41-43 illustrate this procedure on a mockup heart.

The general steps for the transseptal approach are as below:

Delivery system insertion over a guide wire

Advance delivery system over the guide wire until approximately 5 mm of the implant distal end enters the left atrium through a hole in the fossa ovalis 4100.

Place the flex zone 4000 of the steering catheter 4002 approximately 2 cm proximal to the fossa ovalis 4100.

Retract the steering catheter 4002 approximately 5 mm.

Bend the steering catheter 4000 away from the fossa ovalis 4100 (such as about 90° away) as shown in FIG. 41. This action can utilize the right atrium space for maneuvering. As shown, the flex zone 4000 is turning away from the fossa ovalis 4100.

Pull back the guide wire until the soft tip of the guide wire stays inside the left ventricle (causing the nosecone to stay away from the posterior wall).

Figure 42B:
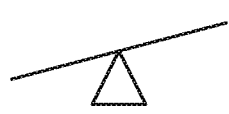
FIG. 42B illustrates a fulcrum using the fossa ovalis.

Torque the steering catheter 4000 counter clock wise (such as about 90°) until the steering catheter 4000 bending plane is parallel to the fossa ovalis plane, thereby pushing against the fossa ovalis 4100 creating a fulcrum on the fossa ovalis 4100. As a result, the proximal end of the implant 70 raises (toward the atrium) while the valve's distal end points towards the ventricle because the fossa ovalis acts as a hinge point. This is shown in FIG. 42A, with FIG. 42B illustrating the hinging action with the fossa ovalis 4100 as the fulcrum point.

Advance the implant 70 slowly while applying a 90° counterclockwise torque to the steering catheter 4002 until the implant "falls" into the left ventricle, as shown in FIG. 43.

Thus, to summarize, the implant 70 is steered by the steering catheter 4002 to be crossing the fossa ovalis, with a portion of the implant 70 in the left atrium and a portion in the right atrium. The steering catheter 4002 is then retracted back into the right atrium to be spaced away from the covered implant 70. The steering catheter 4002 is then steering away from the fossa ovalis and then torqued 90° (or about 90°), pressing against the fossa ovalis. During this torque, the proximal end of the implant 70 remaining in the right atrium rises in the right atrium and the distal end in the left atrium lowers as the fossa ovalis acts as the hinging point. The implant 70 can then be advanced into the final position.

From the foregoing description, it will be appreciated that an inventive product and approaches for implant delivery systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A steerable medical device component, comprising:
    a first elongate shaft having a proximal end and a distal end, the first elongate shaft comprising a bending section at the distal end;
    a second elongate shaft having a proximal end and a distal end slideable over the first elongate shaft;
    a nose cone coupled to the distal end of the first elongate shaft;

one or more pull wires connecting a proximal end of the nose cone and the distal end of the second elongate shaft; and a replacement heart valve releasably attached to the steerable medical device component;

wherein when the second elongate shaft is translated proximally, the one or more pull wires pulls the nose cone causing the bending section to bend; and wherein when the second elongate shaft is pushed distally to at least partially overlap with the bending section of the first elongate shaft, the bending section is configured to resist bending.

2. The steerable medical device component of claim 1, wherein the first and second elongate shafts are coaxial.

3. The steerable medical device component of claim 1, wherein the second elongate shaft comprises a pointed tip at the distal end.

4. The steerable medical device component of claim 1, wherein the bending section comprises a plurality of perforations.

5. The steerable medical device component of claim 4, wherein the perforations are diamond-shaped perforations.

6. The steerable medical device component of claim 1, wherein the bending section comprises a cut-out slot.

7. The steerable medical device component of claim 1, wherein the one or more pull wires comprise a plurality of pull wires.

8. The steerable medical device component of claim 7, wherein the first elongate shaft is configured to be bent in at least two planes.

9. The steerable medical device component of claim 1, further comprising a mid shaft having a distal end with an expanded diameter configured to at least partially cover the replacement heart valve.

10. The steerable medical device component of claim 9, further comprising an outer sheath configured translate proximally and distally over the second elongate shaft, and at least partially cover the replacement heart valve.

11. The steerable medical device component of claim 1, wherein the first elongate shaft comprises a metal hypotube.

12. The steerable medical device component of claim 1, wherein the first elongate shaft is encapsulated with a layer of PTFE.

13. The steerable medical device component of claim 1, wherein the second elongate shaft is a metal tube.

14. The steerable medical device component of claim 1, wherein the second elongate shaft is encapsulated with a layer of PTFE.

15. The steerable medical device component of claim 1, wherein the nose cone has a larger diameter than the first elongate shaft and the second elongate shaft.

16. The steerable medical device component of claim 1, wherein the one or more pull wires comprise one or more sutures.

17. The steerable medical device component of claim 1, wherein the replacement heart valve comprises a replacement mitral heart valve.

18. A steerable medical device component for implantation of a replacement heart valve, the steerable medical device component comprising:

a first elongate shaft having a proximal end and a distal end, the first elongate shaft comprising a bending section at the distal end, the bending section having a plurality of diamond-shaped perforations;

a second elongate shaft having a proximal end and a distal end slideable over the first elongate shaft;

a nose cone coupled to the distal end of the first elongate shaft, the nose cone having a diameter greater than a diameter of the first elongate shaft and the second elongate shaft; and a plurality of pull sutures connecting a proximal end of the nose cone and the distal end of the second elongate shaft, the plurality of pull sutures being separate from and connected to the nose cone and the second elongate shaft;

wherein when the second elongate shaft is translated proximally, the plurality of pull sutures pulls the nose cone causing the bending section to bend.

19. A steerable medical device component for implantation of a replacement heart valve, the steerable medical device component comprising:

a first elongate shaft having a proximal end and a distal end, the first elongate shaft comprising a bending section at the distal end, the bending section having a plurality of perforations;

a second elongate shaft having a proximal end and a distal end slideable over the first elongate shaft;

an outer sheath slidably disposed over the first elongate shaft and the second elongate shaft;

a mid shaft having a distal end with an expanded diameter;

a nose cone coupled to the distal end of the first elongate shaft, the nose cone having a diameter greater than a diameter of the first elongate shaft and the second elongate shaft;

at least one pull suture connecting a proximal end of the nose cone and the distal end of the second elongate shaft, the at least one pull suture being separate from and connected to the nose cone and the second elongate shaft;

wherein when the second elongate shaft is translated proximally, the at least one pull suture pulls the nose cone causing the bending section to bend;

wherein proximal translation of the outer sheath is configured to release a distal end of a replacement heart valve; and wherein proximal translation of the mid shaft is configured to release a proximal end of the replacement heart valve.

* * * * *

UNITED STATES PATENT AND TRADEMARK OFFICE
CERTIFICATE OF CORRECTION

PATENT NO. : 10,646,340 B2
APPLICATION NO. : 15/680030
DATED : May 12, 2020
INVENTOR(S) : Boaz Manash et al.

Page 1 of 1

It is certified that error appears in the above-identified patent and that said Letters Patent is hereby corrected as shown below:

On the Title Page

Item (72) Inventors should read:
--(72) Inventors: Boaz Manash, Givat Ada (IL);
                    Oren Cohen, Kadima (IL);--

Signed and Sealed this
Sixth Day of October, 2020

Andrei Iancu
*Director of the United States Patent and Trademark Office*